US 6,579,259 B2

(12) United States Patent
Stevens et al.

(10) Patent No.: US 6,579,259 B2
(45) Date of Patent: *Jun. 17, 2003

(54) ENDOVACULAR CARDIAC VENTING CATHETER AND METHOD

(75) Inventors: John H. Stevens, Palo Alto, CA (US); Jeffrey W. Krier, El Granada, CA (US); Kirsten L. Valley, Mountain View, CA (US); Philip C. Evard, Palo Alto, CA (US)

(73) Assignee: Heartport, Inc., Redwood City, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/344,543

(22) Filed: Jun. 25, 1999

(65) Prior Publication Data
US 2003/0040736 A1 Feb. 27, 2003

Related U.S. Application Data

(63) Continuation of application No. 08/694,916, filed on Nov. 30, 1996, now Pat. No. 5,916,193, which is a division of application No. 08/415,238, filed on Mar. 30, 1995, now abandoned, which is a continuation-in-part of application No. 08/282,192, filed on Jul. 28, 1994, now Pat. No. 5,584,803, which is a continuation-in-part of application No. 08/162,742, filed on Dec. 3, 1993, now abandoned, which is a continuation-in-part of application No. 08/123,411, filed on Sep. 17, 1993, now abandoned, which is a continuation-in-part of application No. 07/991,188, filed on Dec. 15, 1992, now abandoned, which is a continuation-in-part of application No. 07/730,559, filed on Jul. 16, 1991, now Pat. No. 5,370,685.

(51) Int. Cl.[7] .............................................. A61M 29/00
(52) U.S. Cl. .................................................. 604/96.01
(58) Field of Search .............................. 604/6.06, 6.09, 604/6.11, 6.14, 43, 96.01, 99.01, 103.11, 105, 106, 151

(56) References Cited

U.S. PATENT DOCUMENTS

| 3,592,184 A | 7/1971 | Watkins et al. |
| 4,129,129 A | 12/1978 | Amrine |
| 4,639,252 A | 1/1987 | Kelly et al. |

(List continued on next page.)

FOREIGN PATENT DOCUMENTS

WO    WO 96-38194    12/1996

OTHER PUBLICATIONS

Orejola et al. The Internal Ventricular Venting Loop Catheter. A New, Simplified, Single Cannulation Approach for a Ventricular Assist System, *ASAIO Journal* pp. 181–185 (1994).

Chellappan et al. "Gravity Venting of the Left Ventricle: A Useful Adjunct" *J. Extra–Corp. Tech.* 26(1):34–36 (1994).

(List continued on next page.)

Primary Examiner—Manuel Mendez

(57) ABSTRACT

A venting catheter, system and method are provided for withdrawing blood and other fluids from a patient's heart to facilitate decompressing the heart during cardioplegic arrest and cardiopulmonary bypass, without the need for a thoracotomy and without puncturing the aorta, pulmonary artery, or heart itself. The venting catheter is configured to be introduced into a peripheral vein and intraluminally advanced through the right side of the heart and into the pulmonary artery. The venting catheter includes a lumen configured to withdraw blood at a rate of at least about 50 ml/min at a pressure of no less than about −350 mmHg. A flow-directing means is provided to facilitate guiding the catheter into the pulmonary artery by being carried by blood flow through the heart. The cardiac venting system may include, in addition to the cardiac venting catheter, a cardiopulmonary bypass system to maintain circulation of oxygenated blood, and means for arresting the patient's heart.

5 Claims, 32 Drawing Sheets

U.S. PATENT DOCUMENTS

| | | | |
|---|---|---|---|
| 4,721,115 A | | 1/1988 | Owens |
| 4,794,928 A | * | 1/1989 | Kletschka ................... 606/194 |
| 4,808,163 A | | 2/1989 | Laub |
| 4,856,529 A | | 8/1989 | Segal |
| 4,889,137 A | | 12/1989 | Kolobow |
| 4,985,014 A | * | 1/1991 | Orejola ..................... 604/43 X |
| 5,011,469 A | * | 4/1991 | Buckberg et al. .......... 604/6.11 |
| 5,053,008 A | | 10/1991 | Bajaj |
| 5,102,390 A | | 4/1992 | Crittenden et al. |
| 5,158,540 A | * | 10/1992 | Wijay et al. ........ 604/101.05 X |
| 5,207,228 A | | 5/1993 | Roelandt et al. |
| 5,308,320 A | * | 5/1994 | Safar et al. ................ 604/6.14 |
| 5,370,618 A | | 12/1994 | Leonhardt |
| 5,522,961 A | | 6/1996 | Leonhardt |
| 5,571,215 A | | 11/1996 | Sterman et al. |
| 5,913,842 A | | 6/1999 | Boyd et al. ................... 604/28 |
| 6,027,476 A | | 2/2000 | Sterman et al. ............ 604/6.14 |

OTHER PUBLICATIONS

Stassano et al. "False aneurysm from the aortic vent site" *J. Cardiovas. Surg.* 23:401–402 (1982).

Shaw et al. "Ventricular Apical Vents and Postoperative Focal Contraction Abnormalities in Patients Undergoing Coronary Artery Bypass Surgery", *Circ.* 55:434–438 (1977).

Breyer et al. "Is a left ventricular vent necessary for coronary artery bypass operations performed with cardioplegic arrest!"*J. Thorac Cardiovasc Surg* 86:338–349 (1983).

Laughlin et al. "Left Heart Decompression via the Pulmonary Artery", *Thorac Cardiovasc. Surgeon* 31:117–118 (1983).

Little et al. "Use of the pulmonary artery for left ventricular venting during cardiac operations" J. Thorac. Cardiovasc Surg. 87:532–538 (1984).

Vucins et al. "Vent Stitch Entrapment of Swan–Ganz Catheters during Caridac Surgery" *Anesth Analg* 63:772–774 (1984).

Heimbecker et al. "A New Approach to Left Heart Decompression", *Ann Thor Surg.* 21:456–457 (1976).

Roberts et al. "Relative Efficacy of Left Ventricular Venting and Venous Drainage Techniques Commonly Used during Coronary Artery Bypass Graft Surgery", *Ann Thor Surg.* 36:444–452 (1983).

Schneider et al. "A Technique for Cardioplegic Infusion and Left Heart Venting during Coronary Artery Bypass Grafting" *Ann Thor Surg.* 36:105–106 (1983).

Pulmonary Artery Vent Cannula, Product No. 12004, DLP, Inc., Worldwide Medical Innovations, Product Catalog, 3rd Edition, 1993, p. 35.

American Edwards Laboratories, Edslab, *Thermodilution and Monitoring Catheters*, Instruction pamphlet, no date.

Bourassa, "Cardiovascular Catheters, Sterile," USCI, A Division of C.R. Bard, Inc., Jun. 1972, 4 pages.

DLP Product Catalog, Third Edition, Cardiac Vents Sumps, 1993, p.35.

Medtronic Bio–Medicus, Inc., Bio–Medicus Cannula Instructions for Use Manual , Sterile and Non–Pyrogenic Single–Use Only, PN 85281 Rev C (10–91).

Webster Laboratories, Webster Laboratories Electrode Catheter—Deflectable Tip, Product Information, Innovations in Electrophysiology, M–5276–04C.

World Medical Manufacturing Corporation, Polycath brochure, 1996.

* cited by examiner

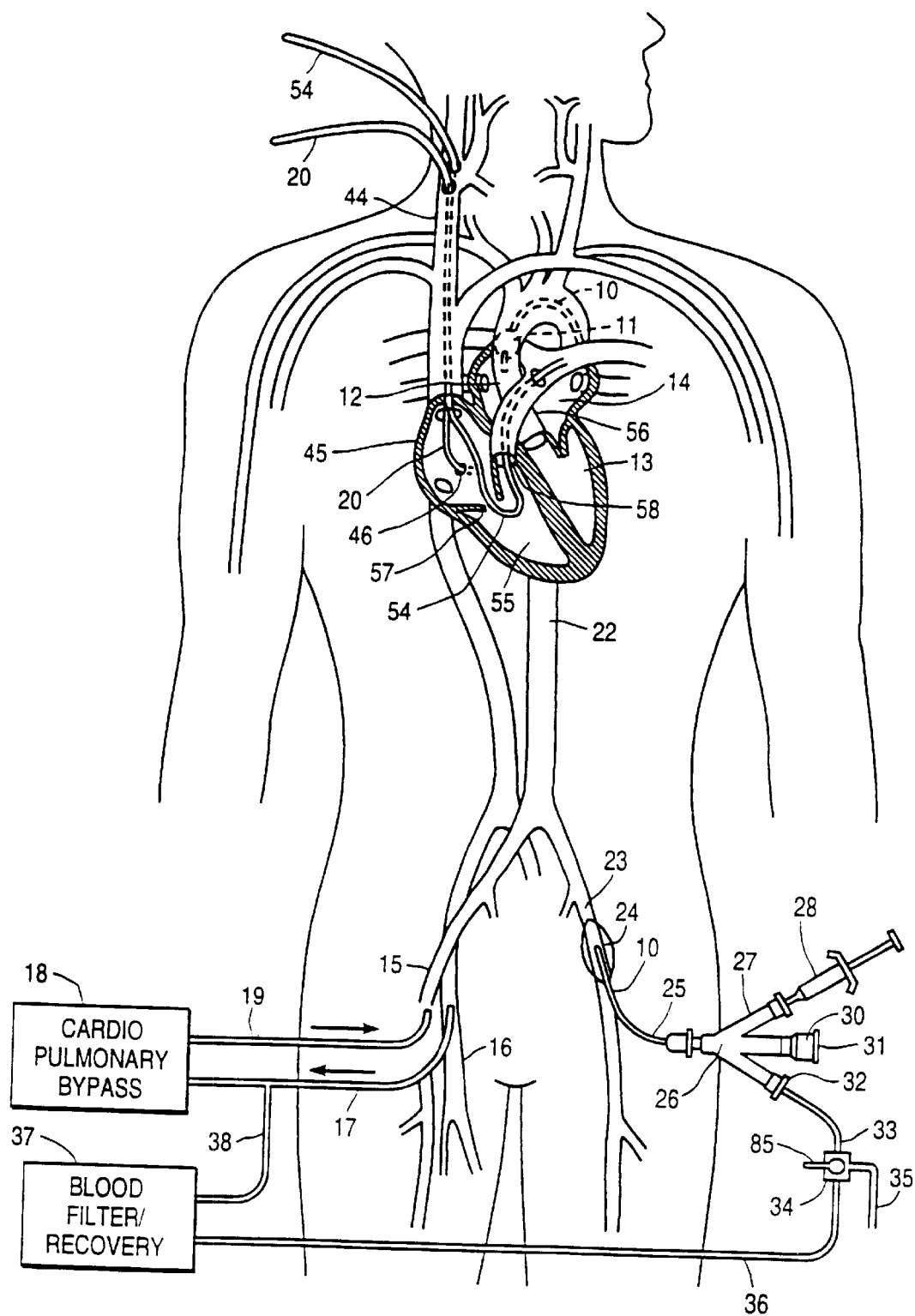
FIG_1

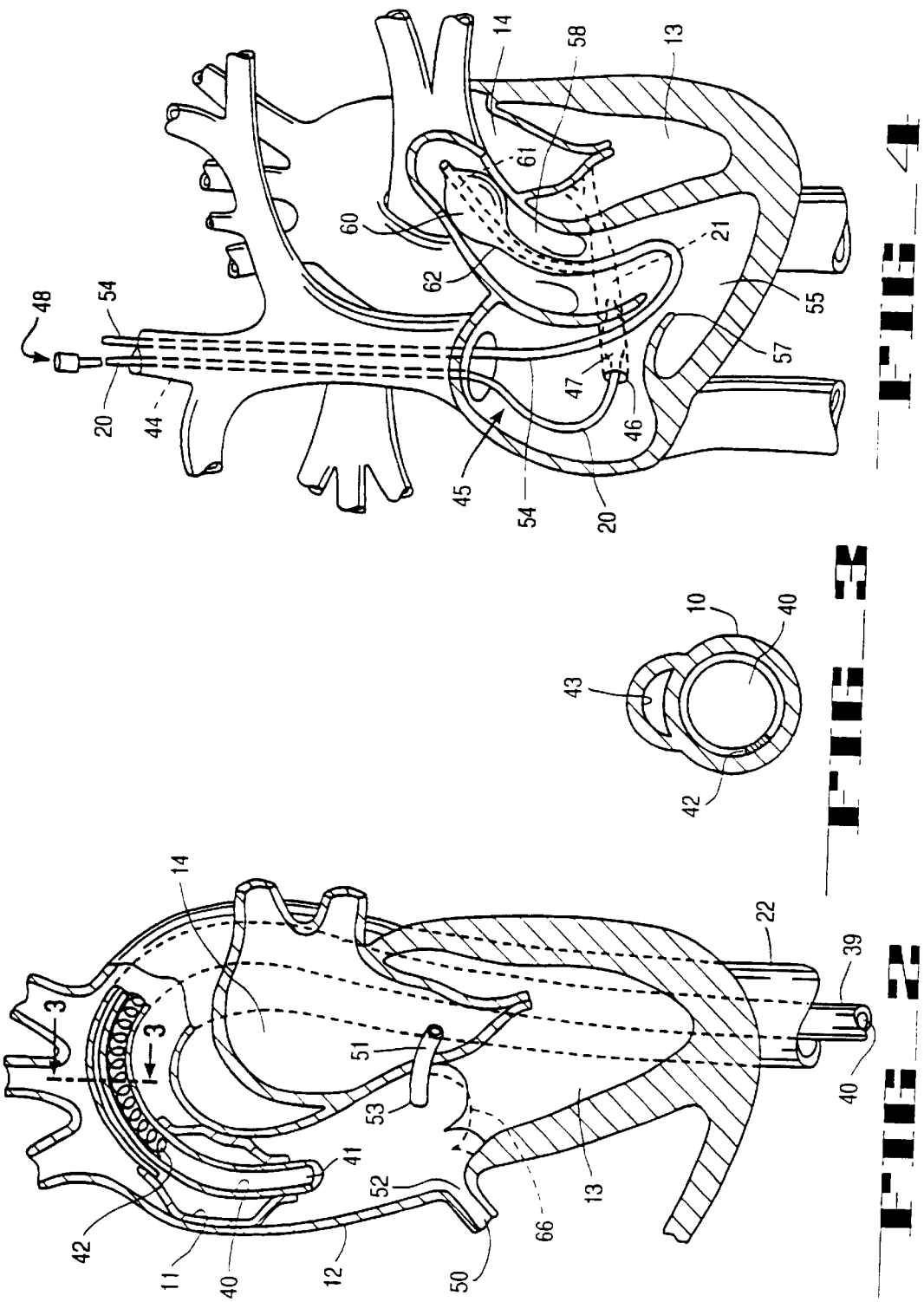

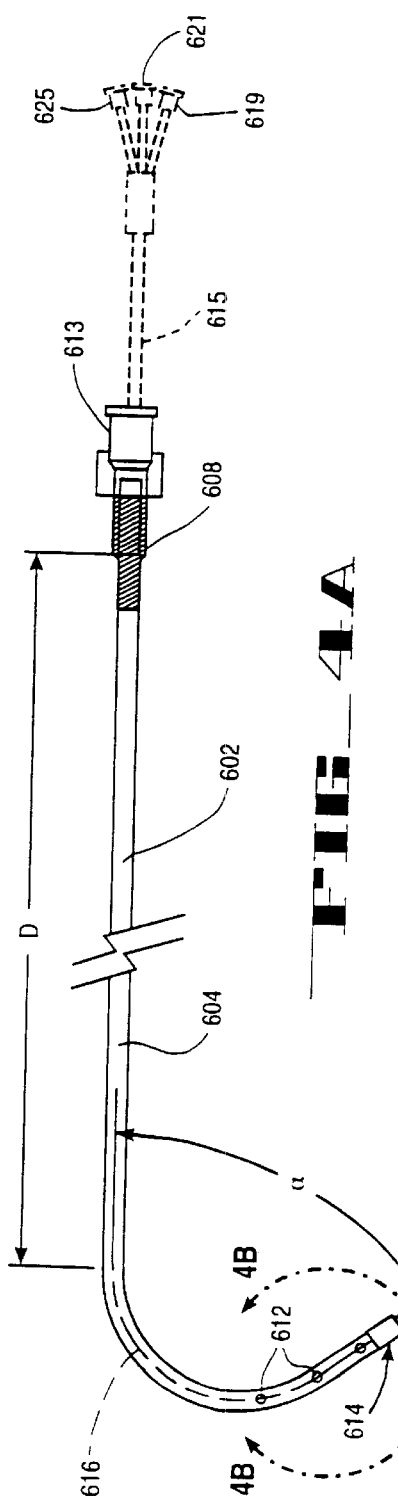
FIG. 4A
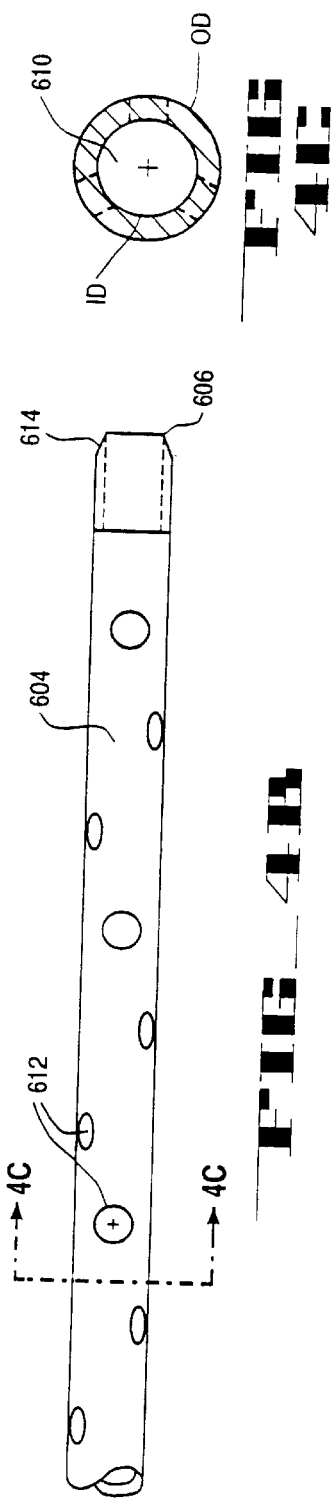
FIG. 4C
FIG. 4B

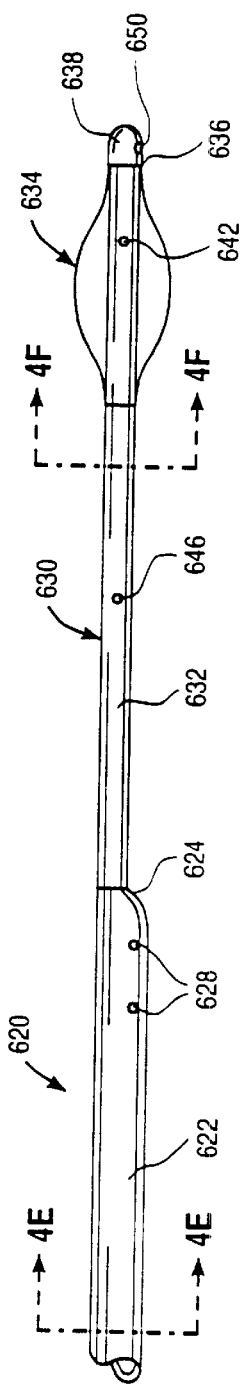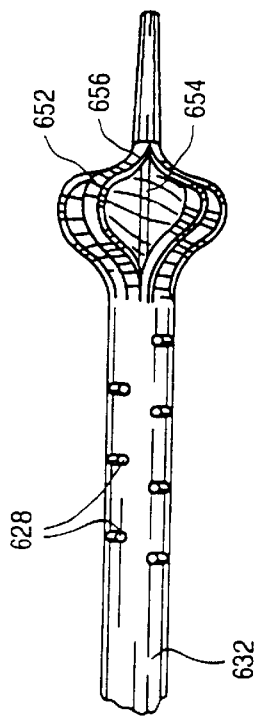
FIG._4D  FIG._4E  FIG._4F  FIG._4G

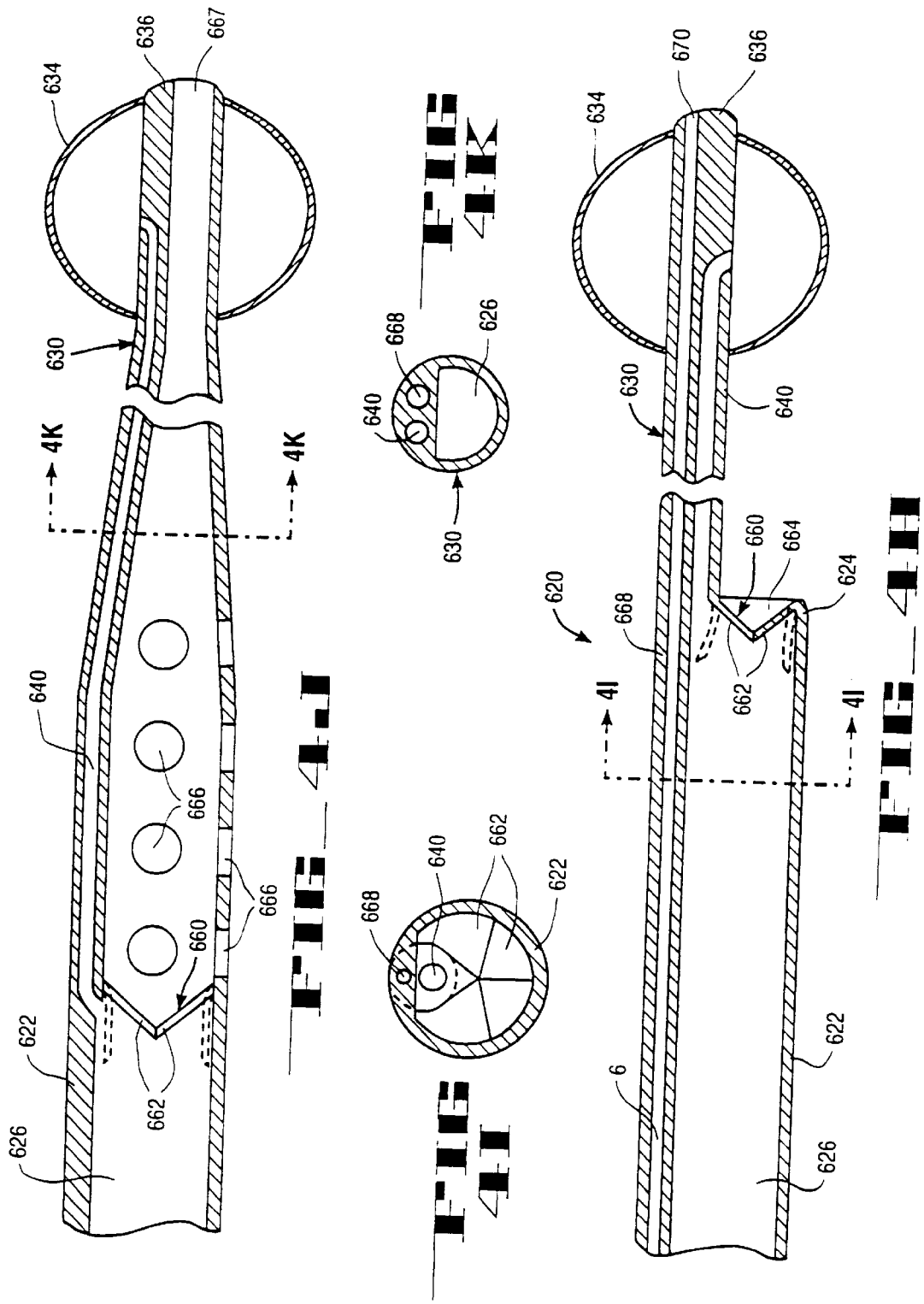

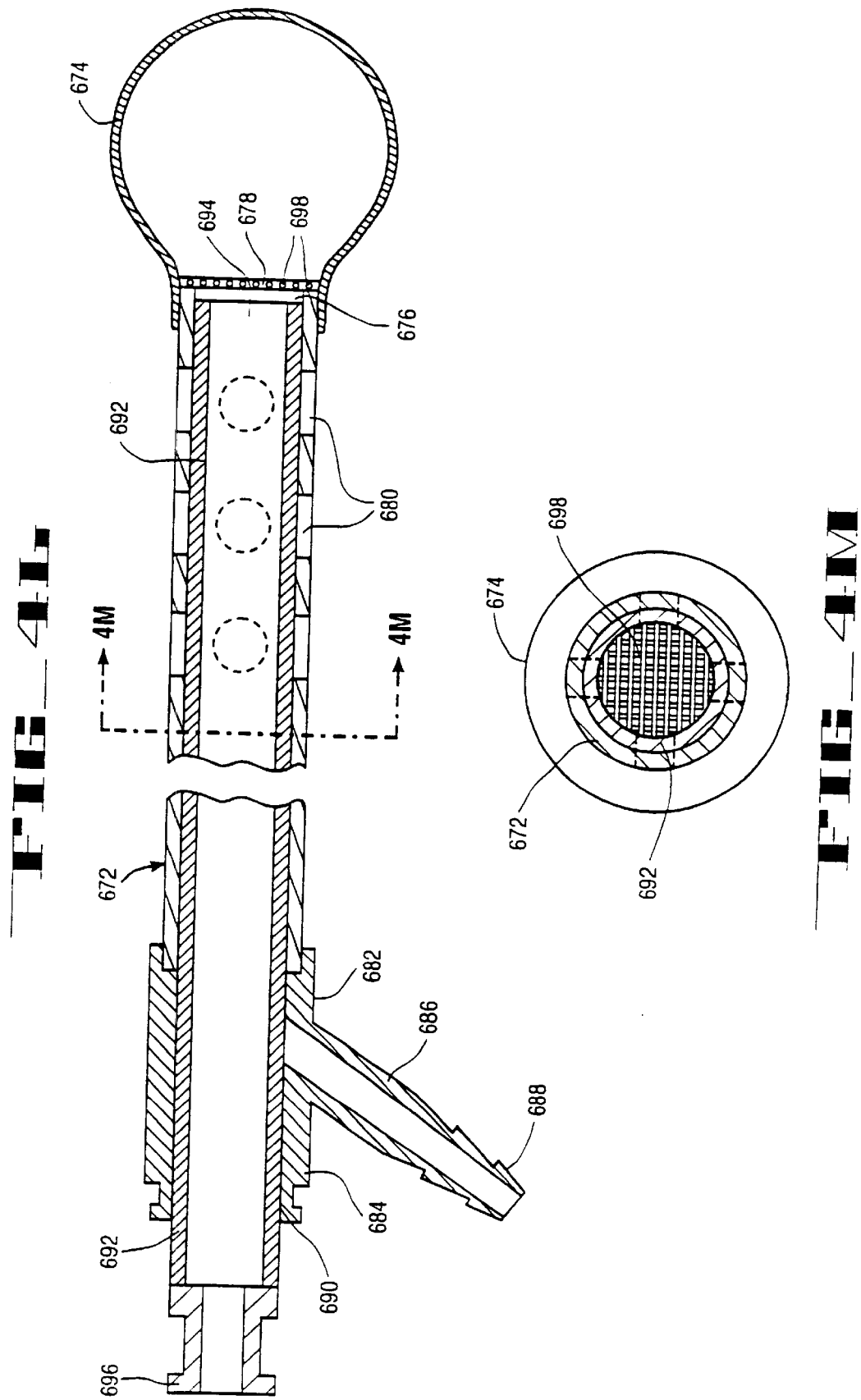
FIG_4L
FIG_4M

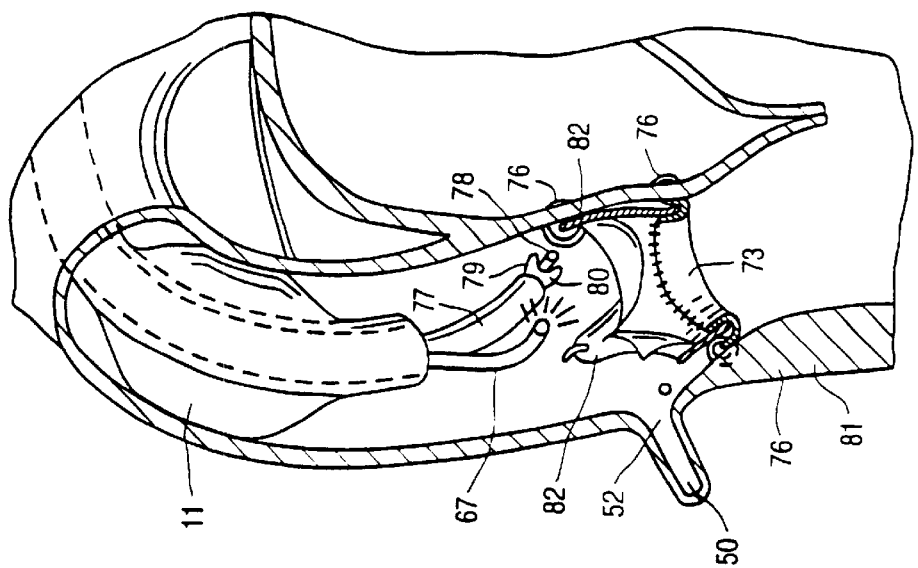
FIG_7
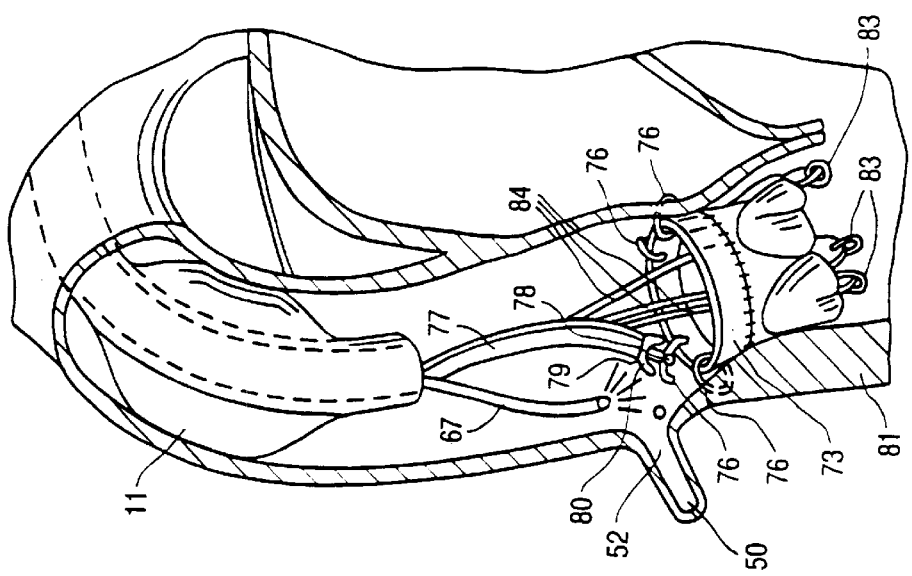
FIG_8

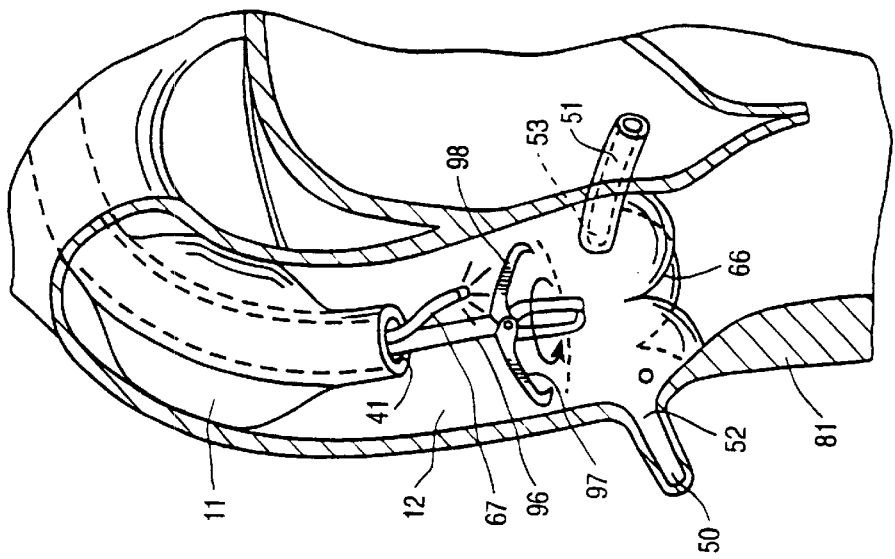
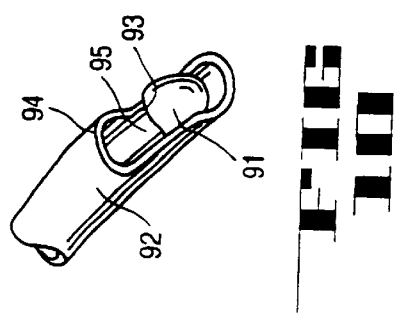
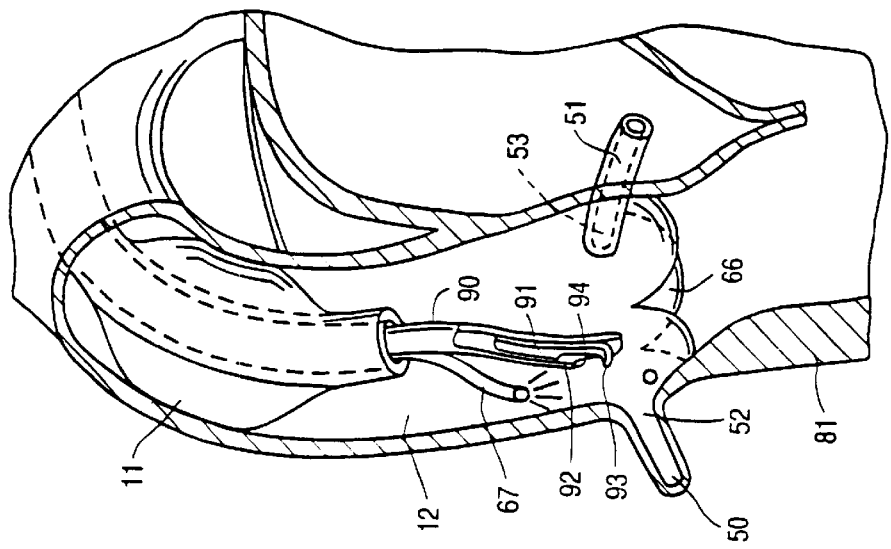

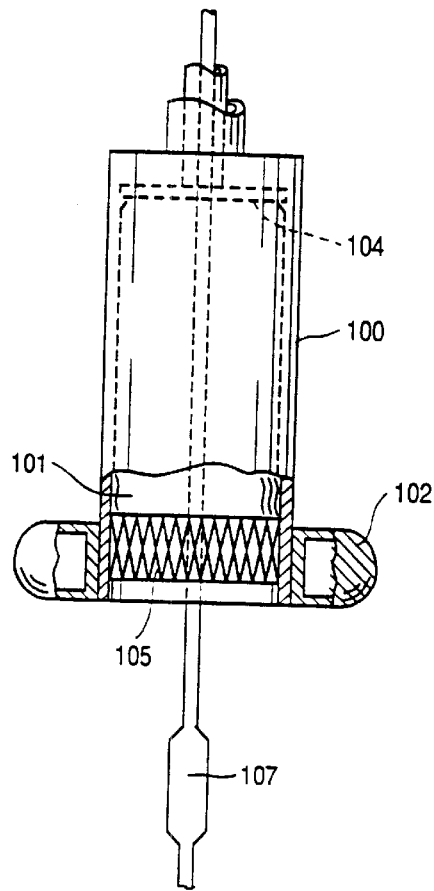
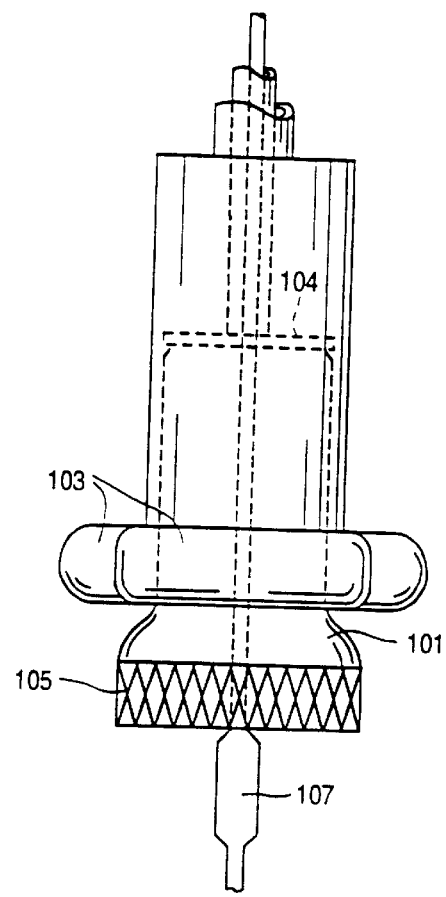
FIG_12   FIG_13
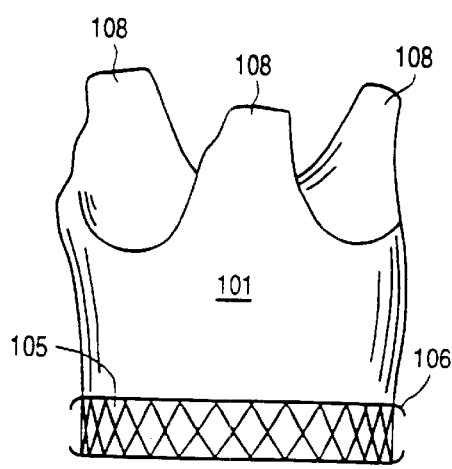
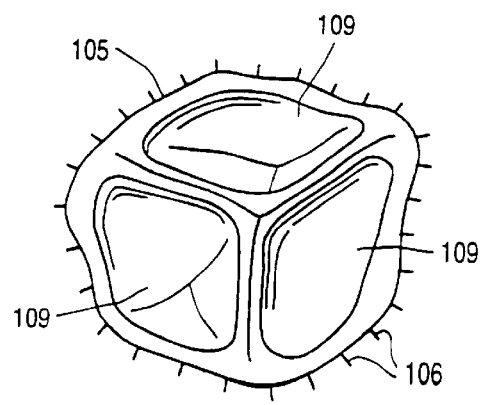
FIG_14   FIG_15

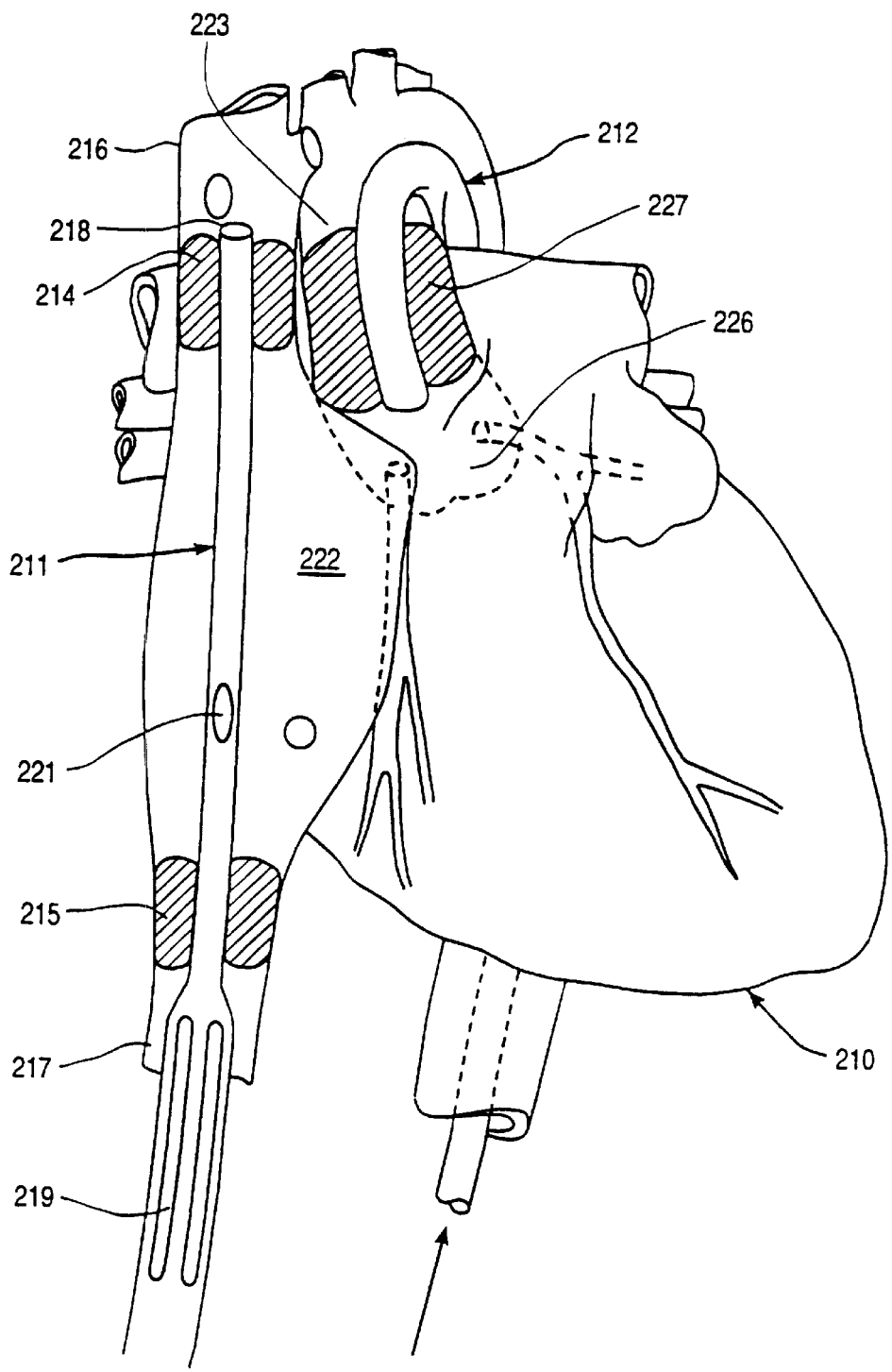
FIG_16

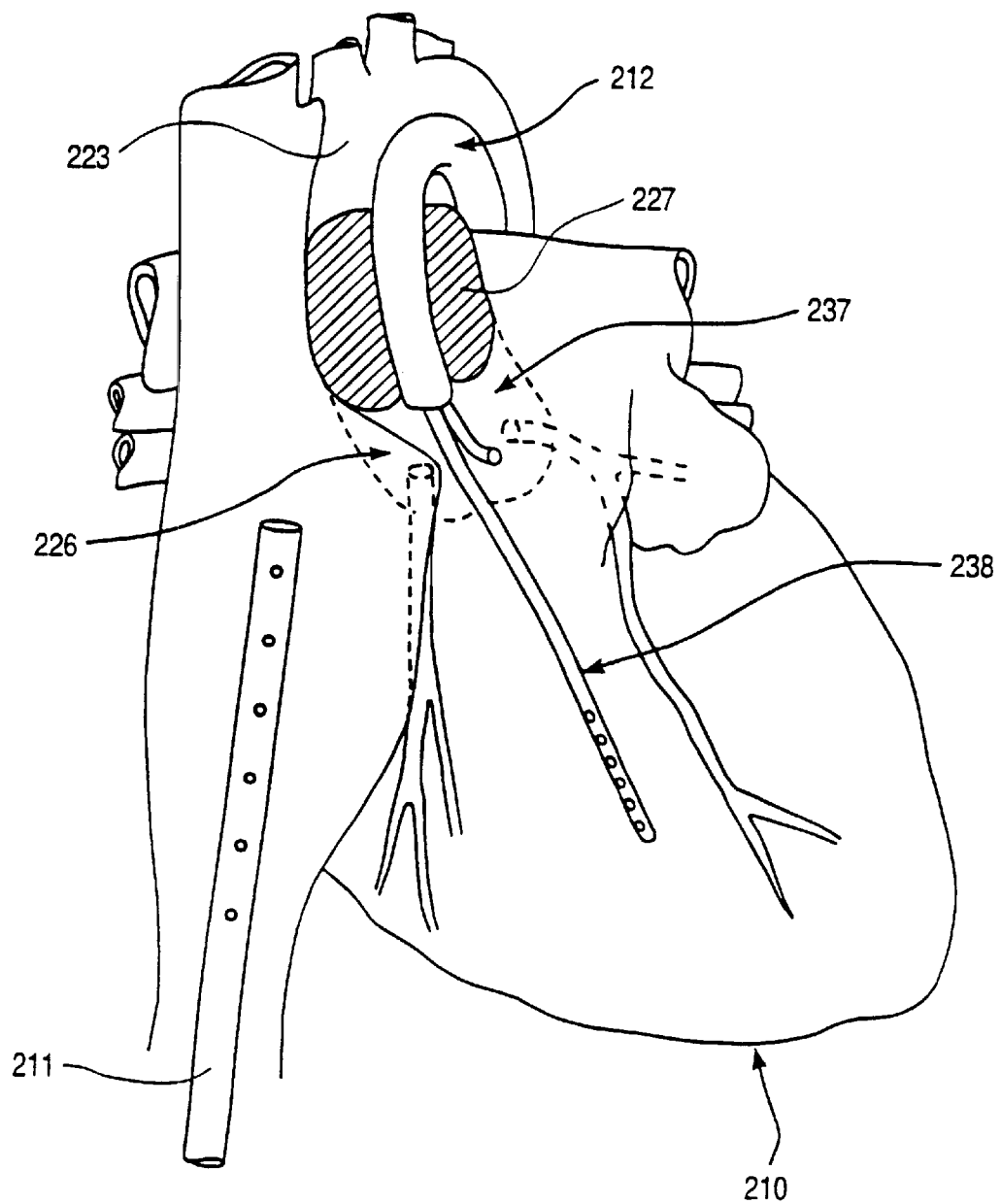
FIG_17

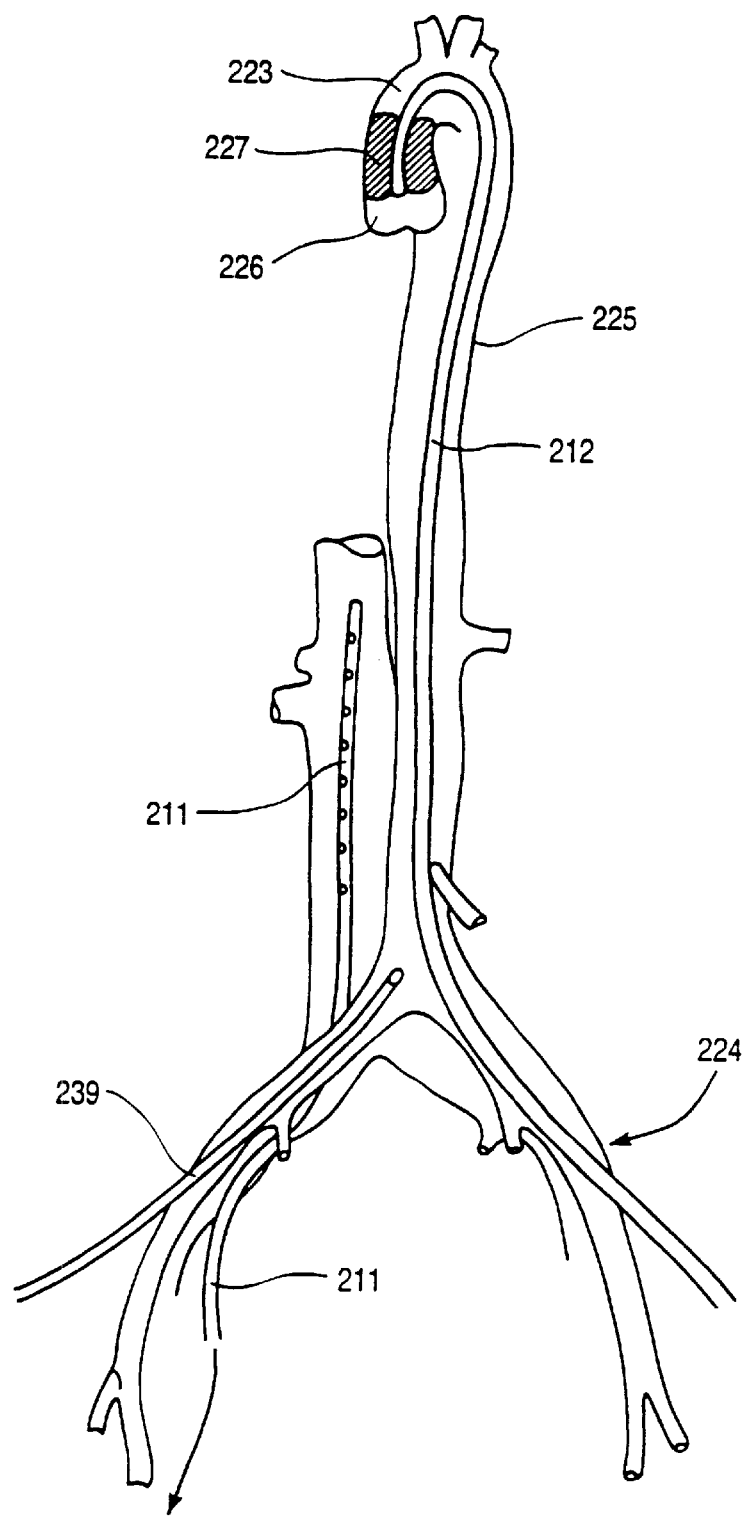
FIG_18

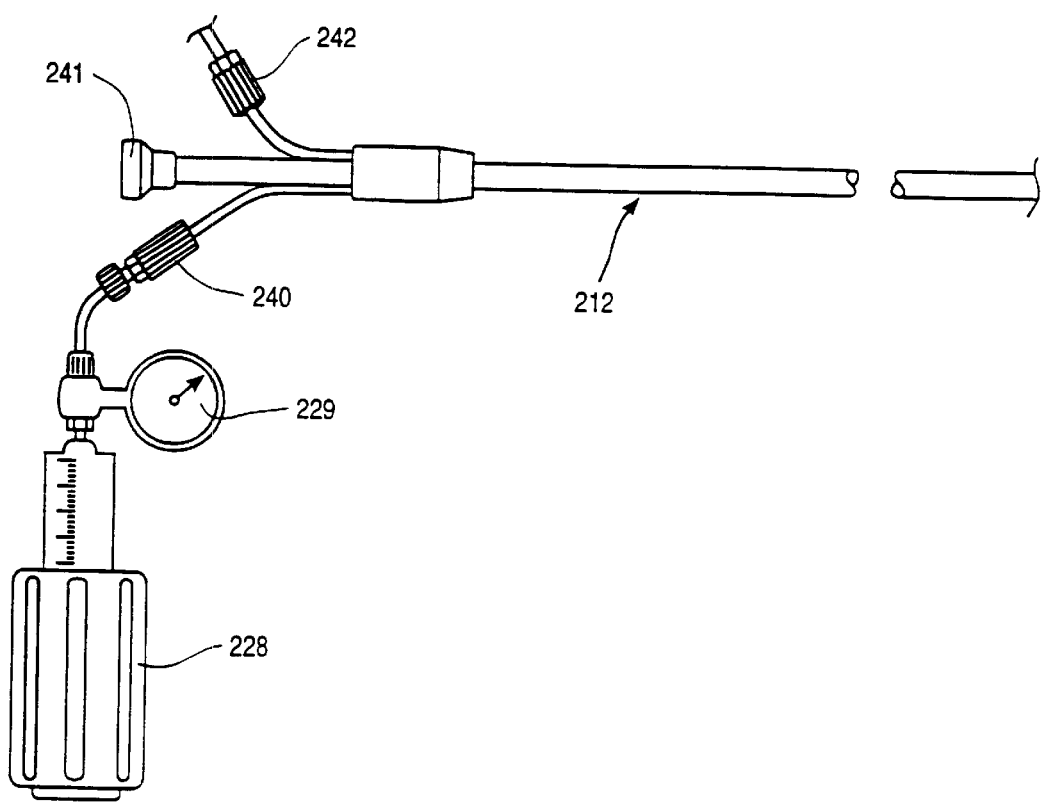
FIG_19

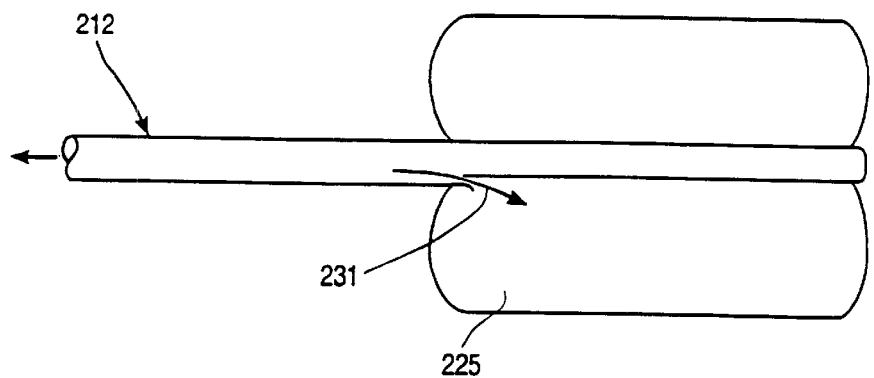
FIG_20
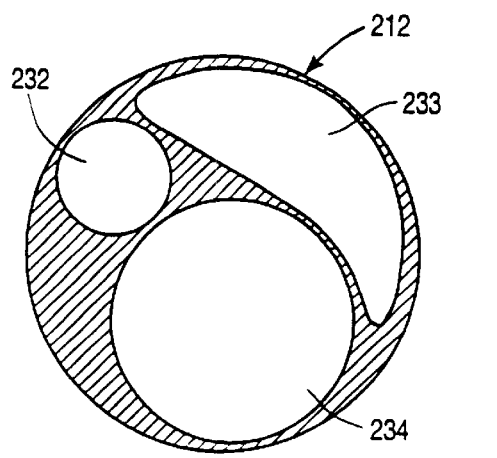
FIG 21A
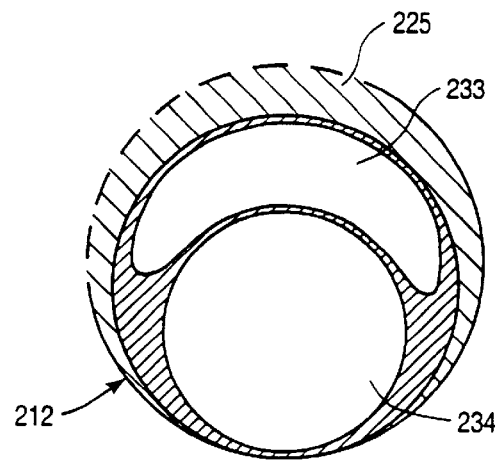
FIG 22
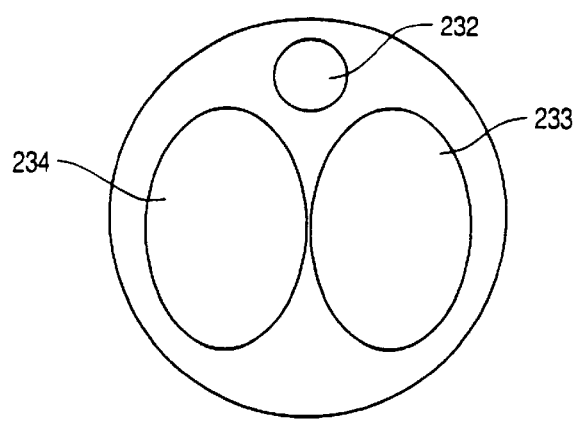
FIG_21B

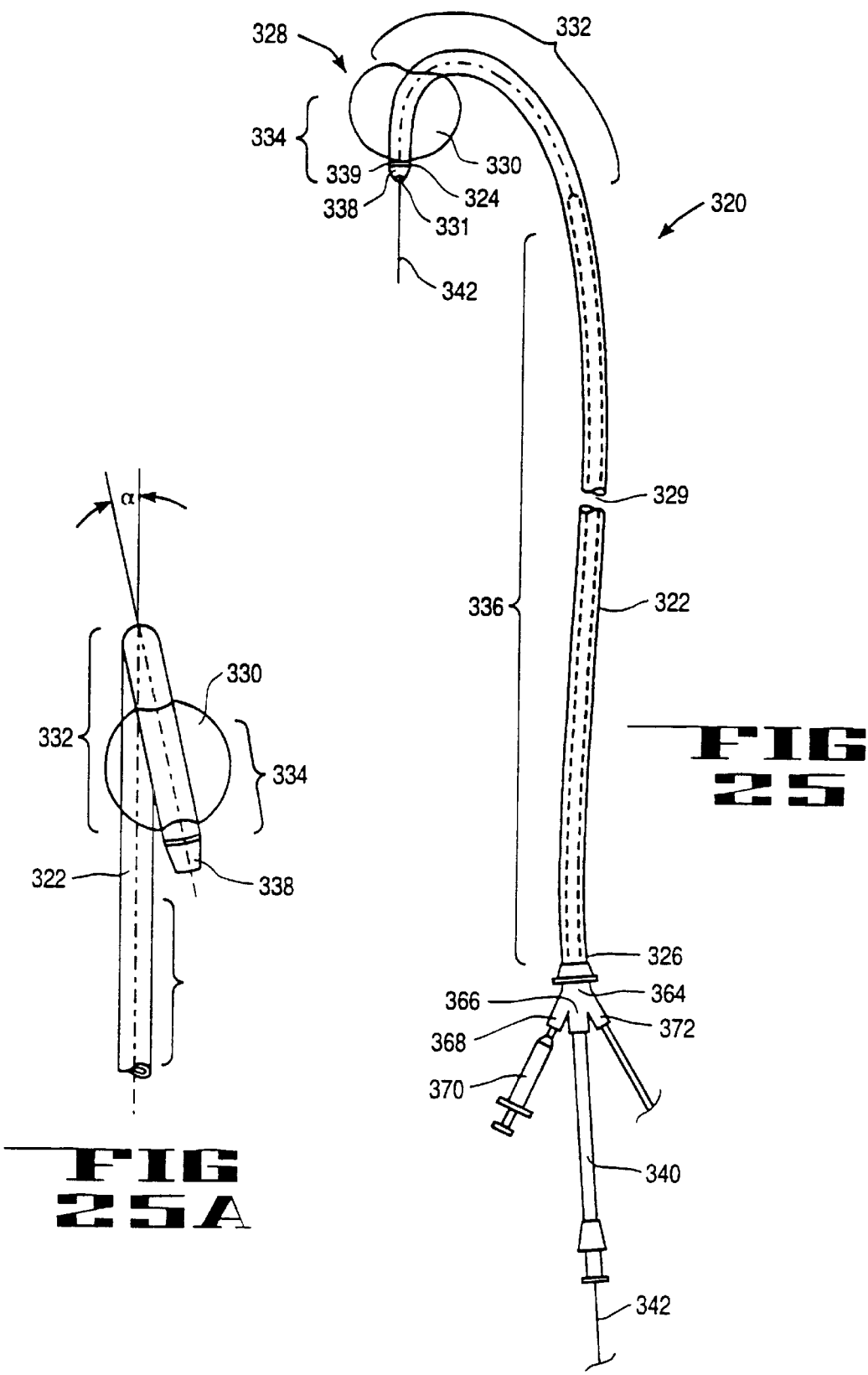

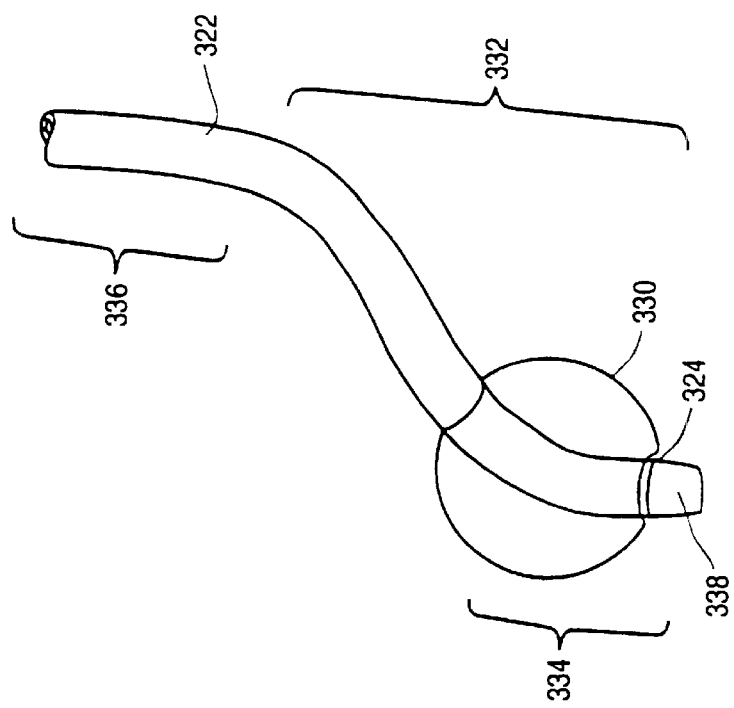
FIG_25E
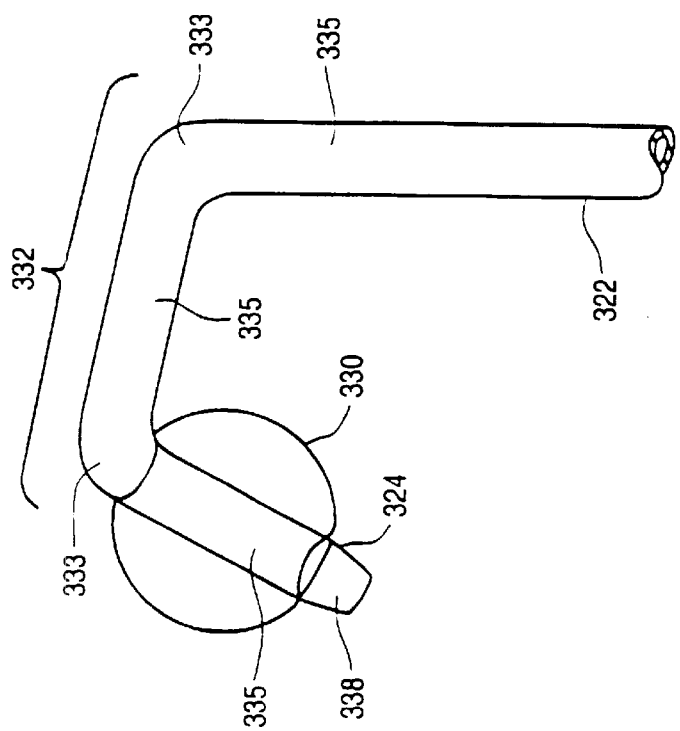
FIG_25D

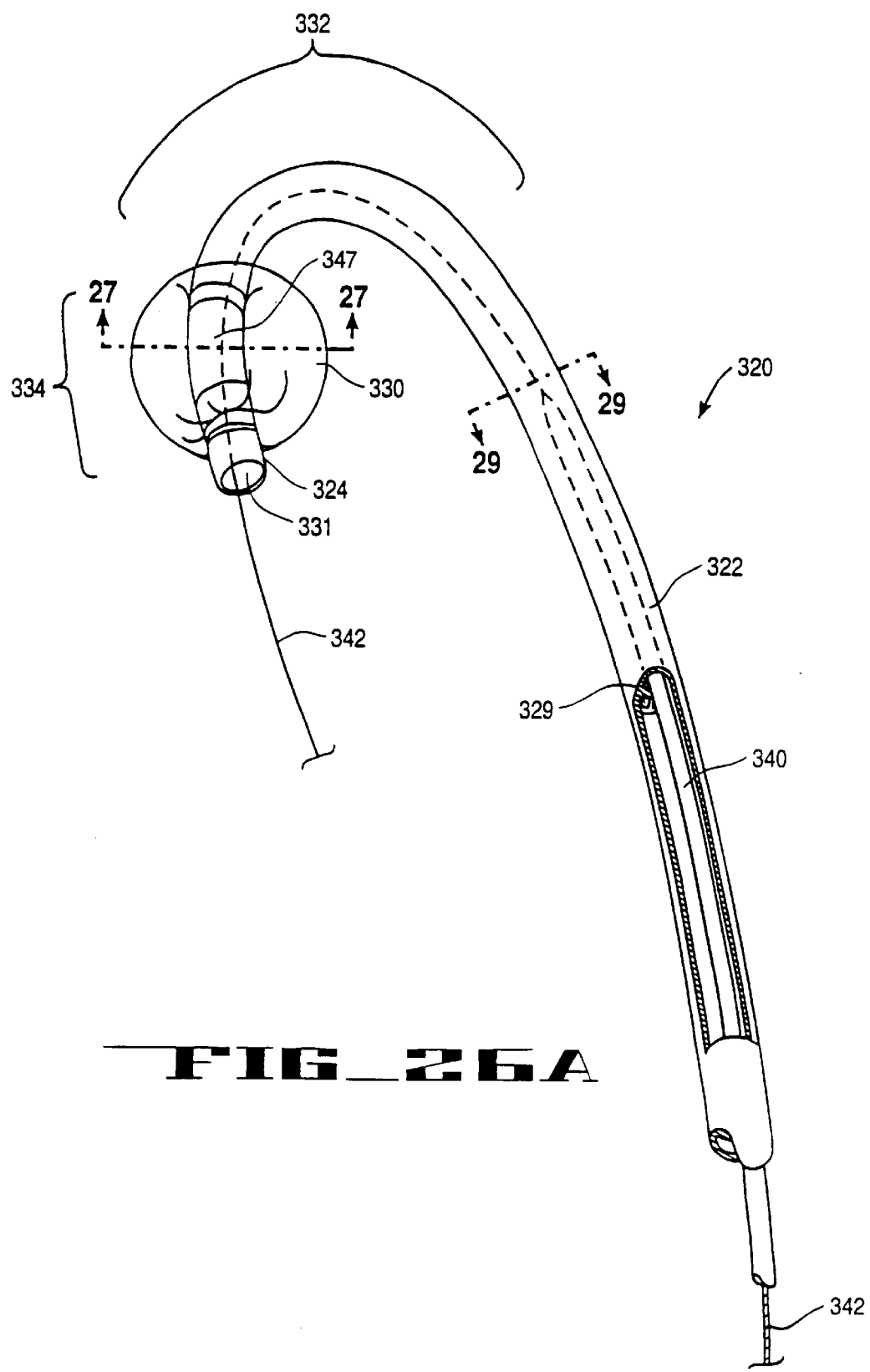
FIG_26A

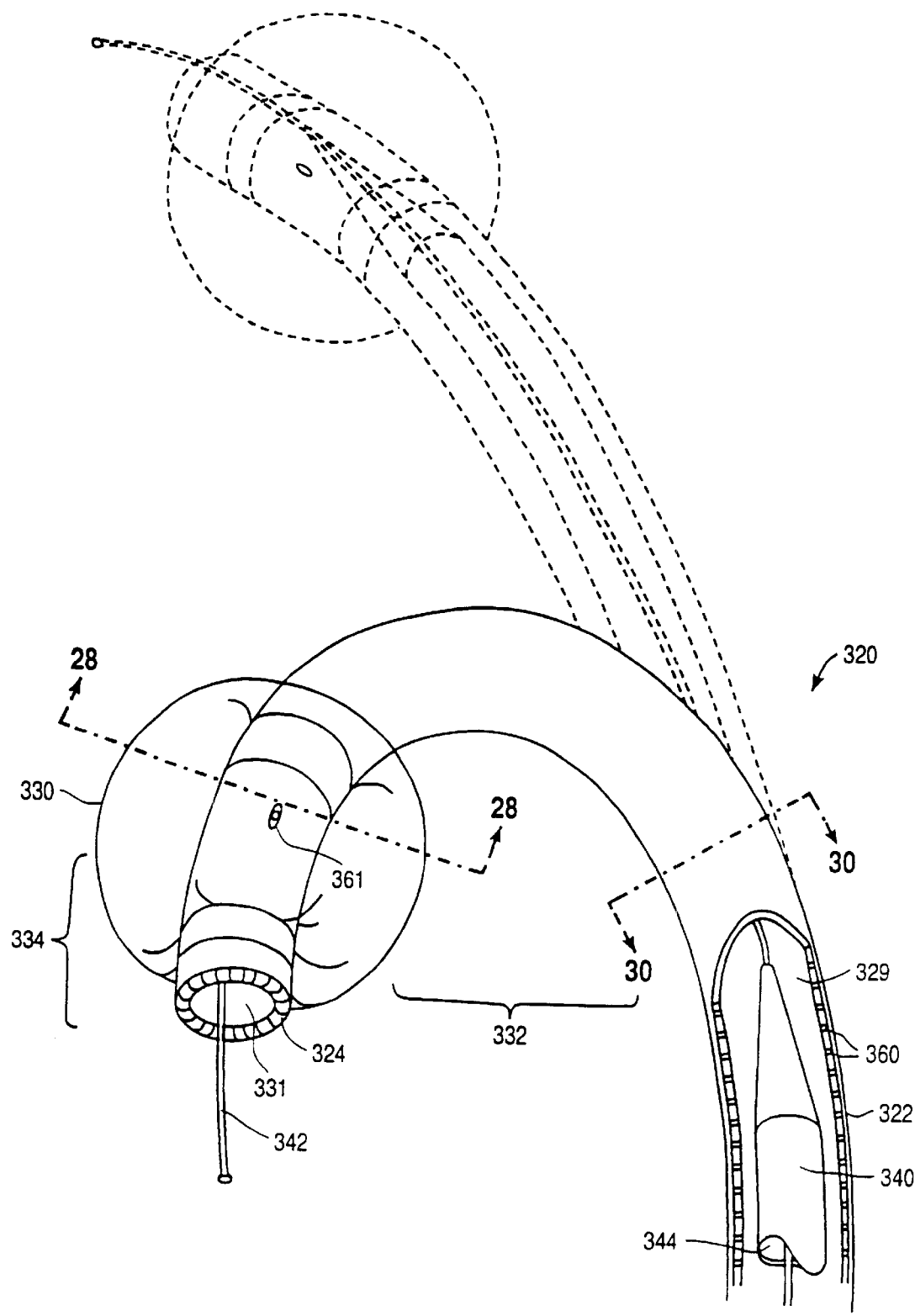
FIG_26B

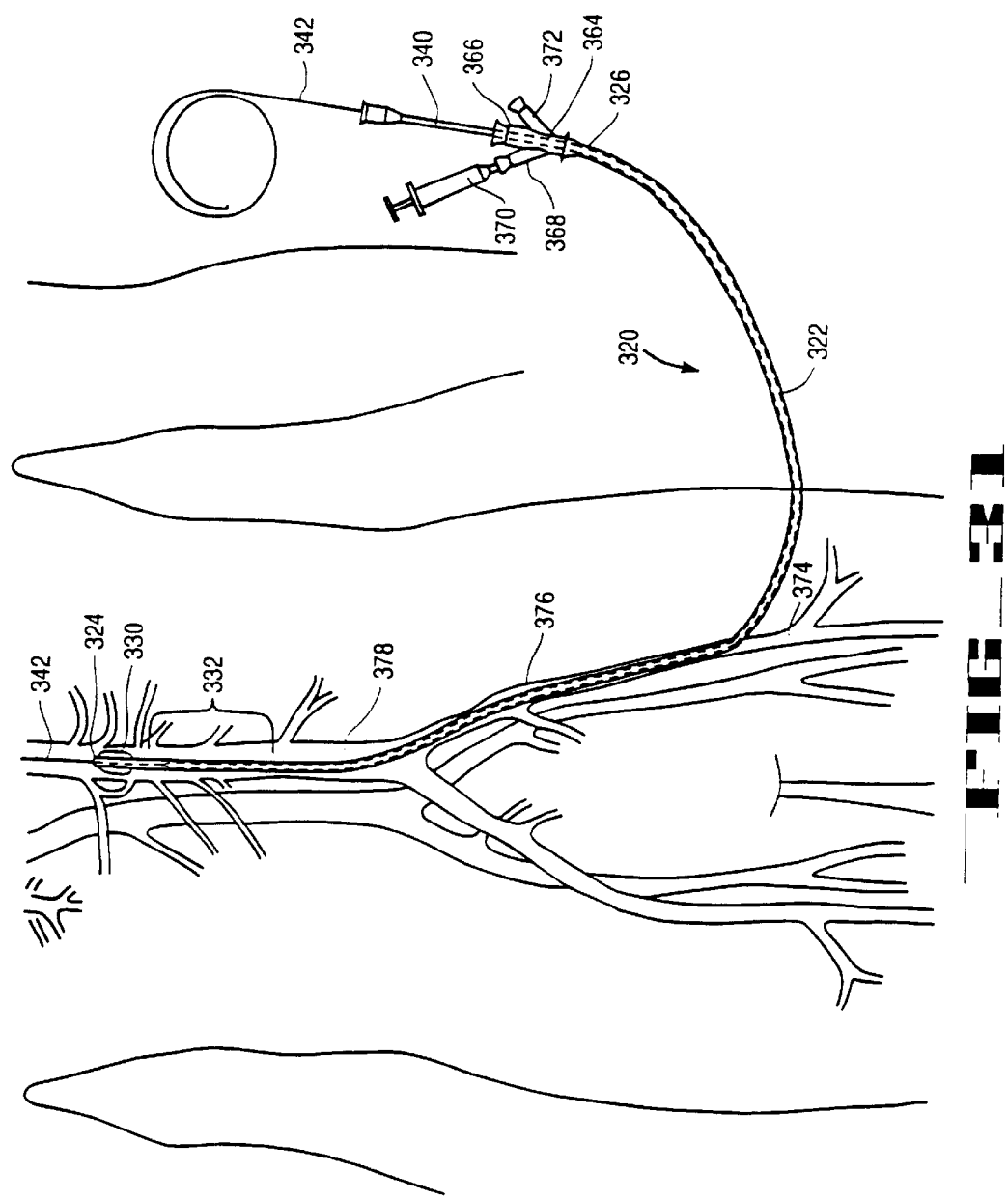

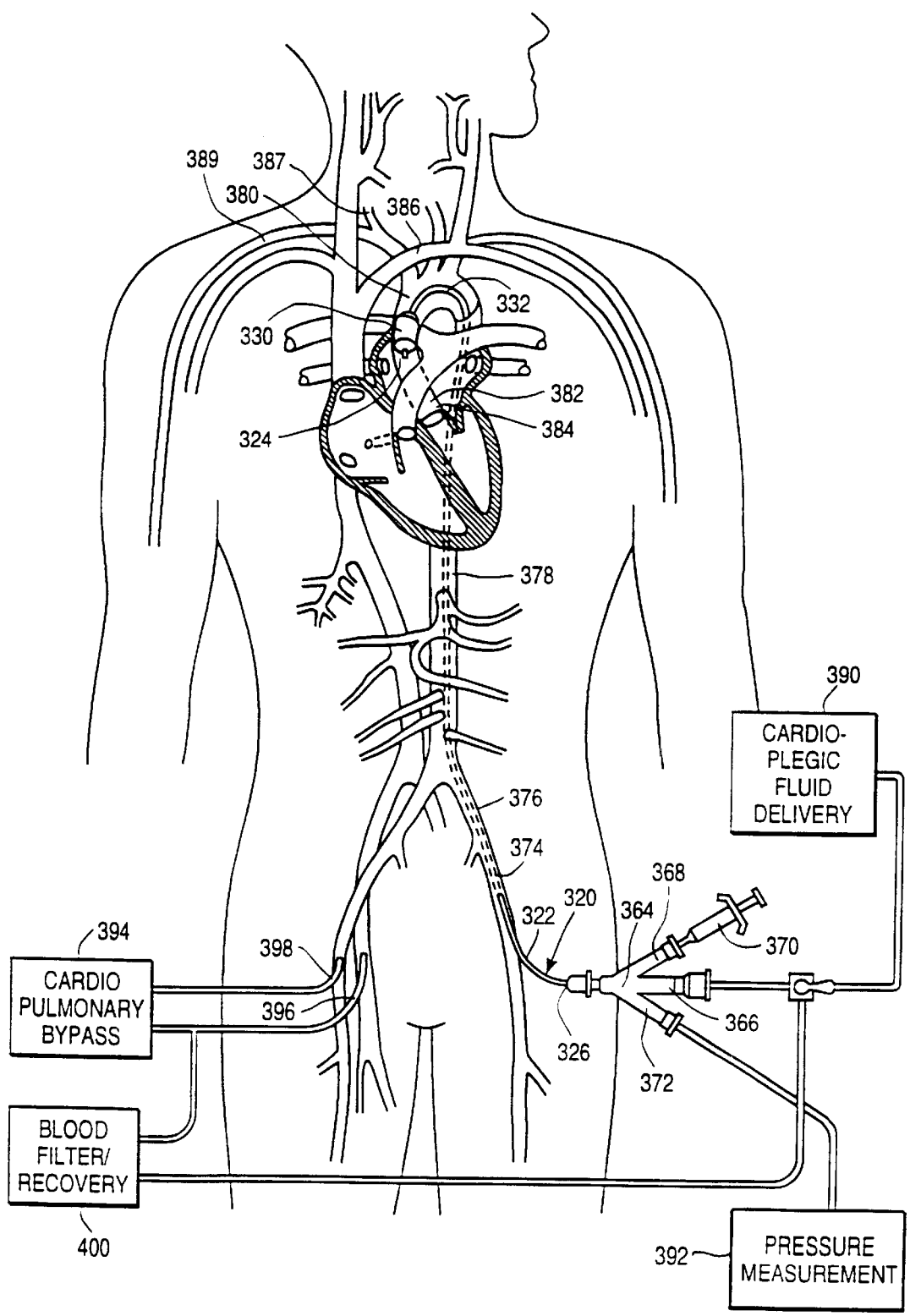
FIG_32

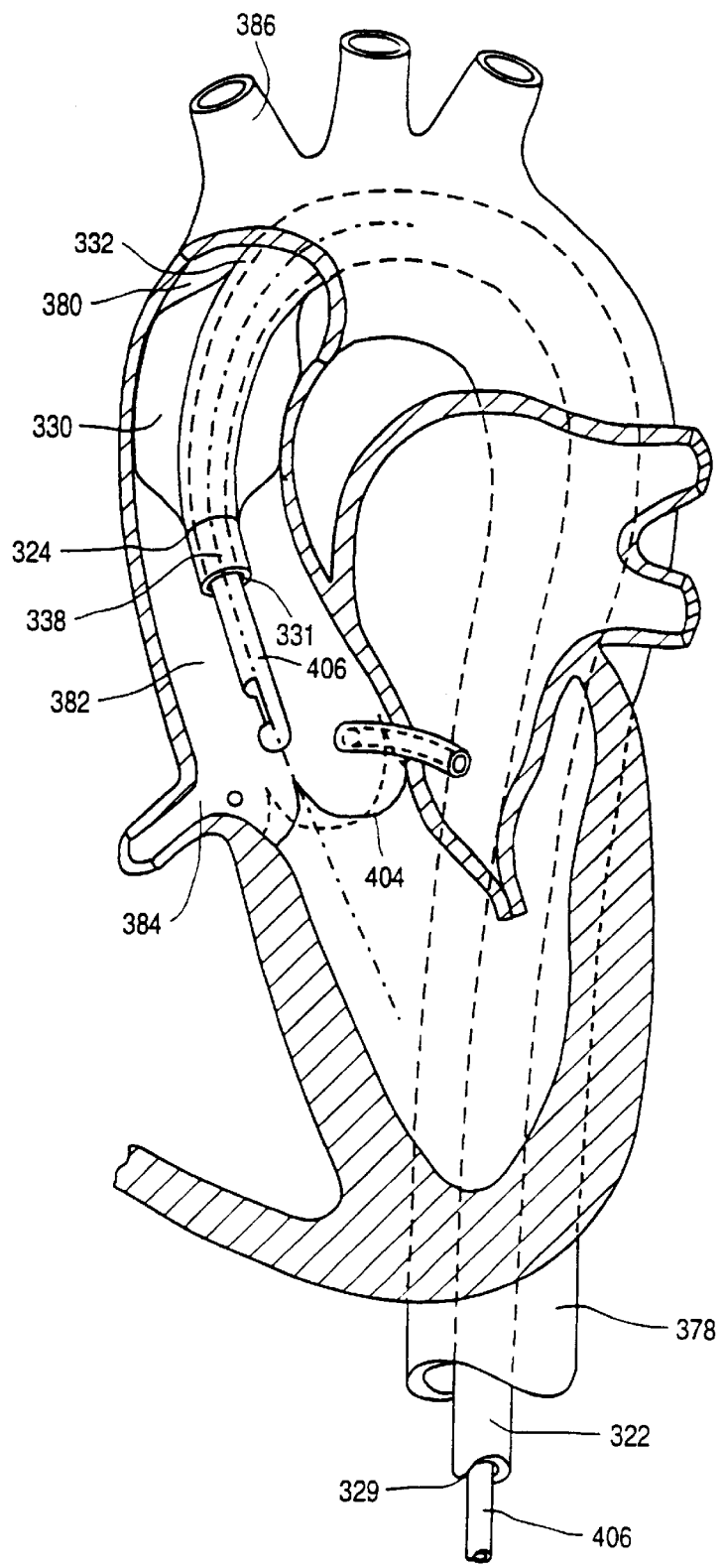
FIG_33

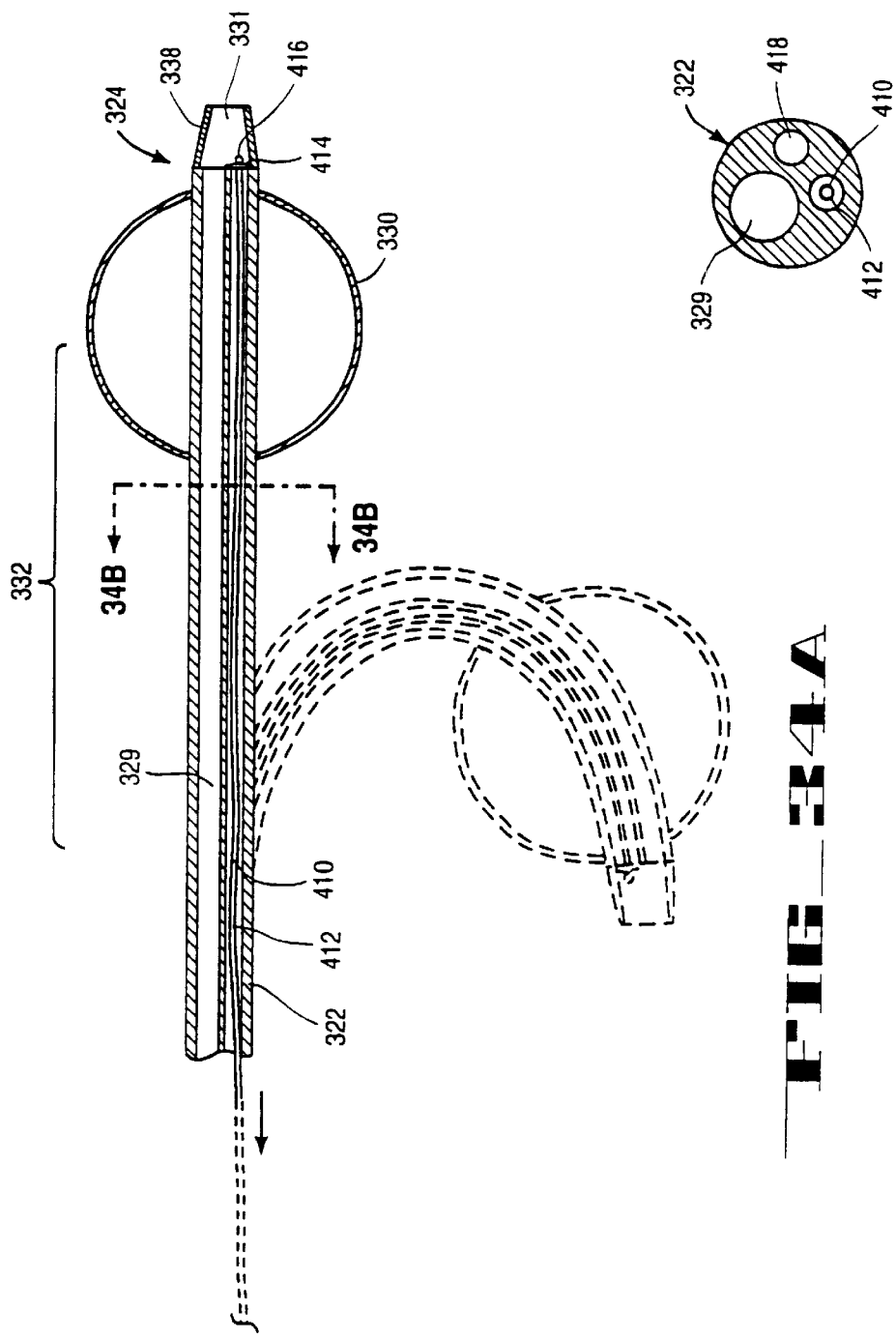

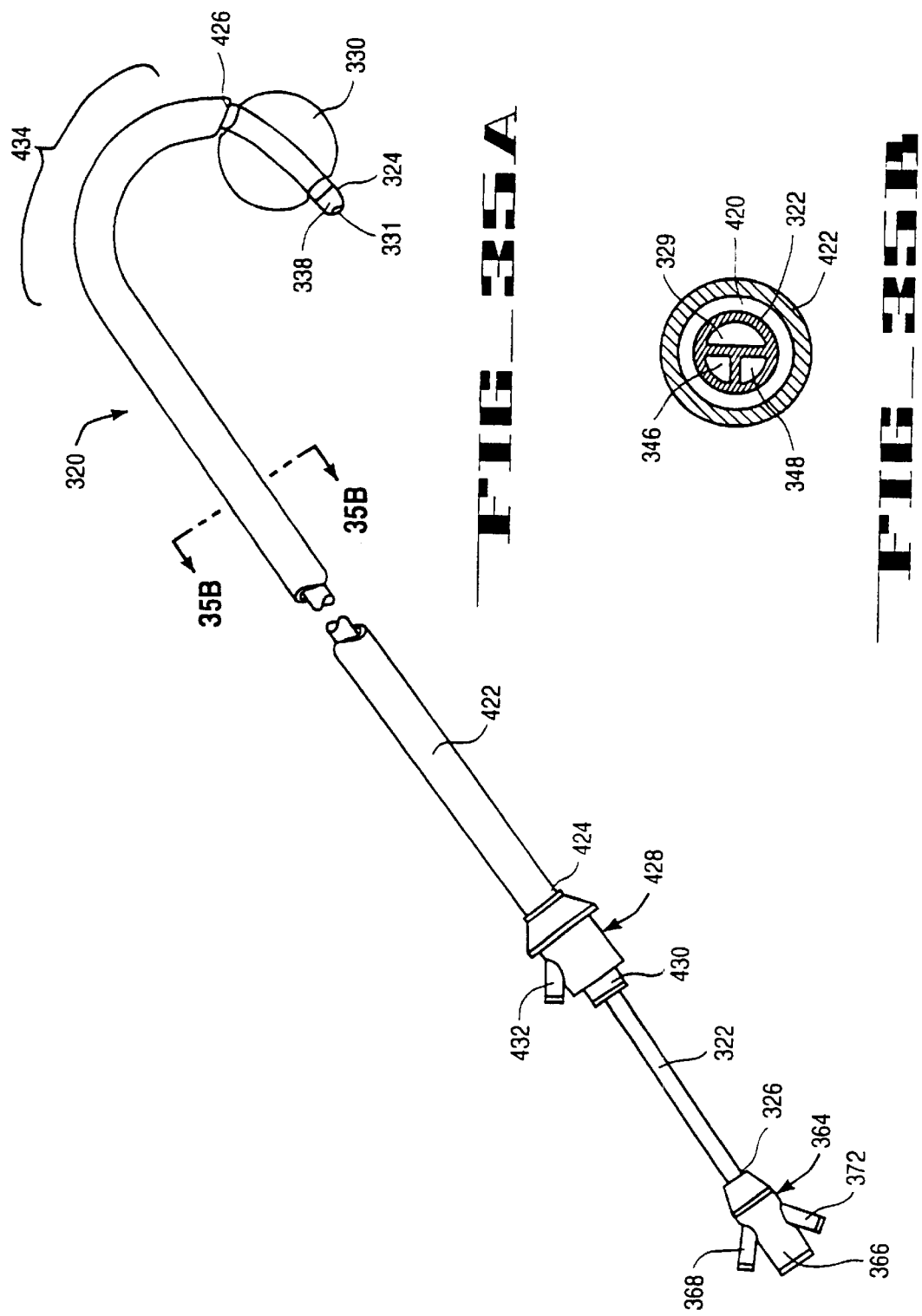
FIG_35A
FIG_35B

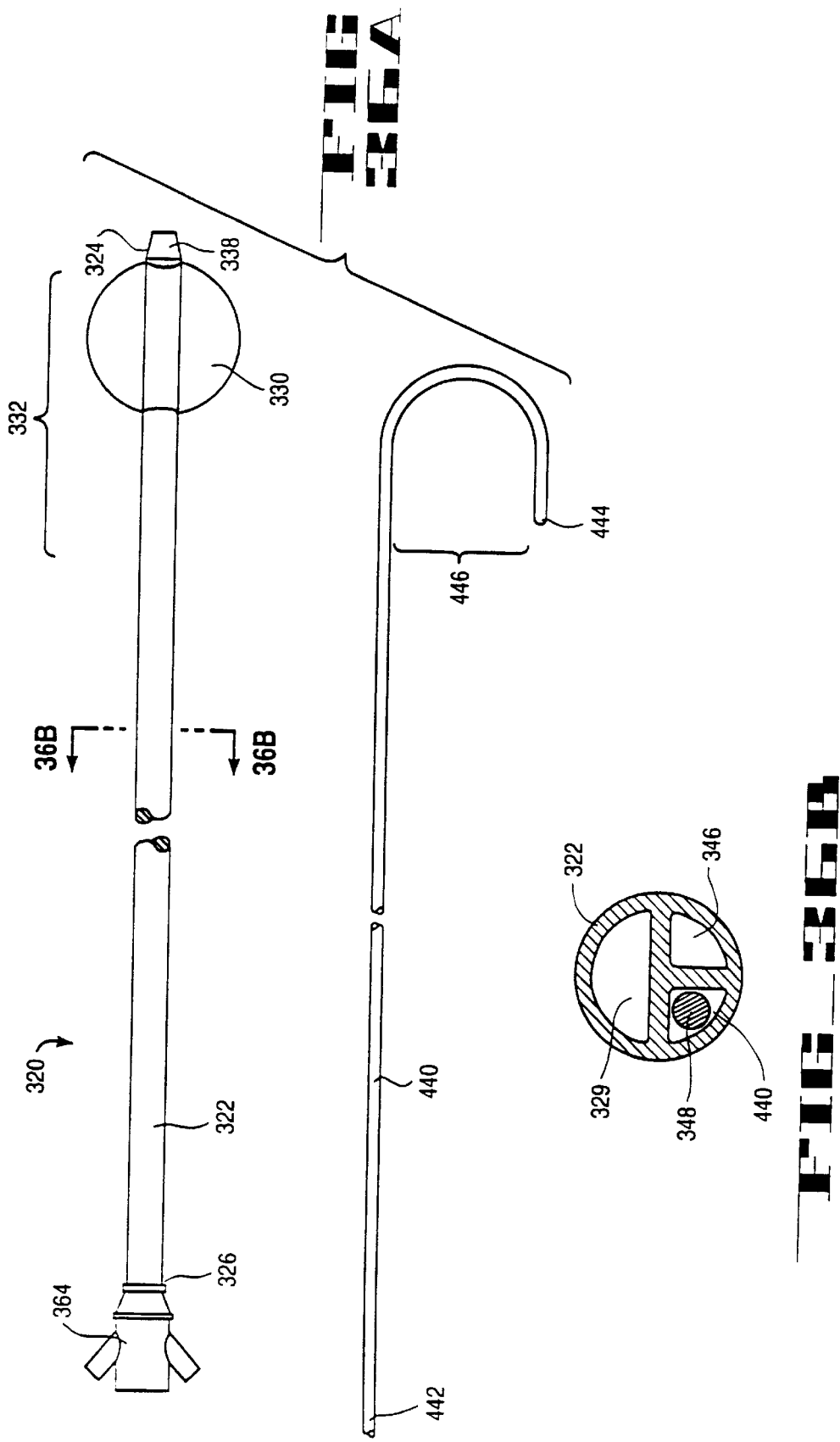
FIG_36A
FIG_36B

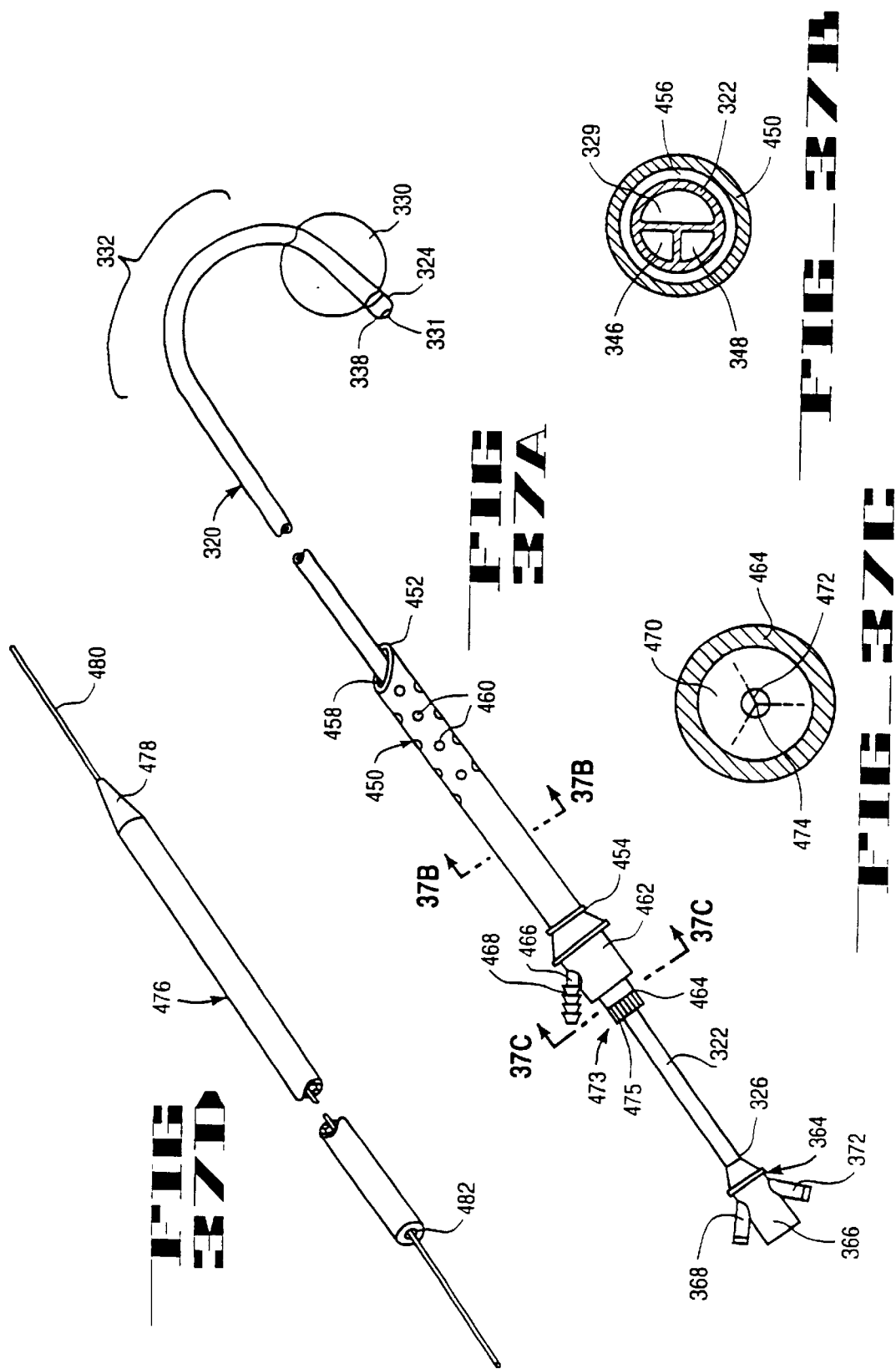

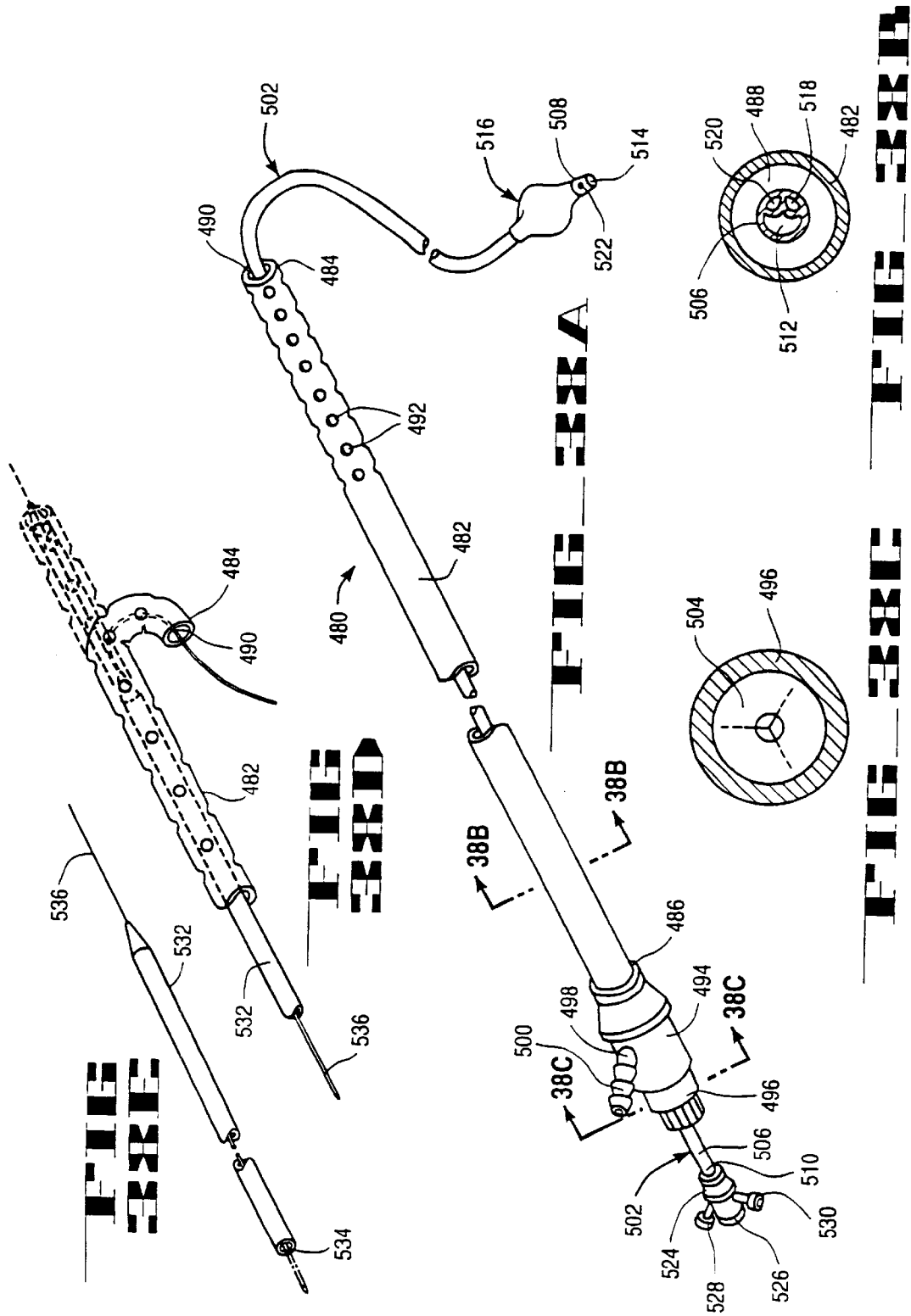

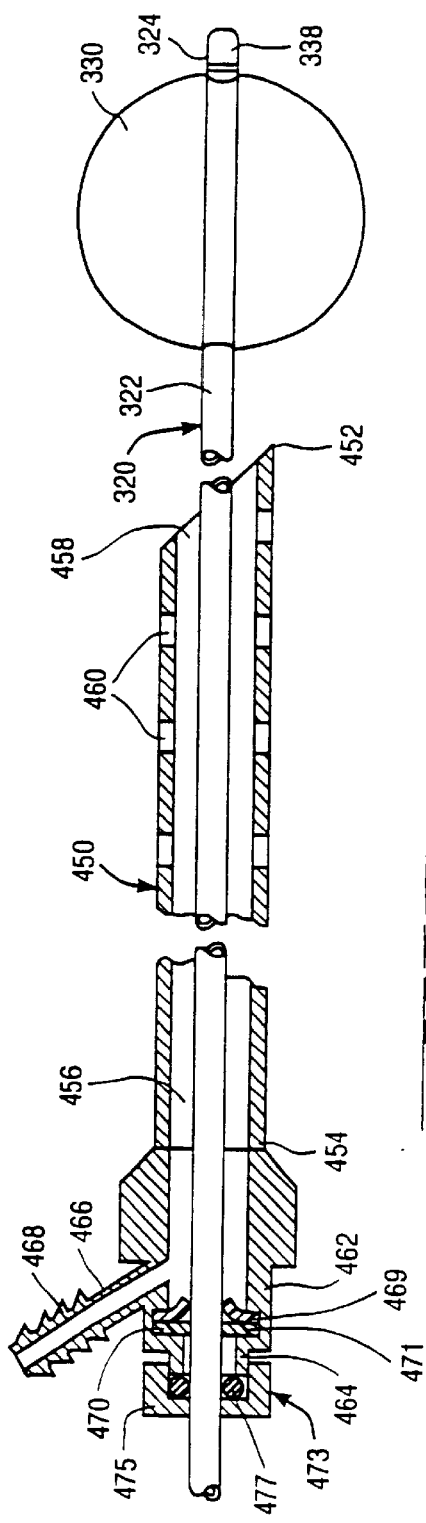
FIG._37E
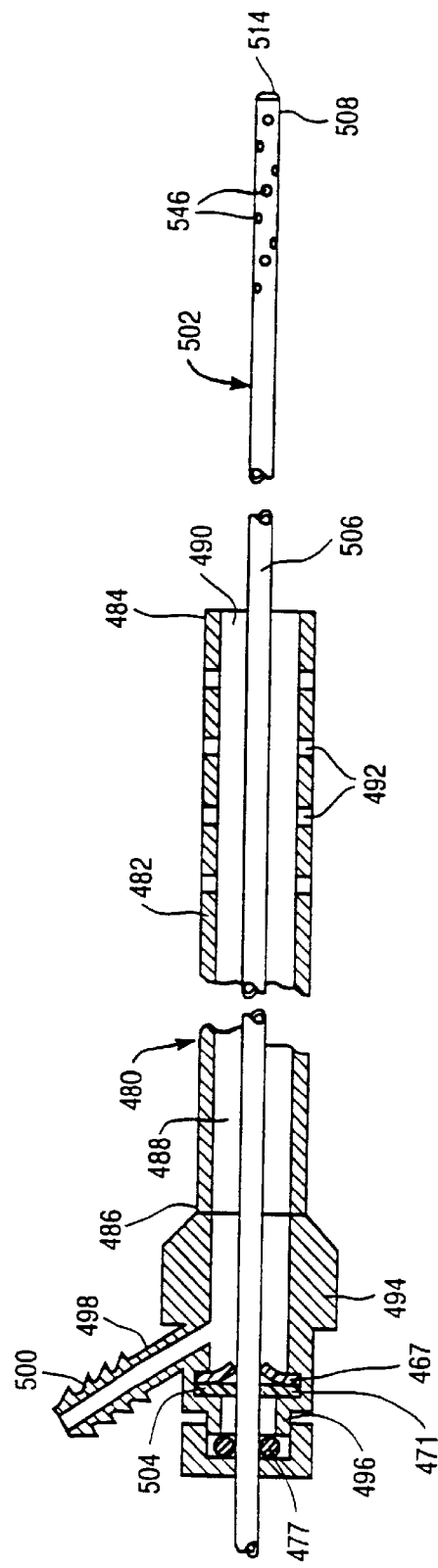
FIG._37F

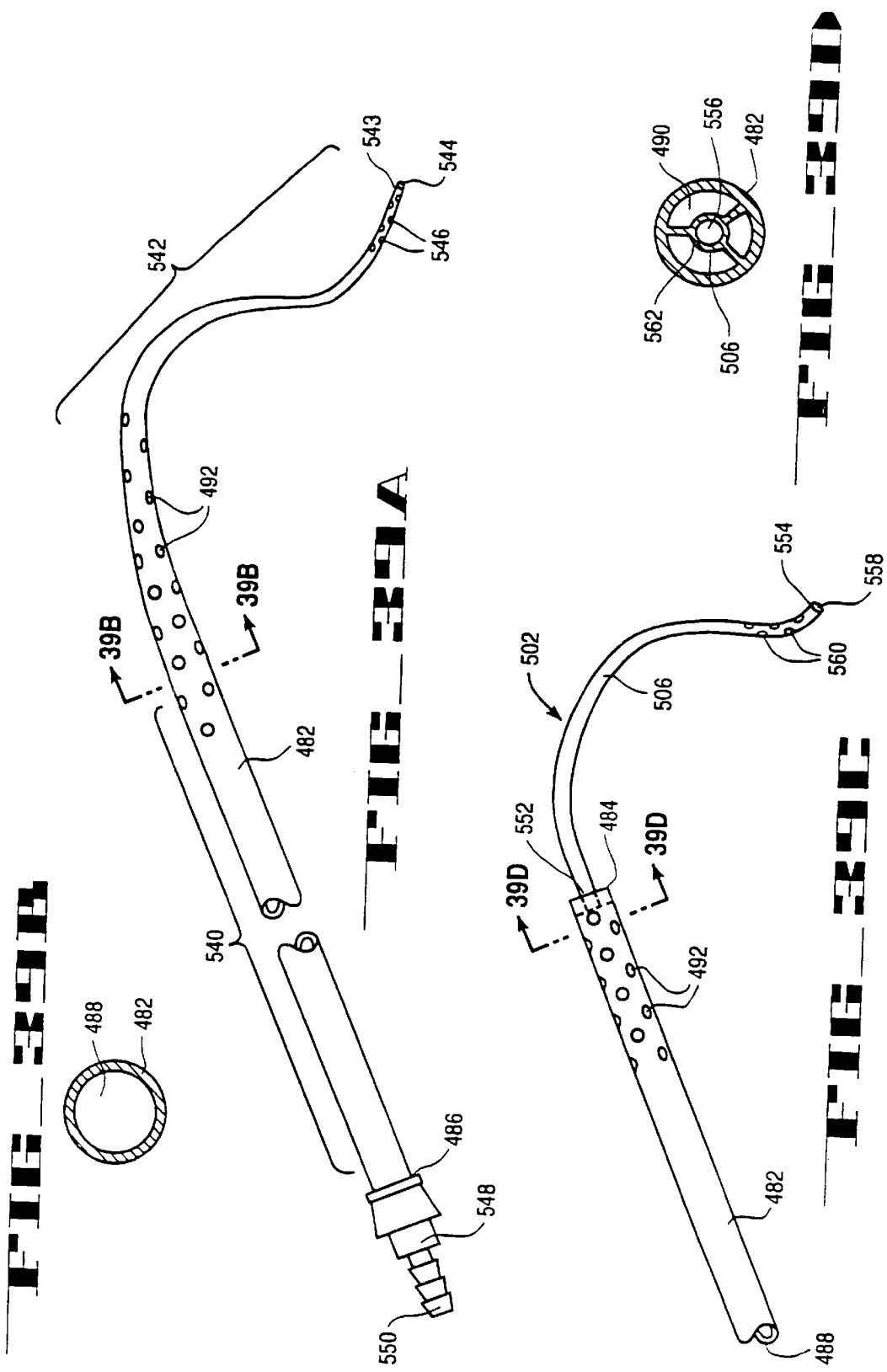

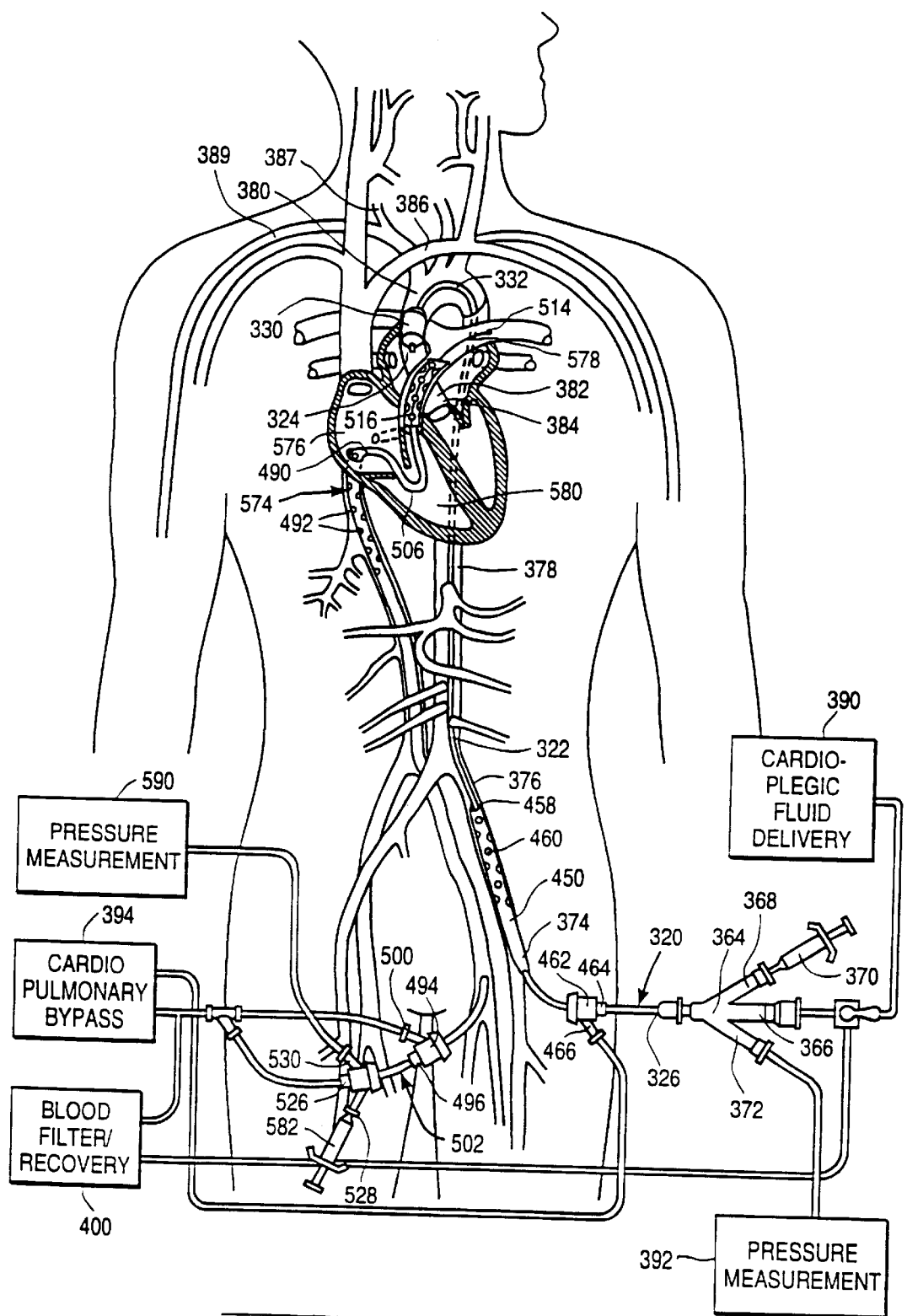
FIG_40

ENDOVACULAR CARDIAC VENTING CATHETER AND METHOD

CROSS-REFERENCE TO RELATED APPLICATIONS

This application is a continuation of U,S. patent application Ser. No. 08/694,916, now U.S. Pat. No. 5,916,183, filed Nov. 30, 1996, which is a divisional of application Ser. No. 08/415,238, filed Mar. 30, 1995, now abandoned, which is a continuation-in-part of application Ser. No. 08/282,192, filed Jul. 28, 1994, now issued as U.S. Pat. No. 5,584,803, which is a continuation-in-part of application Ser. No. 08/162,742, filed Dec. 3, 1993, now abandoned, which is a continuation-in-part of application Ser. No. 08/123,411, filed Sep. 17, 1993, now abandoned, which is a continuation-in-part of application Ser. No. 07/991,188, filed Dec. 15, 1992, now abandoned, which is a continuation-in-part of application Ser. No. 07/730,559, filed Jul. 16, 1991, now issued as U.S. Pat. No. 5,370,685. The complete disclosures of all of these applications are hereby incorporated herein by reference for all purposes.

FIELD OF THE INVENTION

This invention relates generally to devices and methods for performing cardiovascular, pulmonary and neurosurgical procedures wherein the patient is placed on cardiopulmonary bypass. More specifically, the invention relates to devices and methods for venting blood and other fluids from the heart while the heart is under cardioplegic arrest and the patient is on cardiopulmonary bypass.

BACKGROUND OF THE INVENTION

Various cardiovascular, neurosurgical, pulmonary and other interventional procedures, including repair or replacement of aortic, mitral and other heart valves, repair of septal defects, pulmonary thrombectomy, coronary artery bypass grafting, treatment of aneurysms, and neurovascular procedures, may require general anesthesia, cardiopulmonary bypass, and arrest of cardiac function. In order to arrest cardiac function, the heart and coronary blood vessels must be isolated from the remainder of the circulatory system. Using current techniques, isolation of the heart and coronary blood vessels is accomplished by placing a mechanical cross-clamp externally on the ascending aorta downstream of the ostia of the coronary arteries, but upstream of the brachiocephalic artery. A catheter is then inserted directly into the ascending aorta between the cross-clamp and the aortic valve, and cardioplegic fluid is infused through the catheter into the ascending aorta from which it flows into the coronary arteries to perfuse the myocardium. An additional catheter may be introduced into the coronary sinus for retrograde perfusion of the myocardium with cardioplegic fluid. In addition, the myocardium is usually cooled by irrigating with cold saline solution and/or application of ice or cold packs to the heart. Cardiac contractions will then cease.

While the heart is stopped, circulation is maintained throughout the body by a cardiopulmonary bypass system. A venous cannula is placed in a major vein such as the inferior vena cava in order to withdraw deoxygenated blood from the body. The deoxygenated blood is directed to a blood oxygenator which restores the blood with oxygen, and the oxygenated blood is pumped back into a major artery downstream of the aortic cross-clamp through an arterial return cannula.

Although the patient is on cardiopulmonary bypass, a certain amount of blood not withdrawn through the venous cannula returns through the venous system to the heart. In addition, cardioplegic fluid delivered into the coronary arteries drains back into the heart through the coronary sinus. Therefore, the heart must be vented to prevent an excessive quantity of blood and other fluids from pooling in the heart while it is not beating. To accomplish this, a venting cannula may be introduced through the aortic wall into the aorta upstream of the cross-clamp to withdraw fluid from the aortic root. Alternatively, a venting cannula may be introduced through a wall of the pulmonary artery near the point at which it connects to the right ventricle of the heart to allow blood to be withdrawn from the pulmonary artery. In procedures in which the heart itself is surgically opened, a venting cannula may be introduced directly into the heart through the incision in the heart wall.

Known techniques for performing major surgeries such as coronary artery bypass grafting and heart valve repair and replacement have generally required open access to the thoracic cavity through a large open wound, known as a thoracotomy. Typically, the sternum is cut longitudinally (a median sternotomy), providing access between opposing halves of the anterior portion of the rib cage to the heart and other thoracic vessels and organs. An alternate method of entering the chest is via a lateral thoracotomy, in which an incision, typically 10 cm to 20 cm in length, is made between two ribs. A portion of one or more ribs may be permanently removed to optimize access.

In procedures requiring a median sternotomy or other type of thoracotomy, the ascending aorta is readily accessible for placement of an external cross-clamp, and for introduction of a cardioplegic fluid delivery cannula and venting cannula through the aortic wall. The pulmonary artery is exposed as well to allow introduction of a venting catheter through the pulmonary arterial wall. However, such surgery often entails weeks of hospitalization and months of recuperation time, in addition to the pain and trauma suffered by the patient. Moreover, while the average mortality rate associated with this type of procedure is about two to fifteen per cent for first-time surgery, mortality and morbidity are significantly increased for reoperation. Further, significant complications may result from such procedures. For example, application of an external cross-clamp to a calcified or atheromatous aorta may cause the of release of emboli into the brachiocephalic, carotid or subclavian arteries with serious consequences such as strokes.

Methods and devices are therefore needed for isolating the heart and coronary arteries from the remainder of the arterial system, arresting cardiac function, venting the heart, and establishing cardiopulmonary bypass without the open-chest access provided by a median sternotomy or other type of thoracotomy. In particular, methods and devices are needed which facilitate venting the heart sufficiently to allow the heart to be placed under cardioplegic arrest with full cardiopulmonary bypass, without requiring open-chest access to the heart and without requiring an incision or puncture in the aorta, in the pulmonary artery, or in the heart wall.

The descriptive terms downstream and upstream, when used herein in relation to the patient's vasculature, refer to the direction of blood flow and the direction opposite that of blood flow, respectively. In the arterial system, downstream refers to the direction further from the heart, while upstream refers to the direction closer to the heart, with the opposite true in the venous system. The terms proximal and distal, when used herein in relation to instruments used in the procedure, refer to directions closer to and farther away from the operator performing the procedure.

SUMMARY OF THE INVENTION

The present invention is directed to an endovascular approach for preparing a patient's heart for cardiac procedures which does not require a grossly invasive thoracotomy. The invention facilitates venting fluids from a patient's heart while the heart is placed under cardioplegic arrest and circulation is maintained by a cardiopulmonary bypass system without necessitating a median sternotomy or other thoracic incision and without requiring punctures or incisions in the heart, aorta, pulmonary artery, or other vessels.

In a first aspect of the invention, a venting catheter is provided for withdrawing blood from a pulmonary artery connected to a right ventricle of a patient's heart. The venting catheter comprises a flexible elongate shaft having a distal end, a proximal end, and an inner lumen extending from the proximal end to an inlet port at the distal end. Usually, a plurality of inlet ports are provided at the distal end in communication with the inner lumen. The shaft has a length selected to allow the distal end to be positioned in the pulmonary artery with the proximal end extending transluminally to a peripheral vein and out of the patient through a puncture in the peripheral vein. Usually, the shaft is at least about 40 cm in length to allow the venting catheter to be introduced into the internal jugular vein in the neck and advanced into the pulmonary artery via the superior vena cava. The inner lumen is configured to allow blood to be withdrawn from the pulmonary artery at a rate of at least 50 ml/min. at a pressure no lower than −350 mmHg. In a specific embodiment, the inner lumen has cross-sectional area of at least 4.0 mm$^2$.

In a preferred embodiment, the venting catheter may include an expandable member mounted to the shaft near the distal end. The expandable member may serve several purposes. The expandable member may be configured to be carried by blood flow through the heart into the pulmonary artery. In addition, the expandable member may be configured to occlude the pulmonary artery when expanded. Usually, the expandable member comprises a balloon, and the shaft has an inflation lumen extending from the proximal end to an opening near the distal end in communication with the interior of the balloon. Alternatively, the expandable member comprises an expandable frame to which a flow resistant membrane is mounted. The expandable frame may include a plurality of flexible beams mounted longitudinally to the shaft and configured to deflect outwardly when under compression. The flow-resistant membrane may comprise an elastomeric web between the flexible beams.

The venting catheter may also include means for measuring pressure in the pulmonary artery. The pressure measurement means may comprise a pressure lumen extending through the shaft from the proximal end to a pressure port near the distal end.

The shaft of the venting catheter may have a proximal portion which defines a longitudinal axis, and a distal portion which is disposed at an angle of less than about 120°, and usually less than about 90°, relative to the longitudinal axis. This facilitates placement of the distal end in the pulmonary artery when introducing the catheter transluminally from a peripheral vein into the heart. In a preferred embodiment, the distal portion is disposed at an angle about 50°–60° relative to the proximal portion, facilitating placement of the distal end in the pulmonary artery when the venting catheter is introduced into the heart via the superior vena cava.

The venting catheter may be used as part of a system for venting blood from the heart during cardiac procedures involving cardiopulmonary bypass. In addition to the venting catheter, such a system according to the invention includes flow-directed means for guiding the distal end of the shaft into the pulmonary artery from the right ventricle, and pump means in communication with inner lumen at the proximal end of the shaft for withdrawing blood from the pulmonary artery through the inner lumen at a rate of at least 50 m/min at a pressure no lower than −350 mmHg.

The flow-directed means may comprise either an integral part of the venting catheter itself, or a separate device. In one embodiment, the flow-directed means comprises an expandable member mounted near the distal end of the venting catheter which floats with blood flow through the right side of the heart into the pulmonary artery. Alternatively, the flow-directed means may be a separate flow directed catheter such as a Swan-Ganz catheter or wedge pressure catheter which has a small-diameter flexible shaft with a balloon mounted to its distal end. The flow-directed catheter is first positioned in the inner lumen of the venting catheter and advanced so that the distal end of the flow-directed catheter is distal to the venting catheter. The flow-directed catheter is then introduced into a peripheral vein such as an internal jugular vein, advanced into the right atrium, and its balloon then inflated. The inflated balloon will be guided into the right ventricle and into the pulmonary artery by the flow of blood through the heart. The venting catheter is then slidably advanced over the flow-directed catheter until the distal end is positioned in the pulmonary artery. The flow-directed catheter is then removed from the patient.

The pump means of the system may comprise any of various types of blood pumps utilized in medical procedures. For example, the pump may be a centrifugal pump or roller pump of the type utilized in cardiopulmonary bypass systems. In a preferred embodiment, the pump means is part of a cardiopulmonary bypass system configured to receive blood from the inner lumen of the venting catheter as well as deoxygenated blood withdrawn from the venous system of the patient, oxygenate the blood, and return the blood to an artery in the patient. The cardiopulmonary bypass system is preferably configured for connection to peripheral vessels in the patient, and includes a venous cannula suitable for introduction in a peripheral vein such as a femoral vein, and an arterial return cannula suitable for introduction in a peripheral artery such as a femoral artery.

In order to facilitate inducing cardioplegic arrest, the system of the invention may further include means for arresting the patient's heart. The means for arresting the heart preferably includes means for occluding the lumen of the patient's aorta between the coronary ostia and the brachiocephalic artery. In a particular embodiment, the occlusion means comprises an aortic catheter introduced through a peripheral artery into the aorta. The aortic catheter has a balloon on its distal end which, when expanded, occludes the aortic lumen. The aortic catheter also includes an inner lumen which opens at a port distal to the balloon to allow a cardioplegic fluid such as cold aqueous potassium chloride mixed with blood to be delivered through the inner lumen into the aortic root, from which the fluid flows into the coronary arteries. By isolating the coronary arteries from the arterial system and delivering cardioplegic fluid, heart contractions will quickly cease, with the patient's circulation maintained by the cardiopulmonary bypass system. While the heart is stopped, blood and other fluids are withdrawn from within the heart by the venting catheter positioned in the pulmonary artery.

In a further aspect of the invention, a method of venting blood from a patient's heart comprises the steps of:

introducing a venting catheter into a peripheral vein;

advancing the venting catheter through the peripheral vein and into a right ventricle of the patient's heart;

positioning a distal end of the venting catheter in a pulmonary artery leading away from the right ventricle; and withdrawing blood from the pulmonary artery through an inner lumen in the venting catheter.

Usually, the peripheral vein into which the venting catheter is introduced comprises the internal jugular vein which can be accessed percutaneously or by surgical cut-down in the patient's neck. Alternatively, the peripheral vein could be a right subclavian vein, also in the patient's neck, a femoral vein, accessible in the patient's groin, or other peripheral vein of suitable size and location to allow the venting catheter to be positioned intraluminally and advanced into the heart via the inferior vena cava or superior vena cava.

In a preferred embodiment, blood is withdrawn from the pulmonary artery at a rate of at least 50 ml/min at a pressure no lower than −350 mmHg. This facilitates venting the heart at a sufficient rate to keep excessive quantities of blood from pooling in the heart, while keeping pressure at a level which will not cause undue hemolysis.

In one embodiment, the step of positioning comprises introducing a flow-directed catheter into the peripheral vein before the step of introducing the venting catheter. The flow-directed catheter is advanced through the peripheral vein and into the patient's heart. An expandable member on the distal end of the flow-directed catheter is then expanded so that the expanded flow directed catheter is carried by blood flow through the heart into the pulmonary artery. The flow-directed catheter is positioned in the inner lumen of the venting catheter, and the venting catheter is slidably advanced over the flow-directed catheter into the pulmonary artery. In an alternative embodiment, the step of positioning comprises expanding an expandable member on the distal end of the venting catheter, the expanded expandable member being carried by blood flow through the heart into the pulmonary artery.

The method may further include a step of measuring pressure in the pulmonary artery through a pressure lumen in the venting catheter or by other pressure measurement means at the distal end of the venting catheter.

In addition, the pulmonary artery may be occluded by an occluding member on the distal end of the venting catheter while withdrawing blood therefrom.

The method will usually include a step of arresting the heart, wherein the coronary arteries are isolated from the remainder of the arterial system, and a cardioplegic fluid is delivered into the coronary arteries to perfuse the myocardium to arrest cardiac function. Preferably, this is accomplished by means of the above-described aortic occlusion catheter. When the heart is stopped, circulation is maintained by a cardiopulmonary bypass system which removes deoxygenated blood from a peripheral vein in the patient, oxygenates the withdrawn blood, and returns the oxygenated blood to a peripheral artery in the patient.

Using the system and method of the invention, a patient's heart can be arrested and the patient placed on cardiopulmonary bypass without a thoracotomy, thereby reducing mortality and morbidity, decreasing patient suffering, reducing hospitalization and recovery time, and lowering medical costs relative to previous open-chest procedures. The venting catheter of the invention facilitates venting of blood and other fluids from the heart while the heart is under cardioplegic arrest and the patient is supported on cardiopulmonary bypass, without need for a open-chest access and without need for a puncture or incision in the aorta, in the pulmonary artery, or in the heart itself.

With the venting catheter in place, the heart arrested and cardiopulmonary bypass established, the patient is prepared for a variety of surgical and diagnostic procedures, including repair or replacement of aortic, mitral and other heart valves, repair of septal defects, pulmonary thrombectomy, coronary artery bypass grafting, angioplasty, atherectomy, electrophysiological mapping and ablation, treatment of aneurysms, transmyocardial revascularization, as well as neurovascular and neurosurgical procedures. While such procedures may be performed through a thoracotomy in the conventional manner, the invention provides the capability for performing procedures such as heart valve replacement or coronary artery bypass grafting using minimally-invasive techniques, either by means of surgical instruments introduced endovascularly through an artery or vein, or by means of thoracoscopic instruments introduced through small incisions in the chest wall.

Moreover, as mentioned, the system may even be employed in conventional open-heart procedures. These and other advantages of the invention will become more apparent from the following detailed description of the invention when taken in conjunction with the accompanying exemplary drawings.

BRIEF DESCRIPTION OF THE DRAWINGS

FIG. 1 schematically illustrates a cardiac access system embodying features of the invention.

FIG. 2 is an enlarged view, partially in section, of the occluding catheter shown in FIG. 1 disposed within the ascending aorta.

FIG. 3 is a transverse cross-sectional view of the occluding catheter shown in FIG. 2 taken along the lines 3—3.

FIG. 4 is an enlarged view, partially in section, of the retrograde cardioplegia delivery catheter and the pulmonary venting catheter shown in FIG. 1.

FIG. 4A is a side elevational view of a venting catheter constructed in accordance with the principles of the invention.

FIG. 4B is a side view of a distal portion of the venting catheter of FIG. 4A.

FIG. 4C is a transverse cross-section of the venting catheter of FIG. 4A taken through line 4C—4C.

FIG. 4D is a side view of a distal portion of a flow-directed venting catheter constructed according to the invention.

FIGS. 4E–4F are transverse cross-sections of the flow-directed venting catheter of FIG. 4D taken through lines 4E—4E and 4F—4F, respectively.

FIG. 4G is a side view of a distal portion of a flow-directed venting catheter according to the invention illustrating an alternative embodiment of an expandable member for being carried by blood flow through the heart.

FIGS. 4H, 4J, and 4L are side cross-sectional views of alternative embodiments of a flow-directed venting catheter according to the invention.

FIGS. 4I, 4K, and 4M are transverse cross-sections of the flow-directed venting catheters of FIGS. 4H, 4J, and 4L, respectively, taken through lines 4I—4I, 4K—4K, and 4M—4M, respectively.

FIG. 7 schematically illustrates securing a mounting skirt on the prosthetic valve to the wall of the ascending aorta.

FIG. 8 schematically illustrates securing the upper extensions of the valve to the aortic wall.

FIG. 9 schematically illustrates an alternate means for removing a heart valve.

FIG. 10 is an enlarged perspective view of the cutting member of the catheter shown in FIG. 9.

FIG. 11 schematically illustrates another alternate means for removing a heart valve.

FIGS. 12 and 13 schematically illustrate an alternate embodiment of a valve introducing device and the method of discharging a prosthetic or replacement valve.

FIG. 14 schematically represents in an elevational view a prosthetic heart valve.

FIG. 15 is a top view of the prosthetic heart valve shown in FIG. 14.

FIG. 16 is a schematic partly cut-away representation of a patient's heart having percutaneous catheters placed therein for carrying out the method according to the present invention;

FIG. 17 is a similar view to FIG. 1 showing the aortic catheter in position but including an angioscope and a left ventricular venting cannula introduced into the aortic root and left ventricle respectively, via separate lumina within the aortic catheter;

FIG. 18 is a front elevational view of part of the vascular system of a patient showing, inter alia, the aortic balloon catheter positioned in the ascending aorta via and femoral artery;

FIG. 19 is a side elevational view of the control end of the aortic catheter according to the present invention;

FIG. 20 is a partly cut away side elevational view of the balloon end of the catheter of FIG. 19 in an inflated condition;

FIG. 21a is a cross-sectional view of the catheter of FIG. 19 intermediate the control end and the balloon end;

FIG. 21b is an alternative cross-sectional arrangement of the lumina in the catheter of FIG. 19;

FIG. 22 is a cross-sectional view through the balloon end of the catheter of FIG. 19;

FIG. 25 is a side elevational view of an endovascular device for partitioning the ascending aorta between the coronary ostia and brachiocephalic artery constructed in accordance with the principles of the present invention.

FIG. 25A is an end view of a distal portion of the device of FIG. 25 illustrating the skew of the shaped distal portion.

FIGS. 25B and 25C are side elevational views showing alternative embodiments of the shaped distal portion of the device of FIG. 25.

FIG. 26A is a perspective view of a distal portion of the device of FIG. 25 in a first embodiment thereof.

FIG. 26B is a perspective view of a distal portion of the device of FIG. 25 in a second embodiment thereof.

FIG. 31 is a front view of a portion of a patient's arterial system illustrating the introduction and advancement of the device of FIG. 25 in the femoral artery, iliac artery and aorta.

FIG. 32 schematically illustrates a system for arresting the heart constructed in accordance with the principles of the present invention, wherein the device of FIG. 25 is positioned in the ascending aorta with cardioplegic fluid delivery means connected to the proximal end and a cardiopulmonary bypass system connected to the patient.

FIG. 33 illustrates the distal portion of the device of FIG. 25 positioned in the ascending aorta with the occluding means expanded and a tissue cutting device extended from the distal end.

FIGS. 34A–34B are side and transverse cross-sections, respectively, of an alternative embodiment of an endovascular partitioning device constructed in accordance with the principles of the present invention.

FIGS. 35A–35B are side elevational and transverse cross-sectional views, respectively, of a further alternative embodiment of an endovascular partitioning device constructed in accordance with the principles of the present invention.

FIG. 36A is a side elevational view of still another embodiment of an endovascular partitioning device constructed in accordance with the principles of the invention.

FIG. 36B is a transverse cross section taken along the line 36B—36B in FIG. 36A, showing a shaping element positioned in an inner lumen in the shaft.

FIG. 37A is a side elevational view of a further alternative embodiment of an endovascular partitioning device constructed in accordance with the principles of the present invention.

FIG. 37B is a transverse cross-section taken through line 37B—37B in FIG. 37A.

FIG. 37C is a transverse cross-section taken through line 37C—37C in FIG. 37A, showing a hemostasis valve with the aortic occlusion catheter removed from the blood flow lumen in the bypass cannula in the device of FIG. 37A.

FIG. 37D is a perspective view of an obturator and guidewire for use with the infusion tube in the device of FIG. 37A.

FIG. 37E is a side cross-sectional view of the partitioning device of FIG. 37A.

FIG. 38A is a perspective view of a cardiac venting device constructed in accordance with the principles of the present invention FIG. 38B is a transverse cross-section taken through line 38B—38B in FIG. 38A.

FIG. 38C is a transverse cross-section taken through line 38C—38C in FIG. 38A, showing the hemostasis valve with the venting catheter removed from blood flow lumen of the bypass cannula.

FIG. 38D is a perspective view of an alternative configuration of a distal portion of the device of FIG. 38A.

FIG. 38E is a perspective view of an obturator to facilitate introduction of the device of FIG. 38A.

FIG. 38F is a side cross-sectional view of the cardiac venting device of FIG. 38A.

FIG. 39A is side elevational view of a further embodiment of the cardiac venting device of the present invention.

FIG. 39B is a transverse cross-section taken through line 39B—39B in FIG. 39A.

FIG. 39C is a side elevational view of an alternative configuration of a distal portion of the device of FIG. 39A.

FIG. 39D is transverse cross-section taken through line 39D—39D in FIG. 39C.

FIG. 40 is a front partial cut-away view of a patient's body showing the positioning of the aortic partitioning device and cardiac venting device in accordance with the method of the present invention.

DETAILED DESCRIPTION OF THE INVENTION

Figure 6:
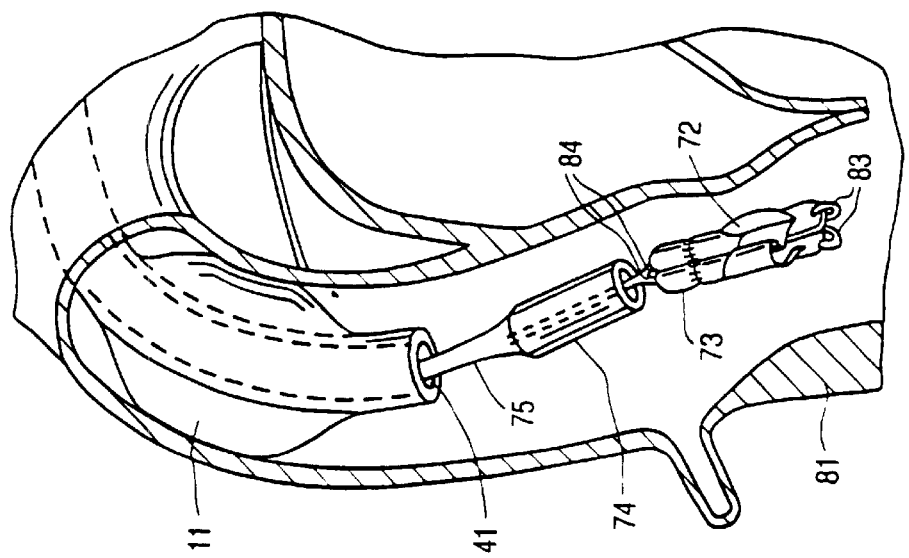
FIG. 6 schematically illustrates the introduction of a prosthetic valve into the region of the ascending aorta from which the original heart valve had been removed.

The invention provides a cardiac access system including an endovascular device for partitioning the ascending aorta, as well as a system for selectively arresting the heart, which are useful in performing a variety of cardiovascular, pulmonary, neurosurgical, and other procedures. The procedures with which the invention will find use include repair or replacement of aortic, mitral, and other heart valves, repair of septal defects, pulmonary thrombectomy, electrophysiological mapping and ablation, coronary artery bypass grafting, angioplasty, atherectomy, treatment of aneurysms, myocardial drilling and revascularization, as well as neurovascular and neurosurgical procedures. The invention is especially useful in conjunction with minimally-invasive cardiac procedures, in that it allows the heart to be arrested and the patient to be placed on cardiopulmonary bypass using only endovascular devices, obviating the need for a thoracotomy or other large incision. Moreover, even in conventional open-chest procedures, the endovascular aortic partitioning device of the invention will frequently find use where an external cross-clamp would raise substantial risks of embolus release due to calcification or other aortic conditions.

Reference is made to FIG. 1 which schematically illustrates the overall cardiac accessing system of the invention and the individual components thereof. The accessing system includes an elongated aortic occlusion or delivery catheter 10 which has an expandable member 11 on a distal portion of the catheter which, when inflated as shown, occludes the ascending aorta 12 to separate the left ventricle 13 and upstream portion of the ascending aorta from the rest of the patient's arterial system and securely positions the distal end of the catheter within the ascending aorta. A cardiopulmonary by-pass system 18 removes venous blood from the femoral vein 16 through the blood withdrawal catheter 17 as shown, removes $CO_2$ from the blood, oxygenates the blood, and then returns the oxygenated blood to the patient's femoral artery 15 through the return catheter 19 at sufficient pressure so as to flow throughout the patient's arterial system except for the portion blocked by the expanded occluding member 11 on the aortic occluding catheter 10. A retrograde cardioplegia balloon catheter 20 is disposed within the patient's venous system with the distal end of the catheter extending into the coronary sinus 21 (shown in FIG. 4) to deliver a fluid containing cardioplegic agents to the myocardium in a retrograde manner through the patient's coronary venous system to paralyze the entire myocardium.

The elongated occluding catheter 10 extends through the descending aorta to the left femoral artery 23 and out of the patient through a cut down 24. The proximal extremity 25 of the catheter 10 which extends out of the patient is provided with a multi-arm adapter 26 with one arm 27 adapted to receive an inflation device 28. The adapter 26 is also provided with a second arm 30 with main access port 31 through which passes instruments, a valve prosthesis, an angioscope, irrigation fluid and the like. A third arm 32 connected to by-pass line 33 is provided to direct blood, irrigation fluid, and the like to or from the system. A suitable valve 34 is provided to open and close the by-pass line 33 and direct the fluid passing through the by-pass line to a discharge line 35 or a line 36 to a blood filter and recovery unit 37. A return line may be provided to return any filtered blood, which will be described hereinafter, to the cardiopulmonary by-pass system 18 or other blood conservation system.

The details of the aortic occlusion catheter 10 and the disposition of the distal extremity thereof within the aorta are best illustrated in FIGS. 2 and 3. As indicated, the catheter 10 includes an elongated catheter shaft 39 which has a first inner lumen 40 in fluid communication with the main access port 31 in the second arm of the adapter 26 and is adapted to facilitate the passage of instruments, a valve prosthesis, an angioscope, irrigation fluid, and the like therethrough and out the distal port 41 in the distal end thereof. A supporting coil 42 may be provided in the distal portion of the first inner lumen 40 to prevent the catheter shaft 39 from kinking as it is advanced through the aortic arch. The shaft 39 is also provided with a second inner lumen 43 which is in fluid communication with the interior of the occluding balloon 11.

A retrograde cardioplegia balloon catheter 20, which is shown in more detail in FIG. 4, is introduced into the patient's venous system through the right internal jugular vein 44 and is advanced through the right atrium 45 and into the coronary sinus 21 through the coronary sinus discharge opening 46 in the right atrium. The retrograde catheter 20 is provided with a balloon 47 on a distal portion of the catheter 20 which is adapted to occlude the coronary sinus 21 when inflated. A liquid containing a cardioplegic agent, e.g. an aqueous KCl solution, is introduced into the proximal end 48 of the catheter 20, which extends outside of the patient, under sufficient pressure so that the fluid containing the cardioplegic agent can be forced to pass through the coronary sinus 21, through the capillary beds (not shown) in the patient's myocardium, through the coronary arteries 50 and 51 and ostia 52 and 53 associated with the respective coronary arteries into the blocked off portion of the ascending aorta 12 as shown.

A pulmonary venting catheter 54 is also shown in FIG. 4 disposed within the right internal jugular vein 44 and extending through the right atrium 45 and right ventricle 55 into the pulmonary trunk 56. The catheter 54 passes through tricuspid valve 57 and pulmonary valve 58. An inflatable occluding balloon 60 may be provided as shown on a distal portion of the pulmonary venting catheter 54 which is inflated to occlude the pulmonary trunk 56 as shown. The pulmonary venting catheter 54 has a first inner lumen 61 which extends from the distal end of the catheter to the proximal end of the catheter which vents fluid from the pulmonary trunk 56 to outside the patient's body either for discharge or for passage to the blood recovery unit and thereby decompresses the left atrium 14 through the pulmonary capillary beds (not shown). The catheter 54 has a second inner lumen 62 which is adapted to direct inflation fluid to the interior of the inflatable balloon 60.

Two presently preferred embodiments of a pulmonary artery venting catheter according to the invention are illustrated in FIGS. 4A–F. Referring first to the embodiment of FIGS. 4A–C, pulmonary venting catheter 602 includes a flexible shaft 604 having a distal end 606 and a proximal end 608. A delivery lumen 610 extends through shaft 604 from proximal end 608 to distal end 606. A plurality of inlet ports 612 are disposed near distal end 606 and are in communication with delivery lumen 610. An adaptor 613 is mounted to proximal end 608 to facilitate connection of tubing in communication with delivery lumen 610. Adaptor 613 may alternatively be a Y-type adaptor and include a second arm (not pictured) in communication with delivery lumen 610, allowing one arm to be connected to a cardiopulmonary bypass tubing while a second arm (usually that axially aligned with shaft 604) is available for introduction of a flow-directed catheter, as further described below. The second arm, if used, would include a hemostasis valve for preventing outflow of blood from delivery lumen 610 both in the presence and absence of a flow-directed catheter positioned through the arm. In a further alternative configuration, adaptor 613 or shaft 604 includes a bellows-like flexible section (not shown) to allow adaptor 613 to be manipulated into a variety of orientations relative to shaft 604 for more convenient connection of tubing without kinking shaft 604.

A soft tip 614 is mounted to shaft 604 at distal end 606 to minimize trauma to tissue when the venting catheter is being introduced and positioned in the pulmonary artery. Soft tip 614 may be tubular and have a large distal opening in communication with delivery lumen 610 for inflow of blood. Alternatively, soft tip 614 may have a tapered or rounded distal end with a small distal opening just large enough for receiving a guidewire or flow-directed catheter, and a plurality of lateral openings in the form of axial slots or round holes on the side of soft tip 614 in communication with delivery lumen 610. Such lateral inlet holes or slots have the advantage of remaining patent even if the distal end becomes blocked by tissue.

A bend 616 is formed in a distal portion of shaft 604 at an angle α usually in a range of 40° to 90°, and preferably about 50° to 60°, to facilitate placement of distal end 606 in the pulmonary artery when introduced into the heart via one of the vena cavae. A stainless steel coil or braid may be embedded in the wall of shaft 604 to prevent kinking in the tortuous path from the peripheral vessel into the pulmonary artery. Shaft 604 has a total length of 50–80 cm, depending upon into which peripheral vein it will be introduced. For introduction into the right internal jugular vein in the neck, shaft 604 preferably has a total working length of about 40–60 cm, whereas for introduction into a femoral or iliac vein, the working length is about 80 to 120 cm. The distance D from proximal end 608 to bend 616 is about ⅔ to ¾ of the working length of shaft 604. Shaft 604 has an outer diameter OD selected to allow introduction of the venting catheter through a peripheral vein such as an internal jugular vein, usually being less than 12.0 French, preferably 8.0–10.0 French, for percutaneous introduction, and less than 14 French for introduction through a surgical cut-down into the peripheral vein. Shaft 604 may also be tapered in the distal direction. Shaft 604 has a stiffness selected to facilitate endoluminal positioning of the venting catheter into the pulmonary artery from a peripheral vein, preferably having a durometer in a range of 40 to 80 Shore D.

In a preferred embodiment, at least a distal portion of shaft 604 or soft tip 614 is radiopaque to allow visualization of venting catheter 602 by means of fluoroscopy. Radiopaque markers may be applied to shaft 604, or a filler of radiopaque material such as barium sulfate may be added to the polymer used to construct shaft 604.

Delivery lumen 610 is configured to facilitate sufficient venting of blood from the pulmonary artery to maintain a low volume of blood within the heart during cardioplegic arrest and full cardiopulmonary bypass. In order to withdraw blood through delivery lumen 610, a negative pressure is applied to lumen 610 at proximal end 608. This negative pressure must be sufficient to adequately vent the heart, but must not be so low as to cause hemolysis in the blood withdrawn or to cause failures or leaks in the cardiopulmonary bypass circuit connections. It is presently preferred to withdraw blood at a rate of at least 50 ml/min, and usually at least 125 ml/min, to vent the heart sufficiently. At the same time, the pressure of the blood withdrawn through delivery lumen 610, at temperatures ranging from about 4° C. to 40° C., should be no lower than −300 mmHg, and preferably no lower than −150 mmHg, so as to avoid excessive hemolysis and creating other problems in the cardipulmonary bypass circuitry. In an exemplary embodiment, for a venting catheter less than 9.0 French in size, delivery lumen 610 is configured to allow blood to be withdrawn at a rate of at least 125 ml/min, preferably at least 250 ml/min, at −100 mmHg at about 25° C.–40° C. To accomplish this, delivery lumen 610 preferably has a diameter ID of at least about 2.0 mm, and usually about 2.2–3.0 mm, thus having a cross-sectional area of at least about 4.0 mm$^2$, and usually 4.8–9.0 mm$^2$. Delivery lumen 610 may also be lined with a thin layer (e.g. 0.05–0.07 mm thick) of Teflon® (E I. DuPont) (polytetrafluoroethylene) or other lubricious material to reduce friction on blood flowing through it, as well as to reduce friction when positioning over a flow-directed catheter or guidewire (described below). Moreover, delivery lumen 610 may be coated with an antithrombolytic material such as heparin sodium to reduce thrombus formation in the blood withdrawn from the heart.

In the embodiment of FIGS. 4A–4C, venting catheter 602 may be guided into the pulmonary artery by means of a separate flow-directed catheter 615 (shown in phantom) over which venting catheter 602 is slidably advanced. Flow-directed catheter 615 is of a diameter, length, and stiffness suitable to be introduced through delivery lumen 610 of venting catheter 602, into a peripheral vein such as the internal jugular vein, and advanced intraluminally into the heart; flow-directed catheter 615 thus has a length of at least 70 cm and preferably at least 100 cm, an outer diameter of than 8.0 French and preferably less than 7.5 French, and a durometer in a range of 60 to 100 Shore C in at least the distal 20 cm thereof. Flow-directed catheter 615 has an expandable member 617 on its distal end, preferably comprising a small inflatable balloon with an inflated diameter less than about 15 mm. The balloon is inflated by injecting an inflation fluid such as saline through an inflation port 619 at the proximmal end of the flow-directed catheter, which communicates with an inflation lumen extending through the catheter and opens in the interior of the balloon. Alternatively, the flow-directed catheter may have a mechanical expandable member, such as a parachute or umbrella-type mechanism which is automatically expanded by its resistance to the flow of blood in the distal direction along the catheter. The flow-directed catheter preferably also includes a pressure measurement port 621 communicating with a pressure lumen opening at a pressure port 623 distal to expandable member 617 through which wedge pressure in the pulmonary artery may be measured. A second pressure measurement port 625 communicating with a pressure port 627 proximal to expandable member 617 may also be provided. The flow-directed catheter may also include a thermocouple at its distal end and another spaced proximally therefrom which are electrically coupled to electrical connectors at the proximal end of the cather for measuring temperature in the pulmonary artery, thereby allowing the calculation of cardiac output using thermodilution techniques, as described, for example, in U.S. Pat. No. 4,721,115, which is incorporated herein by reference. Suitable flow-directed catheters include the Baxter Edwards 7.5 French Swan-Ganz® Thermodilution Venous Infusion Port Catheter VIP™ (Catalog No. 93A-831H-7.5F, Baxter, Inc., Irvine, Calif.), the Arrow 7 French Wedge Pressure Catheter (Catalog No. AI-07127, Arrow, Inc., Reading, Pa.), and the Cook 6.8 French Flow-Directed Balloon Catheter (Catalog No. PVL6.8-110SGB, Cook Inc., Bloomington, Ind.).

Flow-directed catheter 615 is slidably positioned in delivery lumen 610 of venting catheter 602 and its distal end is extended distally out of a distal inlet port in venting catheter 602. The flow-directed catheter is then introduced into a peripheral vein such as the internal jugular vein in the neck, and advanced into the heart. When in the heart, balloon 617 on the distal end of flow-directed catheter 615 may be inflated and the balloon will be carried by the flow of blood through the right side of the heart into the pulmonary artery. Positioning of flow-directed catheter 615 may be facilitated by monitoring pressure in the pulmonary artery through pressure ports 623, 627. Once flow-directed catheter 615 has been placed, venting catheter 602 may then be slidably advanced over the flow-directed catheter until distal end 606 is positioned in the pulmonary artery. Flow-directed catheter 615 is then removed from delivery lumen 610. Accurate placement may be verified by fluoroscopy or transesophageal echocardiography.

In an alternative embodiment of the venting catheter of the invention, a flow-directing means is provided on the venting catheter itself. FIGS. 4D–4F illustrate a distal portion of a flow-directed venting catheter 620 according to the invention. Flow-directed venting catheter 620 has a flexible shaft 622 having a distal end 624 and a proximal end (not pictured in FIGS. 4D–4F). A delivery lumen 626 extends through shaft 622 from the proximal end to distal end 624. A plurality of inlet ports 628, including a distally-oriented port at distal end 624, are disposed near distal end 624 in communication with delivery lumen 626. A flow-directed extension 630 is fixed to distal end 624 of shaft 622, and comprises a flexible flow-directed shaft 632 having an expandable member 634 mounted near its distal end 636. Flow-directed extension 630 has a length of about 0.5 to 5.0 cm to allow it to be positioned in the pulmonary artery when distal end 624 and inlet ports 628 are within the pulmonary trunk downstream of the pulmonary valve. Flow-directed shaft 632 has a diameter smaller than shaft 622, usually less than 7.5 French and preferably about 6.5 French, and is substantially more flexible than shaft 622, preferably having a durometer in a range of 60 to 100 Shore C. Expandable member 634 preferably comprises an elastomeric balloon. A soft tip 638 is mounted to distal end 636. Several additional lumens extend through shaft 622 and through flow-directed shaft 632. These include an inflation lumen 640 extending to an inflation port 642 in shaft 632 within the interior of balloon 634 to facilitate delivery of an inflation fluid into the balloon. A first pressure lumen 644 extends through shaft 622 and through flow-directed shaft 632 to a first pressure port 646 proximal to balloon 634 for measuring pressure within the pulmonary artery. A second pressure lumen 648 extends through shaft 622 and flow-directed shaft 632 to a second pressure port 650 distal to balloon 634 for measuring wedge pressure in the pulmonary artery distal to the balloon. One or more thermocouples (not shown) may also be provided on flow-directed extension 630 near distal end 636 and/or spaced proximally therefrom to allow measurement of temperatures in the pulmonary artery, the thermocouples being electrically coupled to electrical connectors at the proximal end of venting catheter 620, thereby allowing the calculation of cardiac output by the thermodilution method.

As an alternative to balloon 634 for providing flow-direction of venting catheter 620, a variety of alternative expandable means may be utilized. For example, as illustrated in FIG. 4G, a plurality of flexible beams 652 may be longitudinally mounted to or formed into flow-directed shaft 632, the beams being configured to flex outwardly upon actuation by the user. The beams may be formed to have a shape memory so that they may be restrained into a contracted shape during introduction, then will flex outwardly when unrestrained. Such a mechanism is illustrated in U.S. Pat. No. 4,808,163, which is incorporated herein by reference. Alternatively, a pull-wire 654 may extend slidably through a lumen in shafts 622, 632 and coupled to shaft 632 distally of the beams, whereby exerting tension on the pull wire will flex the beams outwardly. A flexible, flow-resistant or blood-impervious membrane or web 656 of a biocompatible fabric or elastomer may be attached to the beams, so that, when the beams are expanded, the membrane will be carried by blood flow through the heart into the pulmonary artery. Alternatively, a parachute-like or umbrella-type expandable member may be used which is expanded by a pull wire or other mechanical linkage, or which expands automatically by its resistance to blood flowing along the catheter in the distal direction.

In use, flow-directed venting catheter 620 is introduced into a peripheral vein by a percutaneous technique such as the Seldinger technique or by surgical cut-down. Venting catheter 620 is advanced through the peripheral vein and through a vena cava into the right atrium of the heart. Expandable member 634 (e.g. balloon) on the distal end of catheter 620 is then expanded. As the operator pushes distally on the proximal end of the venting catheter, the flow of blood through the right side of the heart will tend to guide the distal tip 636 of the flow-directed extension 630 from the right atrium through the tricuspid valve into the right ventricle, and from the right ventricle through the pulmonary valve into the pulmonary artery. Venting catheter 620 is advanced until distal end 624 and inlet ports 628 are positioned in the pulmonary artery downstream of the pulmonary valve. Pressure monitoring through pressure ports 646, 650 facilitates proper positioning in the pulmonary artery. Accurate placement may be verified by fluoroscopy or by transesophageal echocardiography. Expandable member 634 may then be contracted, or left expanded, as desired.

In a further alternative embodiment, balloon 634 of flow-directed venting catheter 620 may be configured to be inflated by delivery of inflation fluid through delivery lumen 626, rather than requiring a separate inflation lumen, as illustrated in FIGS. 4H–4M. In the embodiments of FIGS. 4H–4K, a one-way valve 660 is included in delivery lumen 626 near distal end 624 proximal to inlet ports 628, configured so that blood flowing into inlet ports 628 in the proximal direction through delivery lumen 626 opens valve 660. One way valve 660 may comprise a plurality of flexible pie-shaped leaflets 662 designed to deflect into delivery lumen 626 under the force of fluid flow through inlet ports 628. Rather than extending through shaft 622 to the proximal end of the venting catheter, inflation lumen 640 extends from inflation port 642 to a point just proximal to valve 660, where inflation lumen 640 opens into delivery lumen 626. In this way, when an inflation fluid is delivered under sufficient pressure in the distal direction through delivery lumen 626, leaflets 662 of valve 660 are urged distally to engage one another, sealing the distal end of delivery lumen 626, thereby diverting the inflation fluid through inflation lumen 640 into the interior of balloon 634. In the embodiment of FIG. 4H, flow-directed extension 630 is of smaller diameter than shaft 622, and valve 660 is mounted within a distal inlet port 664 in communication with delivery lumen 626 at distal end 624. In the embodiment of FIG. 4J, shaft 622 is tapered distally down to the diameter of flow-directed extension 630, and valve 660 is mounted just proximal to a plurality of side inlet ports 666 in communication with delivery lumen 626. Delivery lumen 626 extends through flow-directed extension 630, and has a distal inlet port 667 at the distal end 636. In both cases a pressure lumen 668 may extend from the proximal end of shaft 622 to a pressure port 670 at the distal end of flow-directed shaft 632 for measuring pulmonary artery pressure distal to balloon 634.

In still another embodiment illustrated in FIG. 4K–4L, flow-directed venting catheter 672 includes a balloon 674 mounted over its distal end, the interior of balloon 674 being in communication with a delivery lumen 676 through a distal inflation port 678. A plurality of side inlet ports 680 are provided near the distal end of catheter 672 also in communication with delivery lumen 676. A double-armed adaptor 682 is mounted to the proximal end of catheter 672 and includes an axially-aligned tubular arm 684 and a tubular side arm 686, both in communication with delivery lumen 676. Side arm 686 has a hose barb 688 for attachment of tubing in connection with a cardiopulmonary bypass system. Axial arm 684 has a proximal fitting 690 over which a cap (not shown) may be attached. An internal sheath 692 is slidably positionable within delivery lumen 676 through axial arm 684, and may be advanced distally so as to seal off side inlet ports 680 from delivery lumen 676. Sheath 692 has a distal opening 694 which may be aligned with distal inflation port 678. At its proximal end, sheath 692 has a luer fitting 696 for connection to a syringe or other inflation fluid delivery device (not shown). In this way, inflation fluid may be delivered through sheath 692 into ballon 674 for the inflation thereof, eliminating the need for a separate inflation lumen. Venting catheter 672 may then be intraluminally advanced into the pulmonary artery in the manner described above. After the flow-directed venting catheter has been positioned in the pulmonary artery, sheath 690 is removed from delivery lumen 676, proximal fitting 690 is capped, and negative pressure is applied through side arm 686 to withdraw blood from the pulmonary artery through side inlet ports 680. During venting, balloon 674 may tend to be collapsed by the the force of blood around it and the negative pressure within delivery lumen 676; a screen or other porous blocking member 698 may thus be provided in inflation port 678 to prevent balloon 674 from being drawn into delivery lumen 676.

To set up the cardiac access system, the patient is initially placed under light general anesthesia. The withdrawal catheter 17 and the return catheter 19 of the cardiopulmonary by-pass system 18 are percutaneously introduced into the right femoral vein 16 and the right femoral artery 15, respectively. An incision 24 is also made in the left groin to expose the left femoral artery 23 and the aortic occluding catheter 10 is inserted into the left femoral artery through an incision therein and advanced upstream until the balloon 11 on the distal end of the occluding catheter 10 is properly positioned in the ascending aorta 12. Note that by-pass could similarly be established in the left groin and the aortic occlusion catheter put into the right femoral artery. The retrograde perfusion catheter 20 is percutaneously inserted by a suitable means such as the Seldinger technique into the right internal jugular vein 44 or the subclavian vein and advanced into the right atrium 45 and guided through the discharge opening 46 into the coronary sinus.

The pulmonary venting catheter 54 is advanced through the right internal jugular vein 44 or the subclavian vein (whichever is available after introduction of retrograde perfusion catheter 20) into the right atrium 45, right ventricle 55, and into the pulmonary trunk 56. The occluding balloon 60 may be inflated if necessary by inflation with fluid passing through the lumen 62 to block the pulmonary trunk 56 and vent blood therein through the lumen 61 where it is discharged through the proximal end of the catheter which extends outside of the patient. The venting of the pulmonary trunk 56 results in the decompressing of the left atrium 14. The blood withdrawn through venting catheter 54 may be routed to cardiopulmonary bypass unit 18 for oxygenation and return to the patient's arterial system through arterial return catheter 19.

In the alternative, the venting catheter 54 may be provided with means on the exterior thereof, such as expanded coils as described in U.S. Pat. No. 4,889,137 (Kolobow), which hold open the tricuspid and pulmonary valves and perform the same function of decompressing the left atrium. See also the article written by F. Rossi et. at. in the Journal of Thoracic Cardiovascular Surgery, 1900;100:914–921, entitled "Long-Term Cardiopulmonary Bypass By Peripheral Cannulation In A Model Of Total Heart Failure", which is incorporated herein in its entirety by reference.

The operation of the cardiopulmonary by-pass unit 18 is initiated to withdraw blood from the femoral vein 16 through catheter 17, remove $CO_2$ from and add oxygen to the withdrawn blood and then pump the oxygenated blood through the return catheter 19 to the right femoral artery 15. The balloon 11 may then be inflated to occlude the ascending aorta 12, causing the blood pumped out of the left ventricle (until the heart stops beating due to the cardioplegic fluid as discussed hereinafter) to flow through the discharge port 41 into the first inner lumen 40 of the occluding catheter. The blood flows through the inner lumen 40 and out the third arm 32 of the adapter 26 into the by-pass line 33 and then into the blood filter and blood recovery unit 37 through the valve 34 and line 36. For blood and irrigation fluids containing debris and the like, the position of the valve 34 may be changed to direct the fluid through the discharge line 35.

The balloon 47 on the distal extremity of the retroperfusion catheter 20 is inflated to occlude the coronary sinus 21 to prevent fluid loss through the discharge opening 46 into the right atrium 45. A liquid containing a cardioplegic agent such as KCl is directed through the catheter 20 into the coronary sinus 21 and the pressure of the cardioplegic fluid within the coronary sinus 21 is maintained sufficiently high, (e.g. 40 mm Hg) so that the cardioplegic fluid will pass through the coronary veins, crossing the capillary beds to the coronary arteries 50 and 51 and out the ostia 52 and 53. However, cardioplegic fluid pressure is not increased far above 75 mm Hg. Once the cardioplegic fluid passes through the capillary beds in the myocardium, the heart very quickly stops beating. At that point the myocardium is paralyzed and has very little demand for oxygen and can be maintained in this state for long periods of time with minimal damage.

With the cardiopulmonary by-pass system in operation, the heart completely paralyzed and not pumping, the left atrium decompressed and the ascending aorta blocked by the inflated balloon 11 on the occluding catheter 10, the heart is appropriately prepared for a cardiac procedure.

While the heart is stopped and the patient supported on cardiopulmonary bypass, blood must be withdrawn from the pulmonary artery through venting catheter 54 at a rate sufficient to maintain decompression of the heart. At the same time, the blood withdrawn must not be subject to pressures which create excessive hemolysis. In an exemplary embodiment, blood is withdrawn at a rate of at least about 125 ml/min, and preferably about 250 to 1000 ml/min, while the pressure of the blood within venting catheter 54 is maintained above −150 mmHg.

Inflation of the inflatable member 11 on the distal end of the delivery catheter 10 fixes the distal end of the occluding catheter 10 within the ascending aorta 12 and isolates the left ventricle 13 and the upstream portion of the ascending aorta from the rest of the arterial system downstream from the inflatable member. The passage of any debris or emboli, solid or gaseous, generated during a cardiovascular procedure to regions downstream from the site would be precluded by the inflated balloon 11. Fluid containing debris or emboli can be removed from the region between the aortic valve and the occluding balloon 11 through the inner lumen 40 of catheter 10. A clear, compatible fluid, e.g. an aqueous based fluid such as saline delivered through the inner lumen 40 or the cardioplegic fluid discharging from the coronary ostia 52 and 53, may be maintained in the region wherein the cardiovascular procedure is to be performed to facilitate use of an angioscope or other imaging means that allows for direct observation of the cardiac procedure. Preferably, the fluid pressure in the left ventricle 13 is maintained sufficiently higher than that in the left atrium to prevent blood from the left atrium from seeping into the left ventricle and interfering with the observation of the procedure. The inner lumen 40 is dimensioned to allow for the passage of instruments used during the cardiac procedure such as a tissue cutter, an angioscope, and tubes used for infusing irrigation fluid and for aspirating debris, thrombus and the like, and for the introduction of a prosthetic device, such as a heart valve.

Additional exemplary embodiments of the cardiac access system of the invention are illustrated in FIGS. 16–24. The heart 210 of FIGS. 16 and 17 is positioned in the living body of a patient and is accessed percutaneously.

In order to induce cardioplegia in the heart while maintaining the patient it is necessary to divert the patient's blood circulation through an extracorporeal cardiopulmonary by-pass system. This is achieved by isolating the heart 210 on both the venous and arterial sides using appropriate percutaneously inserted venous catheter 211, aortic balloon catheter 212, and if this catheter 212 doesn't have provision for arterial blood return, arterial catheter 239 (see FIG. 18). The venous outflow and arterial inflow lumina of the catheters 211 and 212 of the by-pass system are of sufficient cross sectional area to achieve standard blood flows to maintain the patient's systemic circulation during the period of extracorporeal circulation.

In the case of the use of a single venous double-ballooned catheter 211, as is shown in FIG. 16, the catheter 211 is inserted through the femoral vein preferably. A suitable guide wire is initially inserted and the catheter 211 is then introduced in known manner under fluoroscopic guidance. The catheter 211 includes a pair of separately inflatable balloons 214 and 215 each connected to a balloon inflation control device (not shown) through suitable lumina in the catheter 211. The balloon 214 is adapted to occlude the superior vena cavae 216 while the balloon 215 is adapted to occlude the suprahepatic inferior vena cavae 217. A blood withdrawal lumen in the catheter 211 has an inlet orifice 218 flush with the balloon 214, to avoid venous collapse during blood flow into the catheter 211, and a series of inlet slots 219 in the inferior vena cavae. Blood drawn into the inlets 218 and 219 enters a common single lumen. Blood drawn into the by-pass system through the catheter 211 is oxygenated and returned to the patient in a manner which will be hereinafter described.

A separate lumen in the catheter 211 opens into the right atrium 222 through aperture 221 to allow evacuation of blood from the right heart and the infusion of saline to induce topical cooling and/or to improve visual acuity within the right heart.

Figure 24B:
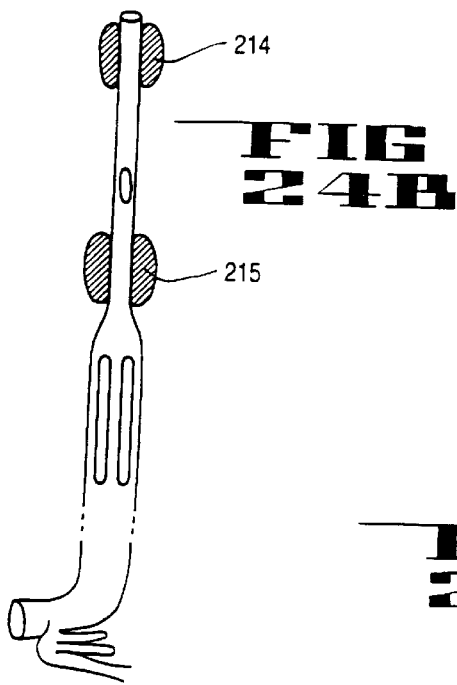
FIGS. 24a and 24b show schematically two alternative catheter arrangements for the isolation of the right atrium and venous drainage.
Figure 24A:
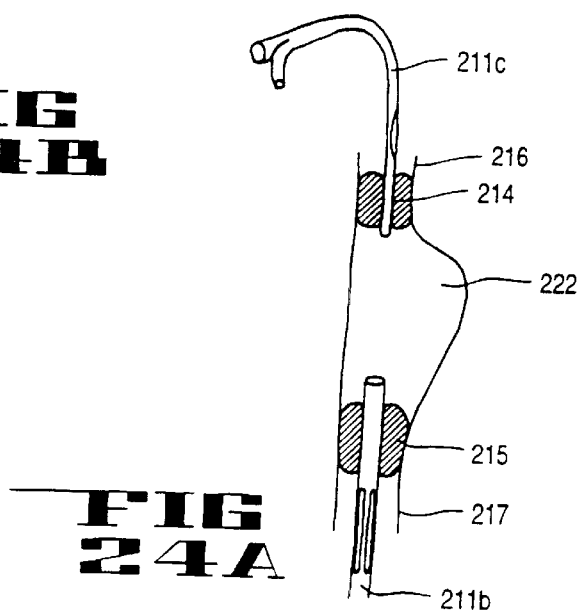

In use, after the catheter 211 has been positioned the balloons may be inflated or deflated to vary the rate of venous return to the right atrium 222 and therefore the degree of decompression of the left heart. Venous drainage may be effected by gravitational drainage or by applying a degree of negative pressure to assist flow into the pump oxygenator. It will be appreciated that the distance between the balloons 214 and 215 will need to be correct for a given patient and this may be assessed by X-ray examination to allow selection of an appropriately sized catheter. Alternatively separate catheters 211b and 211c could be used, as is shown in FIG. 24a, for the inferior and superior vena cavae. The cannula 211b being introduced as has been described above and the cannula 211c being introduced through the jugular or subclavian vein. It will also be appreciated that for simple operations not requiring complete occlusion of the right atrium it is possible to merely insert a simple catheter 211 into the right atrium to draw blood into the by-pass system as is seen in FIG. 17. Positioning under fluoroscopic guidance is not essential in this case.

The catheter 212 is positioned in the manner described above with its free end located in the ascending aorta 223. The catheter 212 is so positioned by insertion preferably through the femoral artery 224 and via the descending aorta 225 as is seen in FIG. 18.

If desired a fluoroscopic dye may be introduced into the aortic root 226 through the catheter 212 for accurate positioning of the tip of the catheter 212 relative to the aortic root 226 and the coronary ostia.

The catheter 212 carries at its free end a balloon 227. The balloon 227 is arranged to be inflated with saline from an inflation control device 228 of known type through a lumen in the catheter 212. The device 228 is fitted with a pressure gauge 229 to allow the operator to control the inflation of the balloon 227. The pressure of the fully inflated balloon 227 should be of the order of 350 mmHg so as to be sufficient to effectively occlude the aorta and to prevent the balloon moving while not being so great as to cause damage to the aortic wall. The balloon 227 should have a maximum diameter sufficient to occlude the aorta and for this purpose the maximum diameter should be about 35 mm. The balloon 227 should have a length of about 40 mm so as not to be so long as to occlude or impede blood flow to the coronary arteries or to the brachiocephalic, subclavian or carotid arteries. If necessary in any given patient the required length and diameter of the balloon may be determined by angiographic, X-ray examination or echocardiography and an appropriately sized catheter selected on that basis.

The balloon 227 is preferably connected to the lumen 232 through which it is inflated at the end of the balloon 227 distal to the tip of the catheter 212 through orifice 231 (see FIG. 20). This allows the tip of the catheter to contain fewer lumina than the remainder of the catheter. Accommodation of the deflated balloon around the tip of the catheter is thus possible without adding to the diameter of the tip as compared with the rest of the catheter 212.

Figure 23A:
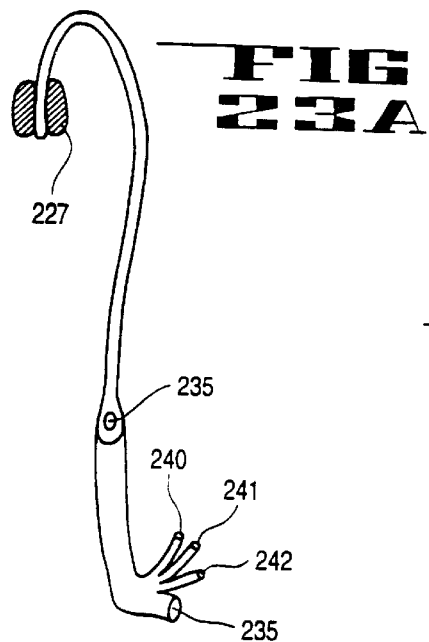
FIGS. 23a and 23b show schematically two alternative arrangements to the catheter shown in FIG. 19.
Figure 23B:
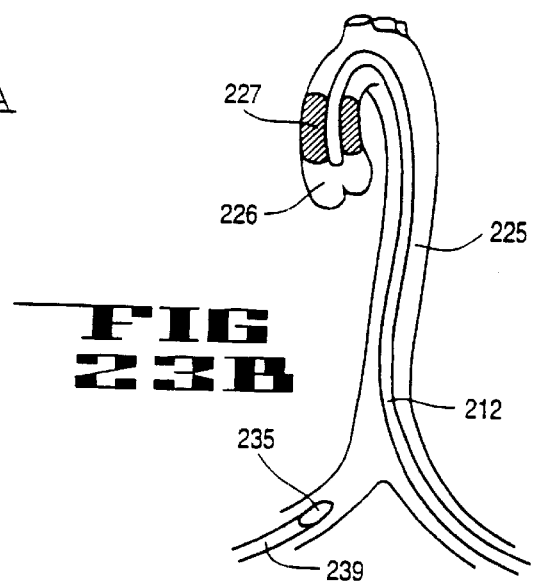

The catheter 212 includes a plurality of lumina (see FIGS. 21 and 22). In addition to the balloon inflation lumen 232 there is at least a single venting/cardioplegia lumen 233 of circular cross-section. There may be a separate and extra circular lumen 234 for instrumentation. If two lumens are present the venting/cardioplegia lumen may be circular or crescent shaped in cross-section (FIG. 21a, 21b). The diameter of the various lumina should be as small as practicable commensurate with the intended use. In addition, there may be a continuous lumen 235 through which arterial blood is returned from the by-pass. This may flow out of the catheter 212 through an orifice in the region of the external iliac artery. In alternative embodiments of the invention such as shown in FIGS. 18 and 23b the arterial return lumen 235 may comprise its own catheter 239 of known type introduced into the other femoral artery or some other suitable artery.

In use the catheter 212 is introduced percutaneously by puncture or cutdown as has been described and once blood flow through the by-pass is established (including systemic cooling) flows are reduced and the balloon 225 is inflated. Flows are then returned to the operating levels and a suitable cardioplegic agent is introduced into the aortic root. Once the full volume of cardioplegic agent has been given and cardiac arrest achieved, the lumen is then used to vent the heart. The heart may then be operated on or examined by insertion of instrumentation 237 such as a cardioscope or a laser into the heart through the lumen 234 or through thoracic and/or atrial trocars. Alternatively, with the heart on by-pass as described above the heart can be approached by an open method by an incision other than median sternotomy. Venting of the left ventricle may be effected by providing an extended cannula 238 projecting from lumen 233 into the left ventricle (see FIG. 17) or by simply applying negative pressure to the venting lumen 233 of the aortic catheter. To reverse cardioplegic arrest the body is rewarmed and the balloon 227 deflated. Aortic blood is thus allowed to perfuse the heart. Whilst the body remains supported by peripheral cardiopulmonary by-pass, the return of the heart rhythm is awaited. External defibrillation may be necessary. Weaning from by-pass is then completed in a routine fashion.

Figure 5:
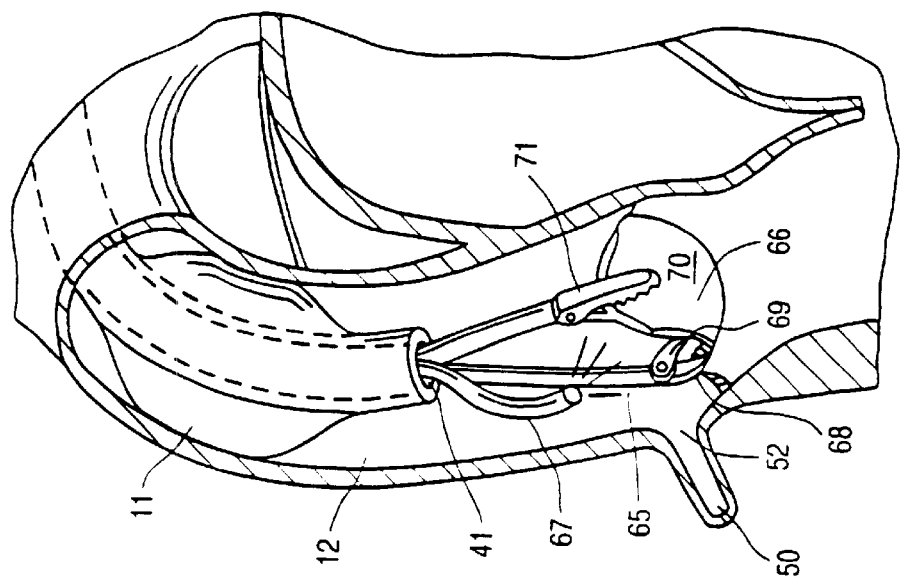
FIG. 5 is an elevational view, partially in section of the occluding catheter shown in FIG. 2 schematically illustrating the removal of an aortic heart valve.

The cardiac accessing system of the invention is particularly useful in the removal of the aortic heart valve and replacement thereof with a prosthetic heart valve which is illustrated in FIGS. 5 through 8. As shown in FIG. 5, a tissue cutter 65 is inserted into the patient through the inner lumen 40 of the occluding catheter 10 and advanced therein to the site of the aortic valve 66 which is to be removed. An angioscope 67 is likewise advanced through the inner lumen 40 until the distal end thereof extends out of the distal end of the occluding catheter 10. At least one of the cutting blades 68 and 69 on the tissue cutter 65 is actuated from the proximal end thereof which extends out of the second arm 30 of the adapter 26 on the proximal end of the catheter 10. The guidance and operation of the cutter 65 is controlled by the physician or other operator while observing the cutter through the angioscope 67. Due to its size and condition, the aortic valve 66 will usually have to be cut into smaller sections, such as section 70 as shown, so that it will fit within the inner lumen 40 of the occluding catheter 10 in order to remove the valve material from the patient. Preferably, forceps 71 or other suitable grasping means are employed to hold onto the aortic valve sections as they are severed by the cutting means 65 to ensure that the valve sections are accurately severed from the site with little or no damage to the underlying tissue of the ascending aorta and removed through the inner lumen 40. The cutting means 65 may have to be withdrawn from the occluding catheter 10 before large severed portions of the aortic valve 66 can be removed by forceps 71. During the procedure a continuous flow of clear liquid, such as the clear cardioplegic fluid exiting the ostia 52 and 53 and/or fluid being infused via the clamp 10 or an angioscope 67, is maintained to facilitate the observation of the region by the operator using the angioscope 67. After the valve 66 has been severed and removed from the region, the instruments used for this particular procedure are withdrawn from the patient through the inner lumen 40 of the occluding catheter 10. Instead of or in addition to mechanical cutting means, laser, electrosurgery, or other cutting methods may be employed in the valve removal procedure.

Direct observation of the placement of the cutting device 65 by suitable imaging means such as an angioscope 67 will ensure accurate positioning of the cutter blades 68 and 69 against the aortic valve to more effectively sever the valve 66 with little or no damage to the supporting aortic tissue. Aortic damage might interfere with the placement of a replacement valve 72 at the site. The precision of the valve removal and replacement is important to the success of endovascular valve replacement. There are several imaging techniques presently available, in addition to the angioscopic technique described, which provide complementary options to assure this precision, namely 1) transesophageal echocardiography; 2) intravascular ultrasound passed through the inner lumen of the delivery catheter 10; 3) intravascular ultrasound or angioscopy passed intravascularly via the venous system through the intra-atrial septum, across the mitral valve, and into the left ventricle; and 4) fluoroscopy. Note that an angioscope within the left ventricle would provide both the added benefit of allowing constant high definition imaging of the entire procedure and high-flow irrigation.

After the heart valve 66 is removed, a replacement valve 72 is then advanced through the inner lumen 40 of the occluding catheter 10 as shown in FIG. 6. The valve 72 is preferably a bioprosthetic valve such as xenograft valve. Porcine glutaraldehyde preserved valves are quite suitable because, as previously mentioned, they are readily accessible, they are storable, and they are available in a variety of sizes. The replacement valve 72, which is shown in FIG. 6 in an inverted and folded condition, has a Dacron skirt 73 secured to the lower rim of the natural porcine valve to facilitate securing the replacement valve to the wall of ascending aorta 12 at or near to the site from which the original aortic valve 66 was removed. The folded and inverted replacement valve 72 is disposed within the expanded end 74 of valve delivery catheter 75 so that the valve 72 can be advanced through the occluding catheter 10. The valve 72 is urged out of the expanded end 74 by the connector cables 84 which are connected to the upper extensions of the valve by releasable means 83. Once outside of the expanded end 74, the valve 72 expands due to the natural resiliency of the valve and the connector cables. The valve delivery catheter 75 is then removed by withdrawing it through the inner lumen 40 of the occluding catheter 10. Alternatively, the valve 72 may be provided with a temporary or permanent expandable support frame. The frame may contain stapling elements to secure the valve to the aortic wall.

The Dacron skirt 73 is fixed to the aortic root 12 by means of a plurality of U-shaped staples 76, as shown in FIG. 7, which are secured by the stapling mechanism 77 which is advanced through the inner lumen 40 and out of the distal port 41. The stapling mechanism 77 has an L-shaped holding arm 78 that holds the staple 76 and shaping member 79 having an arcuate shaping surface 80 which presses the staple 76 against holding arm 78 deforming the staple as it is pushed through the Dacron skirt 73 and into the aortic wall 81 as shown to force the pointed arms or tines thereof toward each other and fix the staple within the aortic wall. In the alternative the holding arm 78 may be moved toward the shaping member 79 or both may be advanced toward each other. The stapling mechanism 77 is preferably provided with a removable protective sheath (not shown) to facilitate the advancement of the mechanism through the inner lumen 40 without the pointed ends or tines of the staples 76 sticking into the inner wall of the occluding catheter 10 which defines the inner lumen 40. Usually about 10 to about 20 staples will be required to adequately secure the skirt 73 to the aortic wall 81. The angioscope 67 is provided to allow the physician to observe the procedure and guide the stapling mechanism 77 to the desired location and to secure the staple 76 and the skirt 73 at the desired location within the aortic root 12.

Once the Dacron skirt 73 is properly secured, the inverted valve 72 is pulled through the fixed Dacron skirt 73, as shown in FIG. 8, and the upper extensions of the new valve 72 are stapled in essentially the same manner as the Dacron skirt 73. Care must be exercised when placing the Dacron skirt 73 prior to securing it to the aortic wall 81 so that when the inverted portion of the new valve 72 is pulled through the secured Dacron skirt 73, the ostia 52 and 53 of the coronary arteries 50 and 51 are not blocked by the upper extensions 82 of the valve 72. After the upper extensions 82 are secured to the aortic wall 81, the releasable means 83 at the end of the connector cables 84 are released and the cables are withdrawn through the inner lumen 40 of the occluding catheter 10.

Any tissue debris resulting from the aortic valve removal and new valve placement is trapped by the barrier formed by the inflated balloon 11 on the distal end of the occluding catheter 10. However, liquid in the aortic region containing such debris may be removed through an aspiration tube (not shown) disposed within the inner lumen 40 of the occluding catheter 10 or through inner lumen 40 by aspirating the fluid containing the debris. An irrigation catheter may be used to dislodge any debris caught between the inflated balloon 11 and the aortic wall where the two meet.

When the replacement valve 72 is secured in place, the fluid pumped through the retroperfusion catheter 20 is changed to a compatible fluid, e.g. saline or blood, containing no cardioplegic agents in order to flush out the cardioplegic materials from the myocardium through the ostia 52 and 53. The pulmonary venting catheter 54 may also be removed at the same time. Shortly thereafter the heart begins to beat on its own or it is externally defibrillated and the blood coming into the right heart is pumped through the pulmonary trunk to the lungs where it is oxygenated in the normal fashion. Oxygenated blood is returned from the lungs into the left atrium and is then pumped from the left ventricle through the new valve into the ascending aorta. Initially, the balloon 11 is maintained in the inflated condition, forcing the blood pumped out of the left ventricle to pass through the region of the ascending aorta 12 into inner lumen 40 of the occluding catheter 10 taking with it debris, emboli and the like. The blood passing through inner lumen 40 is directed through the third arm 32 of adapter 26, through the valve 34 and line 36 leading to blood filter and recovery unit 37 where the blood may be filtered and returned to the patient through the cardiopulmonary by-pass system 18. Alternatively, the position of the valve 34 may be changed by means of arm 85 to discharge blood or other fluid containing tissue, emboli, debris and the like through discharge line 35. After sufficient time has elapsed to ensure that debris and embolus free oxygenated blood is being pumped out of the left ventricle 13 the balloon 11 is deflated to allow natural blood flow through the aorta and the cardiopulmonary by-pass system 18 is shut down.

The occluding catheter shaft 39 may be formed of conventional materials such as polyethylene, polyvinyl chloride and the like. Balloon 11 may be formed of materials such as latex, silicone, C-Flex, or the like. Preferably, the balloon 11 is elastic, so as to expand to and circumferentially occlude the vessel into which it is positioned when fluid pressure is applied to the balloon. Alternatively, the balloon 11 may be formed of polymers such as polyethylene, polyethylene terephthalate, or a polyolefinic ionomer such as Surlyn®, which is available from E I. DuPont, DeNemours & Co. Such a balloon would be relatively inelastic when inflated, so as to inflate to a predetermined size and maintain essentially that size even when additional fluid pressure is applied within the interior of the balloon. The balloon 11 will generally have an expanded diameter of about 20 to 40 mm to effectively occlude the patient's ascending aorta and an expanded length of about 2 to about 10 cm so as to be disposed between the coronary ostia and the brachiocephalic artery without blocking these arteries. The overall length of the occluding catheter should be at least 80 cm to facilitate passage through the femoral or brachiocephalic arteries to the ascending aorta.

The retroperfusion catheter 20 may be a commercially available retroperfusion catheter. There are suitable cardiopulmonary by-pass systems available commercially. For a brief discussion of cardiopulmonary by-pass systems reference is made to Weber, John G., *Encyclopedia of Medical Devices and Instrumentation*, Vol. 3, pp. 1440–1457.

An alternative tissue cutting system is depicted in FIGS. 9 and 10. In this embodiment catheter 90 is provided with a cutting head 91 which is slidably disposed within the cutter housing 92. The cutting head 91 is provided with a cutting edge 93 and cutter housing 92 is provided with cutting edge 94. The distal end of the catheter 90 is urged against tissue which is to be removed so that the tissue is pressed into the receiving chamber 95 within the cutting head 91. The cutting head 91 is slidably withdrawn from the cutter housing 92 so that the cutting edge 93 slides by the cutting edge 94 in a cutting relationship so as to sever the tissue within the receiving chamber 95. The severed tissue may be removed by aspiration or the cutting head 91 may be withdrawn from the patient and the severed tissue may be manually or otherwise removed. Preferably, the positioning of the distal end of catheter 90 and the urging of the cutting head against the tissue to be removed is observed by the physician or other operator through angioscope 67 or other suitable imaging system as previously described.

Another cutting system 96, which is shown in FIG. 11, has expandable cutting blades 97 and 98 which are biased or otherwise adapted to expand to a cutting position as shown and rotated at high rotational speeds by a drive shaft and then pressed against the tissue to be severed. The blades 97 and 98 may be biased to expand outwardly by a spring (not shown) or the blades may be forced outwardly by the high speed rotation thereof. This cutting operation is likewise preferably observed by the physician or other operator to ensure proper cutting of the tissue to be removed.

An alternative valve introducer device 100 is shown in FIGS. 12–13 which is adapted to contain a prosthetic or replacement valve 101 within expanded distal portion 102. The introducer device 100 may be introduced by itself or through the inner lumen of the occluding delivery catheter such as previously described until the enlarged distal portion 102 is located at or extends out of the distal end of the delivery catheter. The valve introducer device 100 may be provided with one or more positioning balloons 103 surrounding the expanded distal end 102 thereof which may be inflated in a differential manner, to assure accurate positioning of a prosthetic valve 101 when delivered out of the expanded distal end. A means, such as piston 104 is provided to push the replacement valve 101 out of the expanded distal end 102 when it is in the appropriate position within the patient's ascending aorta. Forceps or other holding means as previously described may be used to position the replacement valve 101 within the location from which the original valve has been removed.

An alternative replacement or prosthetic valve 101 is best shown in the expanded condition in FIGS. 14 and 15. As indicated, the valve 101 is provided with a cylindrical base 105 having mounting staples 106 which can be pressed into the wall portion of the ascending aorta at the desired situs by means of an expandable inelastic balloon 107 which is inflated within the valve 101. The upper extensions 108 of the replacement valve 101 from which the leaves or cusps 109 are supported are for the most part self supporting and may not require securing to the wall section of the ascending aorta. The valve introducer device 100 and the inflatable balloon 107 which when inflated presses the mounting staples 106 into the aortic wall may, when deflated, be withdrawn through the inner lumen of a delivery catheter. The aortic region between the site of the replacement valve and the delivery catheter may be well irrigated to remove debris, emboli and the like before regular blood flow through the region is resumed.

The invention provides several benefits, including the ability to endovascularly replace existing cardiac valves or perform other cardiac procedures while avoiding the riskier, more expensive and more traumatic open-heart surgical procedure.

The replacement prosthetic valve device is preferably a bioprosthetic device because these valves do not require the patient to undertake life-long anticoagulant therapy as do mechanical valves. Once inserted, the bioprosthetic valve is capable of operating autonomously. The useful life of a bioprosthetic valve placed via the endovascular procedure may extend to over twenty years, and since most of the valve procedures are performed on the elderly, the bioprosthetic valve will usually function well throughout the remaining life of the patient.

Once the endovascular implantation of the prosthetic valve device is completed in the patient, the function of the prosthetic valve device can be monitored by the same methods as used to monitor valve replacements done by open-heart surgery. Routine physical examination, angiography, or periodic echocardiography can be performed. In contrast to open-heart surgery, however, the patient will recover in a very short period when his or her aortic valve is endovascularly removed and replaced with a prosthetic valve. The replacement valve device can be used in any patient where bioprosthetic valves are indicated, and is particularly suitable for elderly patients and patients unable to tolerate open-heart procedures or life-long anticoagulation.

Unless described otherwise, the various components of the system of the present invention can be formed of conventional materials using conventional manufacturing techniques. The dimensions of the various components are selected so that they perform their intended functions in their intended environment.

Turning now to FIGS. 25–40, several additional exemplary embodiments of an endovascular device for partitioning the ascending aorta according to the invention will be described. As illustrated in FIG. 25, partitioning device 320 includes a shaft 322 having a distal end 324 and a proximal end 326. An expandable means 328 for occluding the ascending aorta is mounted to shaft 322 near distal end 324. In a preferred embodiment, occluding means 328 comprises a polymeric balloon 330 (shown inflated) of a material, geometry, and dimensions suitable for completely occluding the ascending aorta to block systolic and diastolic blood flow, as described more fully below.

Shaft 322 has a diameter suitable for introduction through a femoral or iliac artery, usually less than about 9 mm. The length of shaft 322 is preferably greater than about 80 cm, usually about 90–100 cm, so as to position balloon 330 in the ascending aorta between the coronary ostia and the brachiocephalic artery with proximal end 326 disposed outside of the body, preferably from the femoral or iliac artery in the groin area. Alternatively, the shaft may be configured for introduction through the carotid artery, through the brachial artery, or through a penetration in the aorta itself, wherein the shaft may have a length in the range of 20 to 60 cm.

Partitioning device 320 further includes a first inner lumen 329, shown in FIGS. 26A–26B, extending between proximal end 326 and distal end 324 with an opening 331 at distal end 324. Additional openings in communication with inner lumen 329 may be provided on a lateral side of shaft 322 near distal end 324.

Shaft 322 has a shaped distal portion 332 configured to conform generally to the curvature of the aortic arch such that opening 331 at distal end 324 is spaced apart from the interior wall of the aorta and is axially aligned with the center of the aortic valve. Usually, shaped distal portion 332 will be generally U-shaped, such that a distal segment 334 is disposed at an angle between 135° and 225°, and preferably at approximately 180° relative to an axial direction defined by the generally straight proximal segment 336 of shaft 322. Shaped distal portion 332 will usually have a radius of curvature in the range of 20–80 mm (measured at the radial center of shaft 322), depending upon the size of the aorta in which the device is used. The configuration of shaped distal portion 332 allows distal segment 334 to be positioned centrally within the lumen of the ascending aorta and distal end 324 to be axially aligned with the center of the aortic valve, thereby facilitating infusion or aspiration of fluids as well as introduction of surgical tools through opening 331 without interference with the wall of the aorta, as described more fully below.

In an exemplary embodiment, shaped distal portion 332 is preshaped so as to maintain a permanent, generally U-shaped configuration in an unstressed condition. Such a preshaped configuration may be formed by positioning a mandrel having the desired shape in first inner lumen 329, then baking or otherwise heating shaft 322 and the mandrel for a sufficient time and sufficient temperature to create a permanent set therein, e.g., 1–3 hours at a temperature in a range of 120_C. to 180_C., depending upon the material used for shaft 322.

Alternative embodiments of shaped distal portion 332 are illustrated in FIGS. 25B and 25C. In the embodiment of FIG. 25B, U-shaped distal portion 332, rather than having a continuous, constant curvature, is preshaped in a more angular fashion, with bends 333 of relatively small curvature separating segments 335 which are either straight or of larger curvature. Bends 333 and/or segments 335 may further be configured to engage the inner wall of the aortic arch to deflect distal end 324 into a desired position in the ascending aorta.

In the embodiment of FIG. 25C, shaped distal portion 332 is configured in a general "S" shape for introduction into the ascending aorta from a location superior to the aortic arch. In this way, distal segment 334 may be positioned within the ascending aorta, with proximal segment 336 extending from the aortic arch through the brachiocephalic artery to the carotid or brachial artery, or through a penetration in the aorta itself, to a point outside of the thoracic cavity.

As shown in FIG. 25A, distal segment 334 may be skewed (non-coplanar) relative to a central longitudinal axis of proximal segment 336, in order to further conform to the shape of the patient's aortic arch and align with the center of the aortic valve. In an exemplary embodiment, distal segment 334 is disposed at an angle α relative to a plane containing the central axis of proximal portion 336, wherein α is between 2° and 30°, usually between 10° and 20°, and preferably about 15°. The shape and dimensions of shaped distal portion 332 and angle α of distal segment 334 may vary, however, according to the configuration of the aortic arch in any individual patient.

In a preferred embodiment, the device will include a soft tip 338 attached to distal end 324 to reduce the risk of damaging cardiac tissue, particularly the leaflets of the aortic valve, in the event the device contacts such tissue. Soft tip 338 may be straight or tapered in the distal direction, with an axial passage aligned with opening 331 at the distal end of shaft 322. Preferably, soft tip 338 will be a low durometer polymer such as polyurethane or Pebax, with a durometer in the range of 65 Shore A to 35 Shore D.

At least one radiopaque stripe or marker 339 is preferably provided on shaft 322 near distal end 324 to facilitate fluoroscopic visualization for positioning balloon 330 in the ascending aorta. Radiopaque marker 339 may comprise a band of platinum or other radiopaque material. Alternatively, a filler of barium or bismuth salt may be added to the polymer used for shaft 322 or soft tip 338 to provide radiopacity.

As illustrated in FIGS. 25, 26A and 26B, a straightening element 340 is disposed in first inner lumen 329 of shaft 322 so as to slide longitudinally relative to the shaft. Straightening element 340 may comprise a tubular stylet with a longitudinal passage 344 for receiving a guidewire 342, as described below. Alternatively, element 340 may comprise a relatively stiff portion of the guidewire itself. Straightening element 340 may be a polymeric material or a biocompatible metal such as stainless steel or nickel titanium alloy with a bending stiffness greater than that of shaft 322. In this way, straightening element 340 may be advanced distally into preshaped distal portion 332 so as to straighten shaft 322, facilitating subcutaneous introduction of partitioning device 320 into an artery and advancement to the aortic arch. Straightening element 340 may then be retracted proximally relative to the shaft so that distal end 324 can be positioned in the ascending aorta with preshaped distal portion 332 conforming to the shape of the aortic arch.

A movable guidewire 342 is slidably disposed through first inner lumen 329, either through longitudinal passage 344 in straightening element 340 (FIG. 26B), external and parallel to straightening element 340, or through a separate lumen (not shown) in shaft 322. Guidewire 342 extends through opening 331 in distal end 324 of shaft 322 and may be advanced into an artery distal to shaft 322, facilitating advancement of shaft 322 through the artery to the ascending aorta by sliding the shaft over the guidewire. In an exemplary embodiment, guidewire 342 is relatively stiff so as to at least partially straighten shaft 322, so that straightening element 340 is unnecessary for introduction of shaft 322. In this embodiment, guidewire 342 may be, for example, stainless steel or a nickel titanium alloy with a diameter of about 1.0 mm to 1.6 mm.

Figure 27:
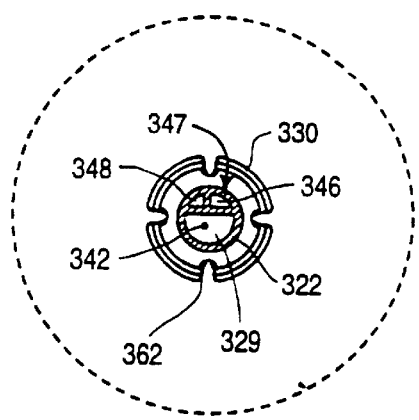
FIGS. 27 and 28 are transverse cross-sections taken along lines 27—27 and 28—28 in FIGS. 26A and 26B, respectively.
Figure 29A:
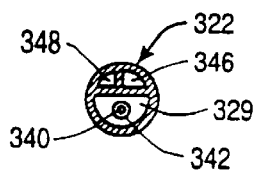
FIGS. 29A and 29B are transverse cross-sections taken along line 29—29 in FIG. 26A, showing alternative embodiments of the shaft of the device illustrated therein.

Shaft 322 may have any of a variety of configurations depending upon the particular procedure to be performed. In one embodiment, shaft 322 has a multilumen configuration with three non-coaxial parallel lumens in a single extrusion, as illustrated in FIGS. 26A, 27 and 29A. The three lumens include first inner lumen 329, which receives straightening element 340 and guidewire 342 and includes opening 331 at its distal end, an inflation lumen 346 which opens at an inflation orifice 347 (FIG. 27) near the distal end of shaft 322 in communication with the interior of balloon 330, and a third lumen 348 which has an opening (not shown) at distal end 324 of the shaft to sense pressure in the ascending aorta upstream of balloon 330. In this embodiment, the largest transverse dimension of first inner lumen 329 is preferably about 1 mm–4 mm. Advantageously, the distal opening in third lumen 348 is radially offset from opening 331 in first inner lumen 329, so that infusion or aspiration of fluid through first inner lumen 329 will not affect pressure measurements taken through third lumen 348.

Figure 29B:
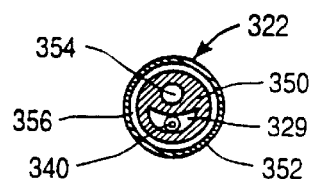

In a second embodiment, illustrated in FIG. 29B, shaft 322 has a dual lumen inner member 350 and a coaxial outer member 352. Inner member 350 includes first inner lumen 329 which receives straightening element 340 and opens at distal opening 331, and a third lumen 354 which has an opening (not shown) at its distal end for measuring pressure in the ascending aorta. Outer member 352 defines a coaxial inflation lumen 356 which, at its distal end, is in communication with the interior of balloon 330. Balloon 330 and outer member 352 may comprise a single integrated extrusion, or balloon 330 may be bonded or otherwise attached to outer member 352 near the distal end of shaft 322 using well-known techniques. Outer member 352 may have an open distal end which communicates with the interior of balloon 330. Alternatively, the distal end of outer member 352 may be closed, for example, by bonding to the exterior of inner member 350, with an inflation orifice 347 provided as shown in FIG. 26A for communication between lumen 356 and the interior of the balloon.

Figure 28:
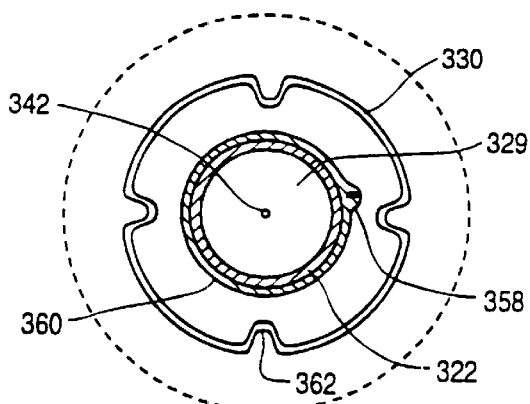
Figure 30:
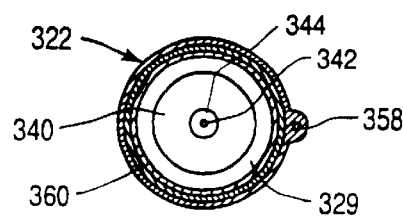
FIG. 30 is a transverse cross section taken along line 30—30 in FIG. 26B.

In a third embodiment, illustrated in FIGS. 26B, 28 and 30, shaft 322 has a first inner lumen 329 of large diameter configured to receive various types of surgical instruments, as well as to receive straightening element 340. An inflation lumen 358 extends parallel to first inner lumen 329 and is in communication with the interior of balloon 330 through an inflation orifice 361, shown in FIG. 26B. In this embodiment, shaft 322 may comprise a single extrusion containing inflation lumen 358 and inner lumen 329, or two individual tubes bonded to one another, one tube containing lumen 329 and the other containing inflation lumen 358. With this construction, shaft profile can be minimized while making lumen 329 as large as possible within the confines of the vessels in which the device is positioned. In this embodiment, first inner lumen 329 will have a diameter of at least about 5 mm and preferably about 8 mm. Partitioning device 320 thereby provides a passage of maximum diameter for endovascular introduction of surgical instruments such as visualization scopes, aspirators, irrigation tubes, cutting, stapling and suturing devices, and the like.

It should be noted that where partitioning device 320 is to be utilized for antegrade delivery of cardioplegic fluid through first inner lumen 329, it will be configured to provide a sufficient flowrate of such fluid to maintain paralysis of the heart, while avoiding undue hemolysis in the blood component (if any) of the fluid. In a presently preferred embodiment, cold blood cardioplegia is the preferred technique for arresting the heart, wherein a cooled mixture of blood and a crystalloid KCl/saline solution is introduced into the coronary arteries to perfuse and paralyze the myocardium. The cardioplegic fluid mixture is preferably run through tubing immersed in an ice bath so as to cool the fluid to a temperature of about 3_C.–10_C. prior to delivery through inner lumen 329. The cardioplegic fluid is delivered through inner lumen 329 at a sufficient flowrate and pressure to maintain a pressure in the aortic root (as measured through third lumen 348) high enough to induce flow through the coronary arteries to perfuse the myocardium. Usually, a pressure of about 50–100 mmHg, preferably 60–70 mmHg, is maintained in the aortic root during infusion of cardioplegic fluid, although this may vary somewhat depending on patient anatomy, physiological changes such as coronary dilation, and other factors. At the same time, in pumping the cardioplegic fluid through inner lumen 329, it should not be subject to pump pressures greater than about 300 mmHg, so as to avoid hemolysis in the blood component of the fluid mixture. In an exemplary embodiment, first inner lumen 329 is configured to facilitate delivery of the cardioplegic fluid at a rate of about 250–350 ml/min. preferably about 300 ml/min., under a pressure of no more than about 300 ml/min, enabling the delivery of about 500–1000 ml of fluid in 1–3 minutes. To provide the desired flowrate at this pressure, inner lumen 329 usually has a cross-sectional area of at least about 4.5 mm$^2$, and preferably about 5.6–5.9 mm$^2$. In an exemplary embodiment, D-shaped lumen 329 in FIG. 29A has a straight wall about 3.3 mm in width, and a round wall with a radius of about 1.65 mm. A completely circular lumen 329 (not pictured), could have an inner diameter of about 2.7 mm. Inner lumen 329 could be significantly smaller, however, if the cardioplegic fluid did not have a blood component so that it could be delivered under higher pressures without risk of hemolysis. Because of its myocardial protective aspects, however, the forementioned blood/KCl mixture is presently preferred, requiring a somewhat larger lumen size than would be required for a crystalloid KCl cardioplegic fluid without blood.

In some embodiments, as shown in FIGS. 26B, 28 and 30, a wire braid or coil 360 may be embedded in the wall of shaft 322 to enhance radial rigidity and to maintain the transverse dimensions of first inner lumen 329. It is particularly important to maintain the roundness of first inner lumen 329 where surgical tools are to be introduced through the first inner lumen. If shaft 322 is made of sufficient diameter to accommodate such tools through lumen 329, the shaft may tend to flatten or kink when advanced into the curved region of the aortic arch. The use of wire braid or coil 360 to maintain lumen roundness allows tool profile to be maximized and allows tools to be advanced through the lumen with minimum interference. Wire braid or coil 360 may be formed of stainless steel or other biocompatible material such as nickel titanium alloy, aramid fibers such as Kevlar™ (DuPont), or nylon.

Shaft 322 may be constructed of any of a variety of materials, including biocompatible polymers such as polyurethane, polyvinyl chloride, polyether block amide, or polyethylene. In a preferred embodiment of the device shown in FIG. 26A, shaft 322 is urethane with a shore durometer in the range of 50D–80D. In the embodiment of FIG. 26B, wherein shaft 322 may have a significantly larger diameter as well as an embedded coil which both increase stiffness, a polyurethane with shore durometer of 60A–100 A may be used. Shaft 322 may have a bending modulus in the range of 70 to 100 kpsi, preferably about 80–90 kpsi. A bending modulus in this range provides sufficient stiffness to optimize pushability from a femoral or iliac artery to the ascending aorta, while providing sufficient flexibility to navigate the tortuous iliac artery and the aortic arch. Once partitioning device 320 has been positioned with distal end 324 in the ascending aorta, this bending modulus also facilitates exertion of a distally-directed force on shaft 322 from proximal end 326 to maintain the position of balloon 330 against the outflow of blood from the left ventricle as the balloon is inflated. In other embodiments, the dimensions, geometry and/or materials of shaft 322, as well as coil 360, may be varied over the length of the shaft so that the shaft exhibits variable bending stiffness in various regions. For example, preshaped distal portion 332 may be more flexible for tracking through the aortic arch, whereas proximal portion 336 may be stiffer for pushability and resistance to displacement.

Balloon 330 may be constructed of various materials and in various geometries. In a preferred embodiment, balloon 330 has a collapsed profile small enough for introduction into the femoral or iliac artery, e.g. 4–9 mm outside diameter, and an expanded (inflated) profile large enough to completely occlude the ascending aorta, e.g. 20–40 mm outside diameter. The ratio of expanded profile diameter to collapsed profile diameter will thus be between 2 and 10, and preferably between 5 and 10. The balloon is further configured to maximize contact of the working surface of the balloon with the aortic wall to resist displacement and to minimize leakage around the balloon, preferably having a working surface with an axial length in the range of about 3 cm to about 7 cm when the balloon is expanded. Textural features such as ribs, ridges or bumps may also be provided on the balloon working surface for increased frictional effects to further resist displacement.

Balloon 330 preferably has some degree of radial expansion or elongation so that a single balloon size may be used for aortas of various diameters. Materials which may be used for balloon 330 include polyurethanes, polyethylene terephthalate (PET), polyvinyl chloride (PVC), polyolefin, latex, ethylene vinyl acetate (EVA) and the like. However, balloon 330 must have sufficient structural integrity when inflated to maintain its general shape and position relative to shaft 322 under the systolic pressure of blood flow through the ascending aorta. In an exemplary embodiment, balloon 330 is constructed of polyurethane or a blend of polyurethane and polyvinyl such as PVC. It has been found that such materials have sufficient elastic elongation to accommodate a range of vessel diameters, while having sufficient structural integrity to maintain their shape and position in the ascending aorta when subject to outflow of blood from the left ventricle.

In a preferred embodiment, balloon 330 is further provided with a plurality of folds or pleats 362, shown in FIGS. 27 and 28, which allow the balloon to be collapsed by evacuation to a small collapsed profile for introduction into a femoral or iliac artery. In this embodiment, balloon 330 has a blow-up ratio, defined as the ratio of the fully-inflated outside diameter to the deflated outside diameter (before collapsing), of about 200%–400%, preferably 300%–400%. Pleats 362 are preferably at least three in number and each have a width representing approximately 5–25% of the circumference of the balloon when deflated (but not collapsed by subjecting the interior of the balloon to a vacuum). Pleats 362 may be formed into the balloon during the balloon-making process by using a dipping mandrel having longitudinal flutes formed in its periphery. The mandrel is dipped into a container of liquefied balloon material (e.g. polyurethane) so that a tubular layer of material solidifies onto the mandrel, conforming to the shape of the flutes. The mandrel is then removed, producing a pleated balloon of substantially constant thickness. Where a folded, rather than pleated, balloon is used, the folds may be formed after the balloon is made by vacuum collapsing the balloon onto a mandrel into the desired collapsed profile and heating the balloon, or by expanding the balloon under pressure and heat in a corrugated mold.

In alternative embodiments, occluding means 328 may comprise any of a variety of structures, including pivot, umbrella or fan-type occlusion mechanisms actuated by pull wire, torque cable, or other type of mechanical, hydraulic, electric, or shape-memory actuator. Further, occlusion means 328 may comprise multiple occlusion devices arranged in tandem on shaft 322; for example, a pair of balloons may be arranged one behind the other at the distal end of the shaft. In one embodiment, an occluding balloon is disposed on the shaft to be positionable in the ascending aorta, while a seating balloon is disposed distal to the occluding balloon so as to be positionable in the left ventricle through the aortic valve, as described in commonly assigned application Ser. No. 08/213,760, filed Mar. 16, 1994, the complete disclosure of which is incorporated herein by reference. By inflating the seating balloon in the left ventricle, the position of the occluding balloon in the ascending aorta may be maintained against the outflow of blood from the left ventricle.

Referring again to FIG. 25, a triple-arm adapter 364 is attached to the proximal end 326 of shaft 322. Triple-arm adapter 364 includes a working port 366 in communication with first inner lumen 329 through which straightening element 340, guidewire 342, and in some embodiments, surgical or diagnostic instruments may be introduced, as described below. Working port 366 may also be adapted for infusion of fluid such as cardioplegic fluid, saline or contrast solution, as well as for aspiration of blood, fluids and debris through first inner lumen 329. Triple-arm adapter 364 further includes an inflation port 368 in communication with the inflation lumen and configured for connection to an inflation fluid delivery device such as a syringe 370 or other commercially available balloon-inflation device such as the Indeflator™ available from Advanced Cardiovascular Systems, Inc. of Santa Clara, Calif. A pressure measurement port 372 is in communication with the third lumen (348 or 354) and is adapted for connection to a pressure measurement device. Alternatively, where shaft 322 includes only first inner lumen 329 and inflation lumen 358 as in FIGS. 26B, 28 and 30, port 372 may be in communication with first inner lumen 329 and configured for pressure measurement, fluid infusion or aspiration.

Referring now to FIGS. 31–33, a preferred embodiment of the method of the invention will be described. Initially, a partitioning device 320 of a size and configuration suitable for the particular patient must be selected. Usually, the patient's aorta will be observed by means of a fluoroscopic imaging to determine its size and shape, particularly in the region of the aortic arch. A partitioning device 320 will be selected having a length sufficient to allow occluding means 328 to be advanced into the ascending aorta from the point of introduction, which will preferably be a femoral or iliac artery in the groin area. Further, a partitioning device will be selected which has a preshaped distal portion 332 with dimensions and shape suitable for positioning the distal portion in the patient's aortic arch such that distal end 324 is spaced apart from the inner wall of the ascending aorta, preferably aligned with the center of the aortic arch. Usually, the preshaped distal portion will have a radius of curvature approximately equal to that of the aortic arch as measured to the center of the aorta, preferably within a tolerance of about +/−10 mm.

Referring to FIG. 31, partitioning device 320 is preferably subcutaneously inserted into a femoral or iliac artery 374 in the groin area using known techniques such as a cut-down or a percutaneous technique such as the Seldinger technique. Guidewire 342 is first introduced into femoral artery 374 and advanced toward the heart through iliac artery 376 and aorta 378 so that the distal end of guidewire 342 is in the ascending aorta (not shown in FIG. 31). Straightening element 340 is inserted into lumen 329 of shaft 322 and positioned in preshaped distal portion 332 so as to straighten the preshaped distal portion. With balloon 330 deflated, shaft 322 is positioned over guidewire 342, introduced into femoral artery 374 and advanced over guidewire 342 through iliac artery 376 and aorta 378. A fluoroscope may be used for visualization of radiopaque markers 339 on shaft 322 to facilitate positioning. As an alternative or supplement to fluoroscopic imaging, ultrasonic echocardiography may be used by, for example, positioning an echocardiographic transducer in the esophagus.

As an alternative to femoral or iliac introduction, shaft 322 may be introduced into carotid artery 387 or brachial artery 389. In such cases, distal portion 332 of shaft 322 will usually have a generally S-shaped configuration, as described above with reference to FIG. 25C. Such an S-shaped configuration facilitates positioning balloon 330 in the ascending aorta with shaft 322 extending superiorly from the aortic arch through brachiocephalic artery 386.

As illustrated in FIGS. 32 and 33, shaft 322 is advanced through aortic arch 380 until balloon 330 resides in ascending aorta 382 between coronary ostia 384 and brachiocephalic artery 386. As distal end 324 is advanced around the aortic arch, straightening element 340 is drawn proximally relative to shaft 322 so as to allow preshaped distal portion 332 to conform to the shape of the arch. In an alternative embodiment, a relatively stiff guidewire may be used without a separate straightening element, in which case the guidewire may remain in place as shaft 322 is advanced into the ascending aorta. Straightening element 340 and guidewire 342 may then be removed from shaft 322.

In an alternative technique, partitioning device 320 may be introduced into the aorta thoracoscopically. In this embodiment, distal end 324 of shaft 322 may be introduced through a small incision or cannula into the chest cavity. A small penetration is made in the aorta, either in the descending region or in the aortic arch. Shaft 322 is then inserted into the aorta using forceps or other thoracoscopic instruments introduced into the chest cavity through small incisions or cannulae. Such a technique may be useful where a patient's femoral or iliac arteries are unsuitable for introducing partitioning device 320 percutaneously or by cut down into those vessels.

As illustrated in FIG. 32, once shaft 322 has been positioned so that balloon 330 is in ascending aorta 382 between coronary ostia 384 and brachiocephalic artery 386, balloon 330 is expanded by injecting an inflation fluid, usually a saline solution with a radiographic contrast agent, from syringe 370 through inflation port 368. In an exemplary embodiment, the balloon will be fully inflated in approximately 15–45 seconds, depending upon the size of the inflation lumen and the viscosity of the inflation fluid used. In some embodiments, blood may be allowed to flow through inner lumen 329 and directed to cardiopulmonary bypass system 394 (described below), thereby reducing the pressure of blood flow against balloon 330 during inflation. When fully inflated, the exterior surface of balloon 330 contacts the inner walls of the ascending aorta so as to fully occlude the vessel and block substantially all systolic and diastolic blood flow past the balloon. While the heart remains beating, blood may flow from the left ventricle through the aortic valve and into the coronary ostia so as to perfuse the myocardium through the coronary arteries. The heart and coronary arteries are thus isolated from the remainder of the arterial system.

In an alternative embodiment, a gaseous inflation fluid may be used in order to increase inflation speed. In this way, balloon 330 can be fully inflated in less time than the period between systolic pulses, reducing the likelihood that the outflow of blood from the left ventricle during systole will displace balloon 330 from its position in the ascending aorta. Preferably, carbon dioxide is used as the inflation fluid, since carbon dioxide, being highly soluble in blood, is unlikely to produce potentially injurious gas emboli in the event of leakage from the balloon. Alternatively, helium may be used. A gas inflation pump and control device similar to those described in U.S. Pat. No. 4,771,765 and U.S. Pat. No. 4,902,272, which are hereby incorporated herein by reference, may be utilized for delivery of pressurized gas through inflation port 368. The inflation pump may be timed with the contractions of the heart to facilitate inflation of the balloon between systolic pulses. Using such a pump, balloon 330 may be fully inflated in less than about 1 second, and preferably less than about 0.5 second.

FIG. 32 illustrates the components of a system for arresting the heart constructed in accordance with the principles of the invention. A cardioplegic fluid delivery device 390 is connected to working port 366. A pressure measurement device 392 may be connected to port 372 to monitor pressure in the ascending aorta upstream of balloon 330 through third lumen 348. The patient is placed on a cardiopulmonary bypass (CPB) system 394 to maintain circulation of oxygenated blood throughout the body. Usually, a venous cannula 396 is positioned in the inferior vena cava or right atrium via a femoral vein for withdrawing de-oxygenated blood. In addition, a pulmonary artery venting catheter (described above with reference to FIG. 1) may be positioned through the right internal jugular vein or subclavian vein into the pulmonary trunk to withdraw the blood contained therein, thereby decompressing the left atrium. The withdrawn blood is delivered to CPB system 394 which removes carbon dioxide and oxygenates the blood. The oxygenated blood is then delivered to a femoral or iliac artery via an arterial cannula 398. A blood filter and recovery system 400 may also be connected to port 366 in partitioning device 320 via a routing switch 401 to receive blood and other fluids and debris from first inner lumen 329 before or after delivery of cardioplegic fluid, filter the blood to remove impurities, and deliver the blood to CPB system 394 for return to the patient's circulatory system. Further aspects of a CPB system suitable for use in the system of the invention are described in F. Rossi et al., *Long-Term Cardiopulmonary Bypass By Peripheral Cannulation In A Model of Total Heart Failure*, Journal of Thoracic and Cardiovascular Surgery (1990), 100:914–921; U.S. Pat. No. 4,540,399; and U.S. Pat. No. 5,011,469, which are all incorporated herein by reference.

With CPB established and balloon 330 blocking blood flow through the ascending aorta, the myocardium may then be paralyzed. In a preferred embodiment, a fluid containing cardioplegic agents is delivered by delivery device 390 through working port 366. The cardioplegic fluid preferably consists of an aqueous KCl solution mixed with oxygenated blood at a ratio of four parts blood to one part KCl solution. The aqueous KCl solution consists of crystalloid KCl mixed with saline to have a concentration in the range of 10–50 mEq $K^+$/liter, preferably 15–30 mEq $K^+$/liter. Delivery device 390 includes a cooler such as an ice bath (not shown) which cools the cardioplegic fluid to e.g. 3° C.–10° C., so as to maintain the heart at a low temperature and to minimize demand for oxygen. This is usually accomplished without applying external cooling to the heart as is generally applied in conventional open cardiac procedures. The cardioplegic fluid is infused into the ascending aorta through opening 331 at the distal end of partitioning device 320 to maintain a pressure in the aortic root distal to balloon 330 sufficient to induce flow of fluid into the coronary arteries through coronary ostia 384. A pressure of about 60–80 mmHg as measured through third lumen 348 is usually sufficient. Cardioplegic fluid is preferably delivered at a flowrate of about 250–350 ml/min. so as to deliver a total volume of 750–1000 ml in about 2–4 minutes, although this may vary depending upon patient anatomy, physiological changes such as coronary dilation, and other factors. In pumping the cardioplegic fluid through inner lumen 329, the fluid should be subject to a pump pressure of no more than about 300 mmHg to minimize damage to the blood component of the mixture. Cardioplegic fluid may also be infused in a retrograde manner through the coronary sinus, by means of a catheter (not shown) positioned transluminally through the right internal jugular vein, as described above. Heart contractions will then cease, with circulation to the remainder of the patient's body maintained by CPB system 394. Cardioplegic fluid flow to the patient's myocardium is maintained on a periodic basis, e.g., about every 10–20 minutes for 2–4 minutes, so long as the myocardium is to remain paralyzed. A comprehensive description of cardioplegic techniques suitable for use in the method of the invention is found in Buckberg, *Strategies and logic of cardioplegic delivery to prevent, avoid, and reverse ischemic and reperfusion damage*, J. Thorac. Cardiovasc. Surg. 1987;93: 127–39.

In addition to or instead of infusion of the blood/crystalloid cardioplegic solution, other techniques may be used to arrest heart contractions. A more concentrated crystalloid KCl solution not mixed with blood may be delivered through inner lumen 329 at higher pressures than with a blood cardioplegic fluid mixture, since without blood in the solution, there is no risk of hemolysis. This allows inner lumen 329 (as well as catheter shaft 322) to be of smaller cross-sectional area while still providing the necessary flowrate of fluid into the aortic root. However, the above blood cardioplegia technique is presently preferred because it is generally believed to provide greater myocardial protection. In another alternative technique, the patient's body may be cooled in a cold-temperature environment or by application of cold-packs to the chest to reduce the temperature of the myocardium sufficiently to induce fibrillation. The myocardium may be cooled directly by infusion of cold fluid such as cold blood or saline through the coronary arteries. Alternatively, electrical fibrillation may be accomplished by delivering electrical signals to the myocardium by means of electrodes placed on the exterior surface of the heart or externally on the chest. However, cardiac arrest by means of fibrillation is generally less desirable than chemical cardioplegic paralysis because there remains some degree of heart motion which could make surgical intervention more difficult and because there is a significantly higher demand for oxygen, reducing the safety and duration of the procedure.

Once the heart has been arrested and CPB established, a surgical procedure may be performed. The procedure will preferably be a less-invasive procedure performed endovascularly or thoracoscopically. In addition to endovascular aortic valve replacement (described above), the surgical procedures which may be performed using the device and system of the invention include repair or replacement of the aortic, mitral and other heart valves, repair of ventricular and atrial septal defects, septal myotomy, cardiac mapping and ablation to correct arrhythmias, coronary artery bypass grafting, angioplasty, atherectomy, myocardial drilling and revascularization, as well as pulmonary neurosurgical, and other procedures.

Partitioning device 320 of the present invention is particularly advantageous for endovascular introduction of surgical instruments through the aorta for procedures such as heart valve repair and replacement. As illustrated in FIG. 33, preshaped distal portion 332 of shaft 322 conforms to the shape of aortic arch 380 so that opening 331 at the distal end is positioned centrally within the ascending aorta and axially aligned with the center of aortic valve 404. This not only enhances infusion of cardioplegic fluid through opening 331, but ensures that surgical instruments such as valve cutter 406 introduced through first inner lumen 329 will be aligned with aortic valve 404, either to remove the valve, or to pass through it for intracardiac procedures. Advantageously, soft tip 338 at the distal end of shaft 322 prevents damage to tissue, particularly the fragile aortic valve leaflets, in the event of contact therewith.

While being particularly useful in conjunction with minimally-invasive cardiac procedures performed endovascularly and/or thoracoscopically, the partitioning device and system for arresting the heart disclosed herein are also useful in conventional open procedures performed with a thoracotomy. Partitioning device 320 may be used where an aortic cross-clamp would pose risks of embolus release due to calcification or other aortic conditions, or in a case of multiple reoperations where additional dissection, crossclamping and cannulation of the aorta may pose serious risks. In open procedures, partitioning device 320 may be introduced through the femoral or iliac arteries as described above, through the carotid artery 387, through the brachial artery 389, or through a penetration in the aorta itself, which is accessible as a result of the thoracotomy. In such cases, shaft 322 of partitioning device 320 may be substantially shorter in length, for example, 20 to 60 cm.

Periodically during the procedure, it may be necessary to decompress the left side of the heart by removing blood and other fluids which have accumulated in the aortic root, left atrium and/or left ventricle and which have not been removed by the pulmonary artery venting catheter (if utilized). To remove such fluids, suction may be applied through port 366 to the proximal end of inner lumen 329 so as to aspirate fluids from the aorta, left ventricle, and or left atrium upstream of balloon 330. Aortic root pressure is usually monitored during this procedure via third lumen 322. Such venting is usually performed after each periodic infusion of cardioplegic fluid and additionally as necessary to maintain decompression of the left side of the heart. In some cases, venting through inner lumen 329 is sufficient to maintain left heart decompression throughout the procedure, eliminating the need for a pulmonary artery venting catheter.

When the procedure has been completed, the heart is restarted by discontinuing any flow of cardioplegic fluid through partitioning device 320 or retrogradely through the coronary sinus, ventilating the lungs, and perfusing the coronary arteries with warm blood. The region upstream of balloon 330 may be irrigated by infusing a saline solution through first inner lumen 329. Blood and other fluids upstream of balloon 330 may then be aspirated through first inner lumen 329 to remove thrombi, air bubbles, or other emboli which may have been produced during the procedure, preventing such emboli from entering the brachiocephalic, carotid, or subclavian arteries and reducing the risk of complications such as strokes. Balloon 330 is deflated to allow warm blood from arterial cannula 398 to flow to the aortic root and through the coronary ostia into the coronary arteries, perfusing the myocardium. Normal heart contractions may resume promptly, or, if necessary, electrical defibrillation may be administered to correct heart rhythm. CPB is gradually discontinued, and CPB venous cannula 396 and arterial cannula 398 are removed. Partitioning device 320 is withdrawn from the body back through the site of entry, and the arterial penetration is closed. If the patient has been put under general anesthesia, the patient is then brought from anesthesia to consciousness.

It will be understood by those of skill in the art that various alternative configurations of endovascular partitioning device 320 are possible without departing from the scope of the present invention. One such alternative embodiment is illustrated in FIGS. 34A–34B. In this embodiment, partitioning device 320 has a pull wire 410 disposed in a lumen 412 in shaft 322. Pull wire 410 is attached at its distal end to an anchor plate 414 at distal end 324 of shaft 322, preferably offset from the central longitudinal axis of shaft 322. In one embodiment, pull wire 410 extends through a hole in anchor plate 414 and is retained against the anchor plate by a ball 416 fixed to the distal end of pull wire 410. In other respects, device 320 is configured as described above in connection with FIGS. 25–33, including a balloon 330 mounted to shaft 322 near distal end 324, an inflation lumen 418 in communication with the interior of balloon 330, a soft tip 338 attached to distal end 324 of shaft 322, and an inner lumen 329 in communication with distal opening 331. Tension may be applied to the proximal end (not shown) of pull wire 410 to deflect the distal portion 332 of shaft 322 into a shape suitable for positioning distal portion 332 in the aortic arch (as shown in phantom in FIG. 34A). In an alternative embodiment, an axially rigid, laterally-deflectable rod may be used in place of pull wire 410, whereby distal end 324 is deflected by applying a compressive force to the rod.

In an undeflected configuration (with tension relaxed on pull wire 410), distal portion 332 of the shaft is generally straight. Alternatively, all or part of distal portion 332 may be curved in an undeflected configuration to enhance positionability in the aortic arch. Preferably, a mechanism (not shown) will be provided at the proximal end of shaft 322 for applying tension to pull wire 410 and for locking the pull wire to maintain distal portion 332 in a desired shape. Various mechanisms may be used, such as those described in U.S. Pat. No. 5,030,204, the complete disclosure of which is incorporated herein by reference. Usually, shaft 322 is introduced into an artery in a generally straight configuration, and tension is applied to pull wire 410 to deflect distal portion 332 as the shaft is advanced into the aortic arch. Once distal portion 332 is positioned in the aortic arch, tension on pull wire 410 is adjusted so as to position distal end 324 radially within the ascending aorta so as to be spaced apart from the inner wall of the aorta and axially aligned with the center of the aortic valve. Pull wire 410 is then locked in tension to maintain distal portion 332 in its deflected configuration.

A further alternative embodiment of partitioning device 320 is illustrated in FIGS. 35A–35B. In this embodiment, shaft 322 is positionable in an interior lumen 420 of a guiding catheter 422. Device 320 may be configured as described above with reference to FIGS. 25–30, including balloon 330 near distal end 324, inner lumen 329, inflation lumen 346, pressure lumen 348, soft tip 338 attached to distal end 324, and triple-arm adapter 364 attached to proximal end 326. Guiding catheter 422 has a proximal end 424 and a distal end 426, with axial lumen 420 extending therebetween. A soft tip (not shown) may be attached to distal end 426 to minimize injury to the aorta or aortic valve in the event of contact therewith. A proximal adapter 428 is attached to proximal end 424, and has a first port 430 in communication with lumen 420 through which shaft 322 may be introduced, and a second port 432 in communication with lumen 420 for infusing or aspirating fluid. Port 430 may further include a hemostasis valve. Guiding catheter 422 also has a distal portion 434 which is either preshaped or deflectable into a shape generally conforming to the shape of the aortic arch. Techniques suitable for preshaping or deflecting distal portion 434 of guiding catheter 422 are described above in connection with FIGS. 25–30 and 34A–34B. In an exemplary embodiment, guiding catheter 422 is preshaped in a generally U-shaped configuration, with a radius of curvature in the range of 20–80 mm. In this embodiment, a stylet (not shown) like that described above in connection with FIGS. 25–30 is provided for straightening distal portion 434 for purposes of percutaneously introducing guiding catheter 422 into an artery.

In use, guiding catheter 422 is introduced into an artery, e.g. a femoral or iliac artery, and advanced toward the heart until distal end 426 is in the ascending aorta. A guidewire (not shown) may be used to enhance tracking. Where a stylet is used to straighten a preshaped guiding catheter for subcutaneous introduction, the stylet is withdrawn as preshaped distal portion 434 is advanced through the aortic arch. Once guiding catheter 422 is in position, shaft 322 may be introduced through port 430 and lumen 420 and advanced toward the heart until balloon 330 is disposed between the coronary ostia and the brachiocephalic artery, distal to the distal end 426 of guiding catheter 422. The distal portion 332 of shaft 322 (FIG. 25) is shaped to conform to the aortic arch by preshaped portion 434 of guiding catheter 422. Balloon 330 is then inflated to fully occlude the ascending aorta and block blood flow therethrough.

In yet another embodiment, shown in FIGS. 36A–36B, partitioning device 320 includes a shaping element 440 positionable in a lumen in shaft 322, such as third inner lumen 348. Shaping element 440 has a proximal end 442, a distal end 444 and a preshaped distal portion 446. Preshaped distal portion 446 may be generally U-shaped as illustrated, or may have an angular, "S" -shaped or other configuration in an unstressed condition, which will shape distal portion 332 to generally conform to at least a portion of the patient's aortic arch. Shaping element 440 is preferably stainless steel, nickel titanium alloy, or other biocompatible material with a bending stiffness greater than that of shaft 322 so as to deflect distal portion 332 into the desired shape. Shaping element 440 may be a guidewire over which shaft 322 is advanced to the ascending aorta, or a stylet which is inserted into third inner lumen 348 after shaft 322 is positioned with balloon 330 in the ascending aorta. In a preferred embodiment, shaping element 440 is configured to position distal end 324 of shaft 322 in a radial position within the ascending aorta to be spaced apart from the interior wall thereof, and in particular, axially aligned with the center of the aortic valve.

In a further aspect of the invention, illustrated in FIGS. 37A–37E, partitioning device 320 is coupled to an arterial bypass cannula 450 so as to allow both device 320 and cannula 450 to be introduced through the same arterial puncture. Arterial bypass cannula 450 is configured for connection to a cardiopulmonary bypass system for delivering oxygenated blood to the patient's arterial system. Arterial bypass cannula 450 has a distal end 452, a proximal end 454, a blood flow lumen 456 extending between proximal end 454 and distal end 452, and an outflow port 458 at distal end 452. A plurality of additional outflow ports 460 may be provided along the length of arterial bypass cannula 450, particularly near distal end 452. In a preferred embodiment, arterial bypass cannula 450 has a length between about 10 cm and 60 cm, and preferably between about 15 cm and 30 cm.

An adapter 462 is connected to proximal end 454 of bypass cannula 450, and includes a first access port 464 and a second access port 466, both in fluid communication with blood flow lumen 456. Access port 466 is configured for fluid connection to tubing from a cardiopulmonary bypass system, and preferably has a barbed fitting 468. Access port 464 is configured to receive partitioning device 320 therethrough. Preferably, a hemostasis valve 470, shown in FIGS. 37C and 37E, is mounted in access port 464 to prevent leakage of blood and other fluids through access port 464 whether or not shaft 322 of partitioning device 320 is positioned therein. Hemostasis valve 470 may have any number of well-known constructions, including, for example, an elastomeric disk 469 having one or more slits 472 through which shaft 422 may be positioned, and a diaphragm 471 adjacent to the disk with a central hole 474 for sealing around the periphery of shaft 322. A hemostasis valve of this type is described in U.S. Pat. No. 4,000,739, which is incorporated herein by reference. Other types of hemostasis valves may also be used, such as duck-bill valves, O-ring seals, and rotational or sliding mechanical valves. In addition, a Touhy-Borst valve 473 including a threaded, rotatable cap 475 may be provided on the proximal end of access port 464 to facilitate clamping and sealing around shaft 322 by tightening cap 475, which compresses O-rings 477 about shaft 322.

Shaft 322 of partitioning device 320 and blood flow lumen 456 of bypass cannula 450 are configured and dimensioned to facilitate sufficient blood flow through blood flow lumen 456 to support full cardiopulmonary bypass with complete cessation of cardiac activity, without an undesirable level of hemolysis. In a preferred embodiment, arterial bypass cannula 450 has an outer diameter of 6 mm to 10 mm, and blood flow lumen 456 has an inner diameter of 5 mm to 9 mm. Shaft 322 of partitioning device 320 has an outer diameter in the range of 2 mm to 5 mm. In this way, blood flow lumen 456, with shaft 322 positioned therein, facilitates a blood flow rate of at least about 4 liters/minute at a pump pressure of less than about 250 mmHg.

Arterial bypass cannula 450 is preferably introduced into an artery, usually a femoral artery, with partitioning device 320 removed from blood flow lumen 456. An obturator 476, illustrated in FIG. 37D, may be positioned in blood flow lumen 456 such that the tapered distal end 478 of obturator 476 extends distally from the distal end 452 of arterial bypass cannula 450. The arterial bypass cannula 450 may be introduced into the artery by various techniques including percutaneous methods such as the Seldinger technique, but is usually of sufficient size to require a surgical cutdown. A guidewire 480 may be slidably positioned through a lumen 482 in obturator 476 to facilitate introduction of arterial bypass cannula 450. Guidewire 480 is advanced into the artery through an arteriotomy, and arterial bypass cannula 450 with obturator 476 positioned therein is advanced into the artery over guidewire 480. Obturator 476 may then be removed, allowing partitioning device 320 to be introduced into the artery through blood flow lumen 456, usually over guidewire 480. Guidewire 480 may be advanced toward the heart and into the ascending aorta to facilitate positioning the distal end 324 of partitioning device 320 therein.

In an alternative embodiment, arterial bypass cannula 450 may be configured so that partitioning device 320 is not removable from blood flow lumen 456. In this embodiment, bypass cannula 450 is introduced into an artery with partitioning device 320 positioned in blood flow lumen 456. Partitioning device 320 may be slidable within a limited range of movement within blood flow lumen 456. Alternatively, partitioning device 320 may be fixed to arterial bypass cannula 450 to prevent relative movement between the two. For example, shaft 322 may be extruded from the same tubing which is used to form arterial bypass cannula 450. Or, shaft 322 may be attached within the interior of blood flow lumen 456 or at the distal end 452 of arterial bypass cannula 450. Additionally, distal end 452 of bypass cannula 450 may be tapered to seal around shaft 322 and may or may not be bonded to shaft 322. In this configuration, side ports 460 permit outflow of blood from blood flow lumen 456.

A further embodiment of an interventional device constructed in accordance with the principles of the invention is illustrated in FIGS. 38A–38F. In this embodiment, a cardiac venting device 480 is provided for withdrawing blood from the interior of the heart to prevent distention of the myocardium during cardiopulmonary bypass. Cardiac venting device 480 includes a venous bypass cannula 482 having a distal end 484 and a proximal end 486. A blood flow lumen 488, shown in FIGS. 38B and 38F, extends between distal end 484 and proximal end 486. An inflow port 490 in fluid communication with blood flow lumen 488 is disposed at distal end 484. A plurality of additional inflow ports 492 may be provided in venous bypass cannula 482 near distal end 484. An adapter 494 is mounted to proximal end 486 and includes a first access port 496 and a second access port 498 both in fluid communication with blood flow lumen 488. Access port 498 is configured for connection to a tube from a cardiopulmonary bypass system, and preferably includes a barbed fitting 500. Access port 496 is configured to receive a venting catheter 502 therethrough, and preferably includes a hemostasis valve 504, shown in FIG. 38C. Hemostasis valve 504 may have a construction like that of hemostasis valve 470 described above in connection with FIG. 37C.

Venting catheter 502 includes an elongated flexible shaft 506 having a distal end 508 and a proximal end 510. An inner lumen 512, shown in FIGS. 38B and 38F, extends from proximal end 510 to distal end 508, and is in fluid communication with an inflow port 514 in distal end 508. Additional side inflow ports as shown in FIG. 38F may also be provided near distal end 508. In one embodiment, as shown in FIG. 38A, an inflatable balloon 516 may be provided near distal end 508 proximal to distal port 514. An inflation lumen 518 extending through shaft 506 is in fluid communication with the interior of balloon 516 for delivering an inflation fluid thereto. Balloon 516 may be used to facilitate placement in the pulmonary artery, to facilitate measurement of wedge pressure in the pulmonary artery, or for other purposes. Additionally, a pressure lumen 520 may be provided in shaft 506, with a pressure port 522 at distal end 508 in fluid communication with pressure lumen 520. This facilitates pressure sensing at distal end 508. A triple arm adapter 524 is mounted to proximal end 510 of shaft 506. Adapter 524 has a first access port 526 in fluid communication with inner lumen 512, a second access port 528 in fluid communication with balloon inflation lumen 518, and a third access port 530 in fluid communication with pressure lumen 520.

Blood flow lumen 488 and shaft 506 are dimensioned and configured to facilitate adequate blood flow through blood flow lumen 488 to support full cardiopulmonary bypass with complete cessation of cardiac activity, without an undesirable level of hemolysis. In a preferred embodiment, venous bypass cannula 482 has an outer diameter of 6 mm to 12 mm, while blood flow lumen 488 has an inner diameter of 5 mm to 11.5 mm. Shaft 506 of venting catheter 502 preferably has an outer diameter between about 3 mm and 4 mm. Such a configuration facilitates a blood flow rate through blood flow lumen 488 of at least about 4 liters/minute at a vacuum pump pressure no less than about −75 mmHg.

The distal portion of venous bypass cannula 482 may be straight as shown in FIG. 38A, or, alternatively, may have a pre-shaped curvature as shown in FIG. 38D. Such a curved configuration may be advantageous in order to guide venting catheter 502 from the right atrium into the right ventricle through the tricuspid valve, as described more fully below. A variety of curves, from a 180° semi-circle, as shown in FIG. 38D, to a curve of 90° or less may be provided, according to the direction in which it is desired to guide venting catheter 502. An obturator 532 may be provided for straightening the distal portion for introduction of venous bypass cannula 482. Obturator 532 has a stiffness which is greater than that of the distal portion of venous bypass cannula 482 such that positioning obturator 532 in blood flow lumen 488 straightens the distal portion of bypass cannula 482. Obturator 532 may be provided with an inner lumen 534 through which a movable guidewire 536 may be positioned to facilitate introduction into the patient's venous system.

Cardiac venting device 480 may be introduced using various techniques, but, as with arterial bypass cannula 450 described above, will ordinarily require a surgical cutdown. Usually, venous bypass cannula 482 is introduced into a vein, preferably a femoral vein or internal jugular vein, without venting catheter 502 positioned in blood flow lumen 488. Obturator 532 may be positioned within blood flow lumen 488 to facilitate introduction. Preferably, venous bypass cannula 482 has a length of at least about 75 cm to allow the distal end 484 to be positioned near or within the right atrium of the heart via the inferior vena cava from a femoral vein. Alternatively, venous bypass cannula 482 may have a length of about 50 cm to 70 cm to facilitate introduction through the internal jugular vein in the patient's neck and positioning of distal end 484 in the superior vena cava and/or right atrium. Once venous bypass cannula 482 is in position, venting catheter 502 may be introduced through access port 496 and blood flow lumen 488 until distal end 508 is within the patient's heart. Venting catheter 502 may then be advanced until distal end 508 is in the desired portion of the heart to withdraw blood therefrom. Venting catheter 502 preferably has a length of at least about 110 cm to reach from a femoral vein to the pulmonary artery, or a length of about 70 cm to 90 cm to reach from the internal jugular vein to the pulmonary artery.

Alternative embodiments of cardiac venting device 480 are illustrated in FIGS. 39A–39D. In the embodiment of FIG. 39A, venous bypass cannula 482 comprises a non-tapered proximal portion 540 and a tapered distal portion 542. Blood flow lumen 488 extends from proximal end 486 to distal end 543. Inflow ports 492 are in fluid communication with blood flow lumen 488 as above. Non-tapered proximal portion 540 preferably has a length selected to allow inflow ports 492 to be positioned within the right atrium of the heart or in the inferior vena cava near the heart. A distal inflow port 544 and side inflow ports 546 are provided at the distal end 543. Distal inflow port 544 and side inflow ports 546 are also in fluid communication with blood flow lumen 488. Additional side inflow ports may be provided over the entire length of tapered section 542. A balloon (not shown) may also be provided at distal end 543, along with a pressure port (not shown), and associated lumens, as provided in previous embodiments. An adapter 548 is attached to proximal end 486. Adapter 548 may include an arm 550, preferably having a barbed fitting for connection to a tube from a cardiopulmonary bypass system. Other access ports may be provided in adapter 548 for balloon inflation and pressure measurement.

The total length of venous bypass cannula 482, including proximal portion 540 and tapered distal portion 542, is preferably at least 110 cm to reach the pulmonary artery from a femoral vein, or at least about 70 cm to 90 cm to reach the pulmonary artery from the internal jugular vein.

Tapered portion 542 may be tapered from an outer diameter of 6 mm–11 mm to an outer diameter of 3 mm–5 mm at distal end 543, so as to provide the flexibility and small profile necessary for positioning distal end 543 within the pulmonary artery, while maintaining a sufficiently large blood flow lumen 488 to support full cardiopulmonary bypass with cardiac function arrested.

In yet another embodiment, illustrated in FIGS. 39C and 39D, a shaft 506 of venting catheter 502 has a proximal end 552 which is attached to distal end 484 of venous bypass cannula 482. Shaft 506 has a distal end 554, an inner lumen 556 (FIG. 39D), and a distal port 558 in fluid communication with inner lumen 556 at distal end 554. A plurality of additional ports 560 may be provided along shaft 506 near distal end 554. Proximal end 552 of shaft 506 is attached to venous bypass cannula 482 by means of a frame 562, illustrated in FIG. 39D. Shaft 506 may be aligned coaxially with venous bypass cannula 482, or offset in an eccentric configuration. Inner lumen 556 is in fluid communication with blood flow lumen 488 in venous bypass cannula 482. In this way, blood withdrawn through distal ports 558, 560 in venting catheter 502 flows into blood flow lumen 488, along with blood withdrawn through inflow ports 490, 492. The proximal end of the device has a configuration suitable for connecting blood flow lumen 488 to a cardiopulmonary bypass system, and may include an adapter like adapter 548 illustrated in FIG. 39A.

Referring now to FIG. 40, the use of the devices illustrated in FIGS. 37–39 will be described. Arterial bypass cannula 450 is positioned in femoral artery 374, usually by surgical cutdown, with obturator 476 positioned in blood flow lumen 456. Guidewire 480 is first advanced through an arteriotomy into femoral artery 374, and arterial bypass cannula 450 along with obturator 476 are advanced over guidewire 480 into the artery. Obturator 476 may then be removed from blood flow lumen 456. Access port 466 on adapter 462 is connected to the oxygenated blood outlet of cardiopulmonary bypass system 394.

Venous bypass cannula 482 is introduced into femoral vein 570, usually on the same side of the patient as femoral artery 374 in which arterial bypass cannula 450 is introduced. In this way, the same surgical cutdown may be used for introduction of both devices. Venous bypass cannula 482 will usually be introduced over a guidewire 536 as described above, and may have obturator 532 positioned in blood flow lumen 488 to facilitate introduction. If venous bypass cannula 482 includes a shaped distal portion as shown in FIG. 38D, obturator 532 may be used to straighten the distal portion for introduction. Venous bypass cannula 482 is advanced through the femoral vein, iliac vein and inferior vena cava 574. Preferably, venous bypass cannula 482 is positioned so that the distal port 490 is within the right atrium 576. Inflow ports 492 will then be positioned within the right atrium 576 and/or within the inferior vena cava 574 near right atrium 576.

Cardiopulmonary bypass may then be initiated. Cardiopulmonary bypass system 394 receives deoxygenated blood from the patient's venous system through blood flow lumen 488 of venous bypass cannula 480, oxygenates the blood, and returns the oxygenated blood to blood flow lumen 456 of arterial bypass cannula 450.

Venting catheter 502 is then introduced through access port 496 into blood flow lumen 488. Venting catheter 502 is advanced toward the heart through blood flow lumen 488, and through distal port 490 into the right atrium 576. The venting catheter may be positioned in various locations within the heart, however, in a preferred embodiment, venting catheter 502 is positioned such that distal port 514 is within the pulmonary artery 578. Usually, this will be accomplished by positioning a Swan-Ganz catheter through blood flow lumen 488 and into right atrium 576 before introducing venting catheter 502. Usually, a balloon on the distal end of the Swan-Ganz catheter is inflated within the right atrium, and the distal end of the Swan-Ganz catheter is advanced from the right atrium 576, through the right ventricle 580, and into the pulmonary artery 578. Once the Swan-Ganz catheter has been positioned in the pulmonary artery, the balloon at its distal end may be deflated, and venting catheter 502 is advanced over the Swan-Ganz catheter until the distal end 508 of venting catheter 502 is within the pulmonary artery. The Swan-Ganz catheter may then be removed from the patient.

Access port 526 at the proximal end of venting catheter 502 is connected to a deoxygenated blood inlet of cardiopulmonary bypass system 394. Venting catheter 502 withdraws blood from the pulmonary artery 578 and delivers the blood to cardiopulmonary bypass system 394. Alternatively, access port 526 may be connected to a separate roller pump (not shown) which feeds the blood withdrawn from the heart into filter/recovery reservoir 400, then returns the blood to CPB system 394. If a balloon 516 is provided at the distal end of venting catheter 502, a balloon inflation device, such as a syringe 582, is connected to access port 528, and inflation fluid is injected into balloon 516. A pressure measurement device 590 is connected to access port 530 for monitoring the pressure within the pulmonary artery through pressure port 522.

Cardiac function may then be arrested. Guidewire 480 may be advanced through arterial bypass cannula 450 until its distal end is in ascending aorta 380. Partitioning device 320 may then be introduced through blood flow lumen 456 into femoral artery 374 and advanced toward the heart until balloon 330 is disposed in the ascending aorta between brachiocephalic artery 386 and coronary ostia 384. Guidewire 480 may then be removed. If partitioning device 320 has a preshaped distal portion 332, an obturator as described above may be used for straightening distal portion 332 during introduction. Occlusion balloon 330 of partitioning device 320 is expanded to occlude ascending aorta 382. Cardioplegic fluid is delivered through inner lumen 329 of partitioning device 320 into ascending aorta 382 upstream of occlusion balloon 330, from which the cardioplegic fluid flows into the coronary arteries to perfuse the myocardium. As described above in reference to FIG. 32, a cooled mixture of blood and a KCl/saline solution infused at a rate of about 300 ml/min. at no more than 300 mmHg is the presently preferred technique of inducing cardioplegia. Cardioplegic fluid may also be infused in a retrograde manner through the coronary sinus, as previously described. The myocardium is quickly paralyzed, and cardiac function ceases. Cardiopulmonary bypass system 394 maintains peripheral circulation of oxygenated blood through venous bypass cannula 482 and arterial bypass cannula 450. As described above in reference to FIG. 32, it may be necessary to periodically vent the left side of the heart of blood and other fluids not removed by pulmonary artery venting catheter 502. To accomplish this, suction may be applied through working port 366 to withdraw fluids from the left atrium, left ventricle, and aortic root through inner lumen 329, from which the fluids may be passed to filter/recovery unit 400 and cardiopulmonary bypass system 394 for oxygenation and return to the patient's arterial system. Aortic root pressure is monitored during the procedure through third lumen 348.

The patient is thus prepared for a cardiovascular surgical procedure with the heart arrested and cardiopulmonary bypass established, all through a single arterial puncture and a single venous puncture, without any incisions in the chest. Preferably, minimally-invasive surgical techniques are then utilized to perform the surgical procedure, which may be any of a number of cardiac, vascular, pulmonary, or neurosurgical procedures.

Following surgery, the patient's heart is restarted by discontinuing any flow of cardioplegic fluid through partitioning device 320 or retrogradely through the coronary sinus, ventilating the lungs, and perfusing the coronary arteries with warm blood. The region upstream of balloon 330 may first be irrigated by infusing a saline solution through first inner lumen 329. Blood and other fluids upstream of balloon 330 may then be aspirated through first inner lumen 329 to remove thrombi, air bubbles, or other emboli which may have been produced during the procedure, preventing such emboli from entering the brachiocephalic, carotid, or subclavian arteries and reducing the risk of complications such as strokes. Balloon 330 is deflated to allow warm blood from arterial bypass cannula 450 to flow through the ascending aorta to the coronary arteries, perfusing the myocardium. Normal heart contractions may resume promptly, or, if necessary, electrical defibrillation may be administered to correct heart rhythm. Partitioning device 320 is withdrawn from the body back through arterial bypass cannula 450. Venting catheter 502 is withdrawn from the pulmonary artery (first deflating balloon 516, if inflated) and out of the body back through venous bypass cannula 482. CPB is gradually discontinued, and venous bypass cannula 482 and arterial bypass cannula 450 are removed. Arterial and venous punctures or cut-downs are closed. If the patient has been put under general anesthesia, the patient is then brought from anesthesia to consciousness.

It will be understood to those of skill in the art that a variety of devices may be introduced through blood flow lumen 456 of arterial bypass cannula 450 or through blood flow lumen 488 of venous bypass cannula 482 instead of aortic partitioning device 322 and cardiac venting catheter 502. For example, coronary angioplasty or atherectomy catheters may be introduced through arterial bypass cannula 450 and advanced into the coronary arteries, facilitating CPB assist during angioplasty and atherectomy procedures through a single femoral arterial penetration. A catheter for retroperfusion of cardioplegic fluid from the coronary sinus may be introduced through venous cannula 482 from either the internal jugular vein, subclavian vein, or a femoral vein into the heart and into the coronary sinus. Electrophysiology catheters for myocardial mapping and ablation may be introduced through arterial bypass cannula 450 or venous bypass cannula 482 and advanced into the heart or coronary arteries to facilitate CPB assist during such procedures without an additional femoral arterial or venous penetration. A variety of endovascular instruments for inspecting and treating the heart and great vessels, including angioscopes, valve repair devices, valve removal devices, devices for introduction and attachment of valve prostheses, septal defect repair devices, aneurysm treatment devices, vascular stents, staplers, shunts or grafts to facilitate coronary artery bypass grafting, and other devices may be introduced through arterial bypass cannula 450 or venous bypass cannula 482, facilitating CPB assist during such interventional procedures without requiring additional arterial or venous penetrations.

The devices and methods disclosed herein offer significant advantages over conventional techniques. Important among these advantages is the ability to establish cardiopulmonary bypass and perform interventional procedures within the heart and great vessels with a minimum of venous and arterial penetrations, thereby reducing substantially the morbidity and mortality of such procedures. Further, the invention facilitates performing such interventional procedures and establishing cardiopulmonary bypass through a single arterial penetration and a single venous penetration. In this way, the invention not only reduces the total number of penetrations and the associated trauma and risks attendant such penetrations, but allows a greater number of patients to receive closed-chest surgical treatment who, because of conditions in one or more femoral vessels, would otherwise be prevented from receiving such treatment.

The invention further facilitates arresting cardiac function and establishing cardiopulmonary bypass by means of an endovascular device introduced through a single femoral arterial penetration, eliminating the need for a conventional gross thoracotomy. By obviating the need to open the chest for external clamping of the aorta, the invention facilitates the performance of a new generation of minimally-invasive cardiac and vascular procedures. Elimination of a median sternotomy or gross thoracotomy in such procedures produces lower mortality and morbidity, reduced patient suffering, decreased hospitalization and recovery time, and reduced medical costs. Moreover, the invention is useful even in open-chest procedures as a substitute for the aortic cross-clamp where calcification or other conditions could make external aortic clamping undesirable.

While the present invention has been described herein in terms of certain preferred embodiments, it will be apparent to one of ordinary skill in the art that many modifications and improvements can be made to the invention without departing from the scope thereof.

What is claimed is:

1. Apparatus for venting blood from a pulmonary artery leading away from a right ventricle of a patient's heart, the system comprising:

a venting catheter comprising a flexible elongate shaft having a distal end, a proximal end, and an inner lumen extending from the proximal end to an inlet port at the distal end configured to withdraw blood from the pulmonary artery, the shaft having a length selected to allow the distal end to be positioned in the pulmonary artery with the proximal end extending transluminally to a peripheral vein and out of the patient through a puncture in the peripheral vein; and flow-directed means coupled to the shaft and configured to be carried by blood flow through the heart into the pulmonary artery, the flow-directed means being a flow-directed catheter slidably positionable in the inner lumen of the shaft, the flow-directed catheter having an expandable member mounted to a distal end thereof which is extendable from the distal end of the shaft so as to be carried by blood flow through the heart into the pulmonary artery.

2. The apparatus of claim 1 wherein the flow-directed means comprises an expandable member attached to the shaft near the distal end thereof, the expandable member being configured to be carried by blood flow through the heart into the pulmonary artery.

3. The apparatus of claim 2 wherein the expandable member comprises a balloon having an interior, the shaft further having an inflation lumen extending from the proximal end to an opening near the distal end in communication with the interior of the balloon.

4. The apparatus of claim 1 wherein the expandable member comprises a balloon having an interior, the flow directed catheter having an inflation lumen extending from the proximal end to an opening near the distal end in communication with the interior of the lumen.

5. The apparatus of claim 1 further comprising a pressure lumen in the shaft extending from the proximal end to a pressure port near the distal end.

* * * * *